(12) United States Patent
Roth et al.

(10) Patent No.: US 7,608,277 B2
(45) Date of Patent: Oct. 27, 2009

(54) TUBERCULOSIS NUCLEIC ACIDS, POLYPEPTIDES AND IMMUNOGENIC COMPOSITIONS

(75) Inventors: David Roth, San Diego, CA (US); Huaping He, San Diego, CA (US)

(73) Assignee: Gene Therapy Systems, Inc., San Diego, CA (US)

( * ) Notice: Subject to any disclaimer, the term of this patent is extended or adjusted under 35 U.S.C. 154(b) by 131 days.

(21) Appl. No.: 11/291,616

(22) Filed: Nov. 30, 2005

(65) Prior Publication Data

US 2006/0140982 A1    Jun. 29, 2006

Related U.S. Application Data

(60) Provisional application No. 60/632,573, filed on Dec. 1, 2004, provisional application No. 60/730,951, filed on Oct. 26, 2005.

(51) Int. Cl.
A61K 39/04      (2006.01)
A61K 49/00      (2006.01)
A61K 39/00      (2006.01)

(52) U.S. Cl. .............. 424/248.1; 424/9.1; 424/9.2; 424/184.1; 424/185.1; 424/190.1; 424/234.1; 424/278.1; 530/300; 530/350

(58) Field of Classification Search .............. 424/9.1, 424/9.2, 184.1, 185.1, 190.1, 234.1, 248.1, 424/278.1; 530/300, 350
See application file for complete search history.

(56) References Cited

U.S. PATENT DOCUMENTS

| | | | |
|---|---|---|---|
| 4,376,110 A | 3/1983 | David et al. | |
| 4,946,778 A | 8/1990 | Ladner et al. | |
| 6,280,977 B1 | 8/2001 | Liang et al. | |
| 6,350,456 B1 * | 2/2002 | Reed et al. | 424/248.1 |
| 6,403,100 B1 | 6/2002 | Barry et al. | |
| 6,458,366 B1 * | 10/2002 | Reed et al. | 424/248.1 |
| 6,544,522 B1 * | 4/2003 | Skeiky et al. | 424/190.1 |
| 6,592,877 B1 * | 7/2003 | Reed et al. | 424/248.1 |
| 6,641,814 B1 * | 11/2003 | Andersen et al. | 424/190.1 |
| 6,936,470 B2 | 8/2005 | Liang et al. | |

FOREIGN PATENT DOCUMENTS

| | | | |
|---|---|---|---|
| WO | WO88/05823 | * | 8/1988 |
| WO | WO 98/30699 | * | 6/1998 |
| WO | WO 99/02670 | | 1/1999 |
| WO | WO 99/09186 | * | 2/1999 |
| WO | WO00/21983 | * | 4/2000 |
| WO | WO 00/21983 | * | 4/2000 |
| WO | WO 02/04018 | | 1/2002 |
| WO | WO 02/083871 | | 10/2002 |
| WO | WO03/033530 | * | 4/2003 |
| WO | WO 2006/060484 | | 6/2006 |

OTHER PUBLICATIONS

GenBank search result, AAP80214.*
Hochuli, E., et al. "Genetic approach to facilitate purification of recombinant proteins with a novel metal chelate adsorbent", Bio/Technology, vol. 6, No. 11, pp. 1321-1325, 1988.*
Bird, et al. "Single-Chain Antigen-Binding Proteins." Science 242:423-26 (1988).
Chow et al. "Improvement of Hepatitis B Virus DNA Vaccines by Plasmids Coexpressing Hepatitis B Surface Antigen and Interleukin-2." J. Virol. 71(1):169-178 (1997).
Cole, et al. "The EBV-Hybridoma Technique and its Application to Human Lung Cancer." Monoclonal Antibodies And Cancer Therapy. Alan R. Liss, Inc., New York. 77-96 (1985).
Cole, et al. "Generation of human monoclonal antibodies reactive with cellular antigens." Proc. Natl. Acad. Sci. USA. 80:2026-30 (1983).
Delcher, et al. "Improved microbial gene identification with GLIMMER." Nucleic Acids Res. 27(23):4636-4641 (1999).
Furth, et al. "Temporal control of gene expression in transgenic mice by a tetracycline-responsive promoter." Proc. Natl. Acad. Sci. USA. 91:9302-6 (1994)).
Heller et al. "Electroporation for targeted gene transfer." Expert Opin. Drug Deliv. 2(2):255-268 (2005).
Huse, et al. "Generation of a Large Combinatorial Library of the Immunoglobulin Repertoire in Phage Lambda." Science. 246: 1275-81 (1989).
Huston, et al. Protein engineering of antibody binding sites: Recovery of specific activity in an anti-digoxin single-chain Fv analogue produced in *Escherichia coli*. Proc. Natl. Acad. Sci. USA. 85:5879-83 (1988).
International Search Report for International Application No. PCT/US2005/043329 dated Oct. 10, 2006.
Köhler and Milstein. "Continuous cultures of fused cells secreting antibody of predefined specificity." Nature. 256:495-7 (1975).
Kozbor, et al. "The production of monoclonal antibodies from human lymphocytes." Immunology Today. 4(3):72-79 (1983).
Lee et al. "Optimal Induction of Hepatitis C Virus Envelope-Specific Immunity by Bicistronic Plasmid DNA Inoculation with the Granulocyte-Macrophage Colony-Stimulating Factor Gene." J. Virol. 72(10):8430-8436 (1998).
Lee et al. "DNA inoculations with HIV-1 recombinant genomes that express cytokine genes enhance HIV-1 specific immune responses." Vaccine. 17:473-479 (1999).

(Continued)

*Primary Examiner*—Rodney P. Swartz
(74) *Attorney, Agent, or Firm*—Knobbe, Martens, Olson & Bear LLP

(57) ABSTRACT

The present invention provides transcriptionally active Mtb polynucleotides, recombinant Mtb peptides and polypeptides, and immunogenic Mtb antigens. Immunogenic compositions are also provided that may be useful as recombinant, subunit and DNA vaccines. In addition, the invention provides diagnostic kits for Mtb.

21 Claims, 6 Drawing Sheets

OTHER PUBLICATIONS

McClements et al. "Immunization with DNA vaccines encoding glycoprotein D or glycoprotein B, alone or in combination, induces protective immunity in animal models of herpes simplex virus-2 disease." Proc. Natl. Acad. Sci. USA. 93:11414-11420 (1996).

Morrison, et al. "Chimeric human antibody molecules: Mouse antigen-binding domains with human constant region domains." Proc. Natl. Acad. Sci. 81:6851-6855 (1984).

No, et al. "Ecdysone-inducible gene expression in mammalian cells and transgenic mice." Proc. Natl. Acad. Sci. USA. 93:3346-51 (1996).

Salzberg et al. "Microbial gene identification using interpolated Markov models." Nucleic Acids Res. 26(2): 544-548 (1998).

Takeda, et al. "Construction of chimaeric processed immunoglobulin genes containing mouse variable and human constant region sequences." Nature. 314:452-54 (1985).

Ulmer at al. "Heterologous Protection Against Influenza by Injection of DNA Encoding a Viral Protein." Science. 259:1745-1749 (1993).

Wang, et al. "Induction of Humoral and Cellular Immune Responses to the Human Immunodeficiency Type 1 Virus in Nonhuman Primates by in Vivo DNA Inoculation." Virology. 211:102-112 (1995).

Ward, et al. "Binding activities of a repertoire of single immunoglobulin variable domains secreted from *Escherichia coli*." Nature. 341:544-46 (1989).

Xiang et al. "Vaccination with a Plasmid Vector Carrying the Rabies Virus Glycoprotein Gene Induces Protective Immunity against Rabies Virus." Virology. 199:132-140 (1994).

* cited by examiner

Step 1  Synthesize gene-specific custom primers containing the universal TAP ends 5' and 3' -Custom Oligos Step 2  Amplify the gene-of-interest with the custom primers to create the TAP Primary Fragment Step 3

This fragment is transcriptionally active ready for transfection into cultured cells, or injection into animals

SEQUENCE LISTING

<160> NUMBER OF SEQ ID NOS: 133

<210> SEQ ID NO 1
<211> LENGTH: 69
<212> TYPE: DNA
<213> ORGANISM: Homo sapiens

<400> SEQUENCE: 1
atggatgcaa tgaagagagg gctctgctgt gtgctgctgc tgtgtggagc agtcttcgtt    60
tcgcccagc                                                            69

<210> SEQ ID NO 2
<211> LENGTH: 17
<212> TYPE: DNA
<213> ORGANISM: Artificial Sequence
<220> FEATURE:
<223> OTHER INFORMATION: Synthetic Oligonucleotide Primer

<400> SEQUENCE: 2
ccgccatgtt gacattg                                                   17

<210> SEQ ID NO 3
<211> LENGTH: 64
<212> TYPE: DNA
<213> ORGANISM: Artificial Sequence
<220> FEATURE:
<223> OTHER INFORMATION: Synthetic Oligonucleotide Primer

<400> SEQUENCE: 3
ggcagatctg ggaggctagc gtaatccgga acatcgtatg ggtacattgt taagtcgacg    60
gtgc                                                                 64

<210> SEQ ID NO 4
<211> LENGTH: 56
<212> TYPE: DNA
<213> ORGANISM: Artificial Sequence
<220> FEATURE:
<223> OTHER INFORMATION: Synthetic Oligonucleotide Primer

<400> SEQUENCE: 4
gatcccgggt acccatacga tgttccggat tacgcttagg ggagatctca gacatg        56

<210> SEQ ID NO 5
<211> LENGTH: 32
<212> TYPE: DNA
<213> ORGANISM: Artificial Sequence
<220> FEATURE:
<223> OTHER INFORMATION: Synthetic Oligonucleotide Primer

<400> SEQUENCE: 5
caggatatca tgcctgcagg acgactctag ag                                  32

<210> SEQ ID NO 6
<211> LENGTH: 169
<212> TYPE: DNA
<213> ORGANISM: Artificial Sequence
<220> FEATURE:

<223> OTHER INFORMATION: Synthetic Oligonucleotide Primer

<400> SEQUENCE: 6

```
cggtcacgct tgggactgcc ataggctggc ccggtgatgc cggccacgat gcgtccggcg    60
tagaggatcg agatctcgat cccgcgaaat taatacgact cactataggg agaccacaac   120
ggtttccctc tagaaataat tttgtttaac tttaagaagg agatatacc               169
```

<210> SEQ ID NO 7
<211> LENGTH: 238
<212> TYPE: DNA
<213> ORGANISM: Artificial Sequence
<220> FEATURE:
<223> OTHER INFORMATION: Synthetic Oligonucleotide Primer

<400> SEQUENCE: 7

```
ggggggggtt ctcatcatca tcatcatcat taataaaagg gcgaattcca gcacactggc    60
ggccgttact agtggatccg gctgctaaca aagcccgaaa ggaagctgag ttggctgctg   120
ccaccgctga gcaataacta gcataacccc ttggggcctc taaacgggtc ttgaggggtt   180
ttttgctgaa aggaggaact atatccggag cgactccac ggcacgttgg caagctcg     238
```

<210> SEQ ID NO 8
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 8

```
gaaggagata taccatgcat catcatcatc atcatatggc caccacccett              50
```

<210> SEQ ID NO 9
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 9

```
tgatgatgag aacccccccc gttggtggac cggatctgaa                          40
```

<210> SEQ ID NO 10
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 10

```
gaaggagata taccatgcat catcatcatc atcatgtgaa gcgtggactg                50
```

<210> SEQ ID NO 11
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 11

```
tgatgatgag aacccccccc ggaacaggtc acctcgattt                          40
```

<210> SEQ ID NO 12
<211> LENGTH: 50

```
<212> TYPE: DNA
<213> ORGANISM: Artificial Sequence
<220> FEATURE:
<223> OTHER INFORMATION: Synthetic Oligonucleotide Primer

<400> SEQUENCE: 12
gaaggagata taccatgcat catcatcatc atcatatggc caatccgttc            50

<210> SEQ ID NO 13
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 13
tgatgatgag aaccccccccc ctgaccgtag ggctgctcgg                      40

<210> SEQ ID NO 14
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 14
gaaggagata taccatgcat catcatcatc atcatatgac gcttaaggtc            50

<210> SEQ ID NO 15
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 15
tgatgatgag aaccccccccc tgccgcgtat cccggcgtct                      40

<210> SEQ ID NO 16
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 16
gaaggagata taccatgcat catcatcatc atcatatggc tgaaaactcg            50

<210> SEQ ID NO 17
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 17
tgatgatgag aaccccccccc cttctgggtg accttcttgg                      40

<210> SEQ ID NO 18
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 18
```
gaaggagata taccatgcat catcatcatc atcatatggc acgctgcgat                    50

<210> SEQ ID NO 19
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 19
tgatgatgag aaccccccc gcttcccaac tcgatcgggg                                 40

<210> SEQ ID NO 20
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 20
gaaggagata taccatgcat catcatcatc atcatatgac caaacccaca                    50

<210> SEQ ID NO 21
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 21
tgatgatgag aaccccccc cgcagccgtg gtcggagctt                                 40

<210> SEQ ID NO 22
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 22
gaaggagata taccatgcat catcatcatc atcatatggc acgctgcgat                    50

<210> SEQ ID NO 23
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 23
tgatgatgag aaccccccc gcttcccaac tcgatcgggg                                 40

<210> SEQ ID NO 24
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 24
gaaggagata taccatgcat catcatcatc atcatgtgag tgacgaggac                    50

<210> SEQ ID NO 25
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 25
tgatgatgag aacccccccc tggttgccga gcccactcgg          40

<210> SEQ ID NO 26
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 26
gaaggagata taccatgcat catcatcatc atcatatgtg cggacggttt          50

<210> SEQ ID NO 27
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 27
tgatgatgag aaccccccc cagcagctgg atctgctcgg          40

<210> SEQ ID NO 28
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 28
gaaggagata taccatgcat catcatcatc atcatgtgcc agagctggag          50

<210> SEQ ID NO 29
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 29
tgatgatgag aaccccccc gtccgccagc ttgaccgact          40

<210> SEQ ID NO 30
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 30
gaaggagata taccatgcat catcatcatc atcatatggc agactgtgat          50

<210> SEQ ID NO 31
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 31
tgatgatgag aaccccccc ggagatggtg atcgactcga          40

-continued

<210> SEQ ID NO 32
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 32
gaaggagata taccatgcat catcatcatc atcatatggg ggcgcagccg       50

<210> SEQ ID NO 33
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 33
tgatgatgag aaccccccc acgtcgtgat gtcaacgtgt                   40

<210> SEQ ID NO 34
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 34
gaaggagata taccatgcat catcatcatc atcatatgat gcaccgaacc       50

<210> SEQ ID NO 35
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 35
tgatgatgag aaccccccc tcggcttcgt ggtaaaccccg                  40

<210> SEQ ID NO 36
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 36
gaaggagata taccatgcat catcatcatc atcatatgcc caatttctgg       50

<210> SEQ ID NO 37
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 37
tgatgatgag aaccccccc aaacttagga tgttccttgt                   40

<210> SEQ ID NO 38
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 38
gaaggagata taccatgcat catcatcatc atcatatggc cgacgctgac          50

<210> SEQ ID NO 39
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 39
tgatgatgag aaccccccccc gtcgcggagc acaacgactc                    40

<210> SEQ ID NO 40
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 40
gaaggagata taccatgcat catcatcatc atcatttgtg tgcaaaaccg          50

<210> SEQ ID NO 41
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 41
tgatgatgag aaccccccccc cgccgatgct cgcttcggcc                    40

<210> SEQ ID NO 42
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 42
gaaggagata taccatgcat catcatcatc atcatatgat tgatgaggct          50

<210> SEQ ID NO 43
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 43
tgatgatgag aaccccccccc gacctccagc agctcgcctt                    40

<210> SEQ ID NO 44
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 44
gaaggagata taccatgcat catcatcatc atcatatgcc caagctcagc          50

<210> SEQ ID NO 45

```
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 45
tgatgatgag aaccccccccc gcgaggcagg gattctggtc                              40

<210> SEQ ID NO 46
<211> LENGTH: 432
<212> TYPE: DNA
<213> ORGANISM: Mycobacterium tuberculosis

<400> SEQUENCE: 46
atggccacca cccttcccgt tcagcgccac ccgcggtccc tcttcccga gttttctgag          60 ctgttcgcgg ccttcccgtc attcgccgga ctccggccca ccttcgacac ccggttgatg        120
cggctggaag acgagatgaa agaggggcgc tacgaggtac gcgcggagct tcccggggtc        180
gaccccgaca aggacgtcga cattatggtc cgcgatggtc agctgaccat caaggccgag        240
cgcaccgagc agaaggactt cgacggtcgc tcggaattcg cgtacggttc cttcgttcgc        300
acggtgtcgc tgccggtagg tgctgacgag gacgacatta aggccaccta cgacaagggc        360
attcttactg tgtcggtggc ggtttcggaa gggaagccaa ccgaaaagca cattcagatc        420
cggtccacca ac                                                            432

<210> SEQ ID NO 47
<211> LENGTH: 477
<212> TYPE: DNA
<213> ORGANISM: Mycobacterium tuberculosis

<400> SEQUENCE: 47
gtgaagcgtg gactgacggt cgcggtagcc ggagccgcca ttctggtcgc aggtctttcc         60
ggatgttcaa gcaacaagtc gactacagga agcggtgaga ccacgaccgc ggcaggcacg        120
acggcaagcc ccggcgccgc ctccgggccg aaggtcgtca tcgacggtaa ggaccagaac        180
gtcaccggct ccgtggtgtg cacaaccgcg gccggcaatg tcaacatcgc gatcggcggg        240
gcggcgaccg gcattgccgc cgtgctcacc gacggcaacc ctccggaggt gaagtccgtt        300
gggctcggta acgtcaacgg cgtcacgctg ggatacacgt cgggcaccgg acagggtaac        360
gcctcggcaa ccaaggacgg cagccactac aagatcactg ggaccgctac cggggtcgac        420
atggccaacc cgatgtcacc ggtgaacaag tcgttcgaaa tcgaggtgac ctgttcc           477

<210> SEQ ID NO 48
<211> LENGTH: 810
<212> TYPE: DNA
<213> ORGANISM: Mycobacterium tuberculosis

<400> SEQUENCE: 48
atggccaatc cgttcgttaa agcctggaag tacctcatgg cgctgttcag ctcgaagatc         60
gacgagcatg ccgaccccaa ggtgcagatt caacaggcca ttgaggaagc acagcgcacc        120
caccaagcgc tgactcaaca ggcggcgcaa gtgatcggta accagcgtca attggagatg        180
cgactcaacc gacagctggc ggacatcgaa aagcttcagg tcaatgtgcg ccaagccctg        240
acgctggccg accaggccac cgccgccgga gacgctgcca aggccaccga atacaacaac        300
gccgccgagg cgttcgcagc ccagctggtg accgccgagc agagcgtcga agacctcaag        360
acgctgcatg accaggcgct tagcgccgca gctcaggcca agaaggccgt cgaacgaaat        420
```

```
gcgatggtgc tgcagcagaa gatcgccgag cgaaccaagc tgctcagcca gctcgagcag      480
gcgaagatgc aggagcaggt cagcgcatcg ttgcggtcga tgagtgagct cgccgcgcca      540
ggcaacacgc cgagcctcga cgaggtgcgc gacaagatcg agcgtcgcta cgccaacgcg      600
atcggttcgg ctgaacttgc cgagagttcg gtgcagggcc ggatgctcga ggtggagcag      660
gccgggatcc agatggccgg tcattcacgg ttggaacaga tccgcgcatc gatgcgcggt      720
gaagcgttgc cggccggcgg gaccacggct accccagac cggccaccga acttctggc        780 ggggctattg ccgagcagcc ctacggtcag                                       810

<210> SEQ ID NO 49
<211> LENGTH: 867
<212> TYPE: DNA
<213> ORGANISM: Mycobacterium tuberculosis

<400> SEQUENCE: 49
atgacgctta aggtcaaagg cgagggactc ggtgcgcagg tcacaggggt cgatcccaag       60
aatctggacg atataaccac cgacgagatc cgggatatcg tttacacgaa caagctcgtt     120
gtgctaaaag acgtccatcc gtctccgcgg gagttcatca aactcggcag ataattgga      180 caaatcgttc cgtattacga acccatgtac catcacgaag accacccgga gatctttgtc     240
tcctccactg aggaaggtca gggggtccca aaaaccggcg cgttctggca tatcgactat     300
atgtttatgc cggaaccttt cgcgttttcc atggtgctgc cgctggcggt gcctggacac     360
gaccgcggga cctatttcat cgatctcgcc agggtctggc agtcgctgcc cgccgccaag     420
cgagacccgg cccgcggaac cgtcagcacc cacgaccctc gacgccacat caagatccga     480
cccagcgacg tctaccggcc catcgagag gtatgggacg agatcaaccg gaccacgccc      540
ccaataaagt ggcctacggt catccggcac ccaaagaccg ccaagagat cctctacatc      600 tgcgcgacgc gcaccaccaa gatcgaggac aaggacggca atccggttga tccggaggtg     660
ctgcaagaac tcatggccgc gaccggacag ctcgatcctg agtaccagtc gccgttcata     720
catactcagc actaccaggt tggcgacatc atcttgtggg acaaccgggt tctcatgcac     780
cgagcgaagc acggcagcgc gcgggcact ctgacgacct accgcctgac catgcttgat      840
ggcctcaaga cgccgggata cgcggca                                         867

<210> SEQ ID NO 50
<211> LENGTH: 597
<212> TYPE: DNA
<213> ORGANISM: Mycobacterium tuberculosis

<400> SEQUENCE: 50
atggctgaaa actcgaacat tgatgacatc aaggctccgt tgcttgccgc gcttggagcg      60
gccgacctgg ccttggccac tgtcaacgag ttgatcacga acctgcgtga gcgtgcggag     120
gagactcgta cggacacccg cagccgggtc gaggagagcc gtgctcgcct gaccaagctg     180
caggaagatc tgcccgagca gctcaccgag ctgcgtgaga gttcaccgc cgaggagctg      240 cgtaaggccg ccgagggcta cctcgaggcc gcgactagcc ggtacaacga gctggtcgag     300
cgcggtgagg ccgctctaga gcggctgcgc agccagcaga gcttgaggga agtgtcggcg     360
cgcgccgaag gctacgtgga ccaggcggtg gagttgaccc aggaggcgtt gggtacggtc     420
gcatcgcaga cccgcgcggt cggtgagcgt gccgccaagc tggtcggcat cgagctgcct     480
aagaaggctg ctccggccaa gaaggccgct ccggccaaga aggccgctcc ggccaagaag     540
```
gcggcggcca agaaggcgcc cgcgaagaag gcggcggcca agaaggtcac ccagaag        597

<210> SEQ ID NO 51
<211> LENGTH: 831
<212> TYPE: DNA
<213> ORGANISM: Mycobacterium tuberculosis

<400> SEQUENCE: 51
atggcacgct gcgatgtcct ggtctccgcc gactgggctg agagcaatct gcacgcgccg        60
aaggtcgttt tcgtcgaagt ggacgaggac accagtgcat atgaccgtga ccatattgcc       120
ggcgcgatca agttggactg cgcaccgac ctgcaggatc cggtcaaacg tgacttcgtc       180
gacgcccagc aattctccaa gctgctgtcc gagcgtggca tcgccaacga ggacacggtg       240
atcctgtacg gcggcaacaa caattggttc gccgcctacg cgtactggta tttcaagctc       300
tacggccatg agaaggtcaa gttgctcgac ggcggccgca agaagtggga gctcgacgga       360
cgcccgctgt ccagcgaccc ggtcagccgg ccggtgacct cctacaccgc ctccccgccg       420
gataacacga ttcgggcatt ccgcgacgag gtcctggcgg ccatcaacgt caagaaccta       480
atcgacgtgc gctctcccga cgagttctcc ggcaagatcc tggcccccgc gcacctgccg       540
caggaacaaa gccagcggcc cggacacatt cctggtgcca tcaacgtgcc gtggagcagg       600
gccgccaacg aggacggcac cttcaagtcc gatgaggagt tggccaagct ttacgccgac       660
gccggcctag acaacagcaa ggaaacgatt gcctactgcc gaatcgggga acggtcctcg       720
cacacctggt tcgtgttgcg ggaattactc ggacaccaaa acgtcaagaa ctacgacggc       780
agttggacag aatacggctc cctggtgggc gccccgatcg agttgggaag c             831

<210> SEQ ID NO 52
<211> LENGTH: 630
<212> TYPE: DNA
<213> ORGANISM: Mycobacterium tuberculosis

<400> SEQUENCE: 52
atgaccaaac ccacatccgc tggccaggcc gacgacgcgc tggttcggct agcccgcgag        60
cgattcgacc tacctgacca ggtacgacgc ctcgcccgcc cgcccgttcc atcgttggag       120
ccgccatacg ggttgcgggt cgcacagctg accgacgcgg agatgttggc ggagtggatg       180
aaccgtcctc atctggcggc ggcctgggag tacgactggc cggcgtcacg ttggcgtcaa       240
cacctgaacg cccaacttga gggaacctat tcgttgccat tgatcggcag ctggcacgga       300
acagatggtg gttatctcga attatactgg gcagcaaagg atttgatttc tcactactac       360
gacgcagacc cctacgattt ggggctgcac gcggccatcg cggacttgtc gaaggtcaat       420
cggggcttcg gcccgctgct gctaccgcgg atcgtggcca gcgtctttgc caacgagccg       480
cgttgccggc ggatcatgtt cgaccccgat caccgcaaca ccgcgacccg tcggttgtgt       540
gagtgggccg gatgcaagtt cctcggtgag catgacacga caaaccggcg catggcgctc       600
tacgctttgg aagctccgac cacggctgcg                                        630

<210> SEQ ID NO 53
<211> LENGTH: 831
<212> TYPE: DNA
<213> ORGANISM: Mycobacterium tuberculosis

<400> SEQUENCE: 53
atggcacgct gcgatgtcct ggtctccgcc gactgggctg agagcaatct gcacgcgccg        60
aaggtcgttt tcgtcgaagt ggacgaggac accagtgcat atgaccgtga ccatattgcc       120

-continued

```
ggcgcgatca agttggactg gcgcaccgac ctgcaggatc cggtcaaacg tgacttcgtc      180
gacgcccagc aattctccaa gctgctgtcc gagcgtggca tcgccaacga ggacacggtg      240
atcctgtacg gcggcaacaa caattggttc gccgcctacg cgtactggta tttcaagctc      300
tacggccatg agaaggtcaa gttgctcgac ggcggccgca agaagtggga gctcgacgga      360
cgcccgctgt ccagcgaccc ggtcagccgg ccggtgacct cctacaccgc ctccccgccg      420
gataacacga ttcgggcatt ccgcgacgag gtcctggcgg ccatcaacgt caagaacctc      480
atcgacgtgc gctctcccga cgagttctcc ggcaagatcc tggcccccgc gcacctgccg      540
caggaacaaa gccagcggcc cggacacatt cctggtgcca tcaacgtgcc gtggagcagg      600
gccgccaacg aggacggcac cttcaagtcc gatgaggagt tggccaagct ttacgccgac      660
gccggcctag acaacagcaa ggaaacgatt gcctactgcc gaatcgggga acggtcctcg      720
cacacctggt tcgtgttgcg ggaattactc ggacaccaaa acgtcaagaa ctacgacggc      780
agttggacag aatacggctc cctggtgggc gccccgatcg agttgggaag c              831
```

<210> SEQ ID NO 54
<211> LENGTH: 585
<212> TYPE: DNA
<213> ORGANISM: Mycobacterium tuberculosis

<400> SEQUENCE: 54

```
gtgagtgacg aggaccgcac ggatcgggcc accgaggacc acaccatctt cgatcgggt       60 gtcggccagc gcgaccagct gcagcggtta tggacccct accggatgaa ctacctggcc      120
gaagcgccag tgaagcgtga ccccaattcc tcggccagcc ctgcgcagcc gttcaccgag      180
atcccgcagc tgtccgacga agagggtctg gtggtcgctc gtggcaagct ggtctacgcc      240
gtgctcaacc tgtacccgta caaccccggg cacttgatgg tggtgcccta tcgtcgggta      300
tccgaactcg aggatctcac cgatttggag agcgccgagt tgatggcgtt cacccagaag      360
gcgattcgcg tgatcaagaa cgtgtcgcgt ccgcacggct tcaatgtcgg cctgaaccta      420
gggacatcgg cggcgggtc gctggccgag cacctgcacg tgcatgtggt gccacggtgg      480
ggtggcgatg cgaatttcat caccatcatc gggggctcca aggtgattcc gcagctgctg      540
cgcgacaccc gtcggctgct tgccaccgag tgggctcggc aacca                    585
```

<210> SEQ ID NO 55
<211> LENGTH: 756
<212> TYPE: DNA
<213> ORGANISM: Mycobacterium tuberculosis

<400> SEQUENCE: 55

```
atgtgcggac ggtttgcggt caccactgat ccggcccagc tggccgagaa aatcacggcc       60
atagacgagg ccaccgggtg cggtggcggg aagacgagtc acaacgtggc acccaccgac      120
acgatcgcga cagtggtgtc ccgccacagc gagcccgacg acgagcccac cgccgggtg      180 cggctcatgc gctggggact gattccgtcg tggatcaagg ccgggcccgg cggcgcaccc      240
gatgccaaag gccaccgct gatcaacgcc cgcgccgata aggtcgccac gtcgccggcg      300
ttccggagtg cggtcagaag taagcgttgc ctggtgccga tggacggctg gtacgaatgg      360 gcgtcgacc ccgacgccac cccggggagg ccgaacgcca agacgccgtt cttcctgcac      420
cgccacgacg gcgccctgtt gttcacggcc gggctgtggt cggtttggaa gtcttacagg      480 tccgcccac cgctgctgag ctgcacggtg atcaccaccg atgccgtggg cgagctggcc      540
```

-continued

| | |
|---|---|
| gagatccatg accggatgcc gctgctgctg gccgaagagg actgggacga ctggctgaat | 600 |
| ccagacgccc cgccggatcc tgagctgctg gcccgcccgc cggatgtgcg cgacatcgcg | 660 |
| ctgcgccaag tgtccacgtt ggtcaacaac gtgcgcaaca cgggcctga gctgttggag | 720 |
| ccggccaggt cgcagcccga gcagatccag ctgctg | 756 |

<210> SEQ ID NO 56
<211> LENGTH: 657
<212> TYPE: DNA
<213> ORGANISM: Mycobacterium tuberculosis

<400> SEQUENCE: 56

| | |
|---|---|
| gtgccagagc tggagacgcc cgacgaccca gagtcgatat accttgcccg cctcgaggat | 60 |
| gtcggagaac acagaccgac gttcacgggc gacatctacc gactcggcga tggtcgcatg | 120 |
| gtgatgatcc tccagcaccc atgcgcgctg cggcacggcg ttgacctcca tccgcgactg | 180 |
| ctggtcgctc ccgtaagacc cgactcgctt cgttccaact gggctagagc cccgttcggc | 240 |
| acgatgccgc ttccgaagct catcgacggt caggatcact cggcggactt catcaatctt | 300 |
| gaactcatcg attcaccaac gcttccgacc tgtgagcgga tcgcggtgct cagccagtca | 360 |
| ggcgtcaact tggtcatgca acggtgggtg taccacagca cccggctcgc cgtgcccacg | 420 |
| cacacctact ccgacagcac cgttggcccg ttcgatgagg cagacctgat cgaggagtgg | 480 |
| gtgacggatc gcgtcgacga tggggccgac ccgcaggcgg ccgaacacga atgcgcctcc | 540 |
| tggctcgatg aaagaatcag cggccgcact cggcgagcgc tgctcagcga ccgtcagcac | 600 |
| gccagttcaa tacggcgaga agcgcgttct catcgaaagt cggtcaagct ggcggac | 657 |

<210> SEQ ID NO 57
<211> LENGTH: 546
<212> TYPE: DNA
<213> ORGANISM: Mycobacterium tuberculosis

<400> SEQUENCE: 57

| | |
|---|---|
| atggcagact gtgattccgt gactaacagc ccccttgcga ccgctaccgc cacgctgcac | 60 |
| actaaccgcg gcgacatcaa gatcgccctg ttcggaaacc atgcgcccaa gaccgtcgcc | 120 |
| aattttgtgg gccttgcgca gggcaccaag gactattcga cccaaaacgc atcaggtggc | 180 |
| ccgtccggcc cgttctacga cggcgcggtc tttcaccggg tgatccaggg cttcatgatc | 240 |
| cagggtggcg atccaaccgg gacgggtcgc ggcggacccg gctacaagtt cgccgacgag | 300 |
| ttccaccccg agctgcaatt cgacaagccc tatctgctcg cgatggccaa cgccggtccg | 360 |
| ggcaccaacg gctcacagtt tttcatcacc gtcggcaaga ctccgcacct gaaccggcgc | 420 |
| cacaccattt tcggtgaagt gatcgacgcg gagtcacagc gggttgtgga ggcgatctcc | 480 |
| aagacggcca ccgacggcaa cgatcggccg acggacccgg tggtgatcga gtcgatcacc | 540 |
| atctcc | 546 |

<210> SEQ ID NO 58
<211> LENGTH: 849
<212> TYPE: DNA
<213> ORGANISM: Mycobacterium tuberculosis

<400> SEQUENCE: 58

| | |
|---|---|
| atgggggcgc agccgttcat cggcagcgag gcgttggcgg cgggactcat cagctggcat | 60 |
| gagctgggca agtactacac cgcgatcatg cccaacgtct atctggacaa gcggctgaag | 120 |
| ccctccctgc ggcaacgcgt tatcgcggcc tggctgtggt cgggccgcaa agggggtgatc | 180 |

```
gccggcgctt cggcatcagc gctgcacggc gcgaaatggg tcgatgacca cgcattggtg    240
gagttgatct ggcgcaacgc cagggcgccg aacggggtgc ggactaagga tgagctactg    300
ctcgacggcg aagtccagcg cttgtgcggg cttactgtga ctaccgttga acgtacggcc    360
ttcgacttgg gcaggcgtcc acccttaggt caggcgataa ccagactgga tgcgcttgcc    420
aatgccaccg atttcaagat caacgatgtt agggagctcg cgaggaagca ccccatact    480 cgcgggctgc gtcaactaga caaggcgctg gatctcgtcg acccaggtgc gcagtcgccg    540
aaggagacgt ggctgcggct cttgctgata acgccggct ttccacggcc gtccactcag    600
atccccttgc tcggcgtcta cgggcatcca agtatttcc tcgacatggg atgggaggac    660
atcatgctcg cggtcgagta cgacggcgag caacaccgtc tcagccgaga ccagttcgtc    720
aaagacgtcg aacgcctgga atacatccgg cgcgccggct ggactcacat cagggtgctg    780
gcagaccaca agggacccga cgtcgtccgc cgggttcggc aggcttggga cacgttgaca    840
tcacgacgt                                                            849

<210> SEQ ID NO 59
<211> LENGTH: 708
<212> TYPE: DNA
<213> ORGANISM: Mycobacterium tuberculosis

<400> SEQUENCE: 59
atgatgcacc gaaccgcact accctcaccg cccgtggcca agcgggtgca gacccgccgg     60
gagcaccacg gcgacgtctt tgtcgaccca tatgaatggt tgcgcgacaa ggacagccct    120
gaagtaatcg cctacctcga agctgaaaac gactacaccg aacggaccac cgcgcacctt    180
gagccattgc ggcaaaagat cttccacgaa atcaaagcgc gtaccaagga aaccgactta    240
tcggtgccga cgcgacgtgg caactggtgg tactacgcgc ggaccttga gggaaagcag     300 tatggcgtac actgtcgttg cccggtaacc gatcccgacg actggaaccc accagagttc    360
gacgagcgca ccgaaatacc cggtgaacag cttctgctcg acgagaacgt ggaagctgac    420
ggccacgact tcttcgcact gggcgcggcc agcgtcagcc tggacgataa cctcttagcg    480
tattccgttg atgtcgtagg tgacgaacga tataccttgc ggttcaagga tttacgcacc    540
ggagaacagt acccggacga gatcgccggg atcggagcgg gagtcacctg gcagctgac    600 aaccactgtc tactacacca ccgtggacgc ggcctggcgt ccggacacag tgtggcgata    660
ccgactaggg tccggcgaat cgtcggagcg ggtttaccac gaagccga                708

<210> SEQ ID NO 60
<211> LENGTH: 729
<212> TYPE: DNA
<213> ORGANISM: Mycobacterium tuberculosis

<400> SEQUENCE: 60
atgcccaatt tctgggcgtt gccgcccgag atcaactcca cccggatata tctcggcccg     60
ggttctggcc cgatactggc cgccgcccag ggatggaacg ctctggccag tgagctggaa    120
aagacgaagg tgggggttgca gtcagcgctc gacacgttgc tggagtcgta tagggggtcag  180 tcgtcgcagg cttttgataca gcagaccttg ccgtatgtgc agtggctgac cacgaccgcc    240
gagcacgccc ataagaccgc gatccagctc acggcagcgc cgaacgccta cgagcaggct    300
agagcggcga tggtgccgcc ggcgatggtg cgcgcgaacc gcgtgcagac cacagtgttg    360
aaggcaatca actggttcgg gcaattctcc accaggatcg ccgacaagga ggccgactac    420
```

| | |
|---|---|
| gaacagatgt ggttccaaga cgcgctagtg atggagaact attgggaagc cgtgcaagag | 480 |
| gcgatacagt cgacgtcgca ttttgaggat ccaccggaga tggccgacga ctacgacgag | 540 |
| gcctggatgc tcaacaccgt gttcgactat cacaacgaga acgcaaaaga ggaggtcatc | 600 |
| catctcgtgc ccgacgtgaa caaggagagg gggcccatcg aactcgtaac caaggtagac | 660 |
| aaagagggga ccatcagact cgtctacgat ggggagccca cgttttcata caaggaacat | 720 |
| cctaagttt | 729 |

<210> SEQ ID NO 61
<211> LENGTH: 561
<212> TYPE: DNA
<213> ORGANISM: Mycobacterium tuberculosis

<400> SEQUENCE: 61

| | |
|---|---|
| atggccgacg ctgacaccac cgacttcgac gtcgacgcag aagcaccggg tggaggcgtc | 60 |
| cgggaggaca cggcgacgga tgctgacgag gccgacgatc aagaagagag attggtcgcc | 120 |
| gagggcgaga ttgcaggcga ctacctggaa gagttattgg acgtgttgga cttcgatggc | 180 |
| gacatcgacc tcgatgtcga aggcaatcgt gcggtggtga gcatcgacgg cagtgacgac | 240 |
| ctgaacaagt tggtcgggcg cgggggcgag gtgctcgacg ctctgcagga actcacccgg | 300 |
| ttggcggtgc atcagaagac cggtgtgcgg agccggttga tgctagacat cgcgaggtgg | 360 |
| cgacggcgc gccgggagga attggcggcg ctggccgacg aggtggcgcg gcgagtggcc | 420 |
| gaaaccggtg accgcgagga actcgttcca atgacgccgt tcgaacggaa gatcgtccac | 480 |
| gatgcggttg cagcggtgcc aggtgtgcac agcgaaagcg aaggcgtgga gccagaacgc | 540 |
| cgagtcgttg tgctccgcga c | 561 |

<210> SEQ ID NO 62
<211> LENGTH: 621
<212> TYPE: DNA
<213> ORGANISM: Mycobacterium tuberculosis

<400> SEQUENCE: 62

| | |
|---|---|
| ttgtgtgcaa aaccgtatct aattgatacg attgcgcaca tggctatctg ggatcgcctc | 60 |
| gtcgaggttg ccgccgagca acatggctac gtcacgactc gcgatgcgcg agacatcggc | 120 |
| gtcgaccctg tgcagctccg cctcctagcg gggcgcggac gtcttgagcg tgtcggccga | 180 |
| ggtgtgtacc gggtgcccgt gctgccgcgt ggtgagcacg acgatctcgc agccgcagtg | 240 |
| tcgtggactt tggggcgtgg cgttatctcg catgagtcgg ccttggcgct tcatgccctc | 300 |
| gctgacgtga acccgtcgcg catccatctc accgtcccgc gcaacaacca tccgcgtgcg | 360 |
| gccggggggcg agctgtaccg agttcaccgc cgcgacctcc aggcagccca cgtcacttcg | 420 |
| gtcgacggaa tacccgtcac gacggttgcg cgcaccatca agactgcgt gaagacgggc | 480 |
| acggatcctt atcagcttcg ggccgcgatc gagcgagccg aagccgaggg cacgcttcgt | 540 |
| cgtgggtcag cagctgagct acgcgctgcg ctcgatgaga ccactgccgg attacgcgct | 600 |
| cggccgaagc gagcatcggc g | 621 |

<210> SEQ ID NO 63
<211> LENGTH: 555
<212> TYPE: DNA
<213> ORGANISM: Mycobacterium tuberculosis

<400> SEQUENCE: 63

| | |
|---|---|
| atgattgatg aggctctctt cgacgccgaa gagaaaatgg agaaggctgt ggcggtggca | 60 |

```
cgtgacgacc tgtcaactat ccgtaccggc cgcgccaacc ctggcatgtt ctctcggatc      120
accatcgact actacggtgc ggccacccccg atcacgcaac tggccagcat caatgtcccc     180
gaggcgcggc tagtcgtgat aaagccgtat gaagccaatc agttgcgcgc tatcgagact     240
gcaattcgca actccgacct tggagtgaat cccaccaacg acggcgccct tattcgcgtg     300
gccgtaccgc agctcaccga gaacgtcggc gagagctgg tcaaacaggc aaagcataag      360
ggggaggagg ccaaggtttc ggtgcgtaat atccgtcgca aagcgatgga ggaactccat     420
cgcatccgta aggaaggcga ggccggcgag gatgaggtcg gtcgcgcaga aaaggatctc    480
gacaagacca cgcaccaata cgtcacccaa attgatgagc tggttaaaca caagaaggc     540 gagctgctgg aggtc                                                     555

<210> SEQ ID NO 64
<211> LENGTH: 498
<212> TYPE: DNA
<213> ORGANISM: Mycobacterium tuberculosis

<400> SEQUENCE: 64
atgcccaagc tcagcgcggg tgtgctgctg tatcgggcgc gcgccggtgt cgtcgacgtc      60
cttctggcgc atccgggcgg cccgttttgg gcgggaaagg acgacggcgc ttggtcgatc     120
ccgaagggcg aatacaccgg cggcgaagat ccgtggctgg ccgcccggcg cgagttctcc     180
gaggagatcg ggttgtgcgt gcctgacggg ccgcgaatcg acttcgggtc gctgaaacag     240
tccggcggca agtggtgac cgtgttcggt gtccgggcgg atctggacat caccgacgca      300
cgaagcagca ccttcgaatt ggactggccg aagggctcgg gcaagatgcg taagttcccc     360
gaggtcgacc gggtgagctg gtttccggta gcgcgggcac gcaccaaact gctcaagggg     420
cagcggggtt ttctcgaccg gttgatggcg caccccggccg tggcgggttt gtctgaagga    480
ccagaatccc tgcctcgc                                                   498

<210> SEQ ID NO 65
<211> LENGTH: 144
<212> TYPE: PRT
<213> ORGANISM: Mycobacterium tuberculosis

<400> SEQUENCE: 65

Met Ala Thr Thr Leu Pro Val Gln Arg His Pro Arg Ser Leu Phe Pro
 1               5                  10                  15

Glu Phe Ser Glu Leu Phe Ala Ala Phe Pro Ser Phe Ala Gly Leu Arg
            20                  25                  30

Pro Thr Phe Asp Thr Arg Leu Met Arg Leu Glu Asp Glu Met Lys Glu
        35                  40                  45

Gly Arg Tyr Glu Val Arg Ala Glu Leu Pro Gly Val Asp Pro Asp Lys
    50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp
                100                 105                 110

Ile Lys Ala Thr Tyr Asp Lys Gly Ile Leu Thr Val Ser Val Ala Val
        115                 120                 125

Ser Glu Gly Lys Pro Thr Glu Lys His Ile Gln Ile Arg Ser Thr Asn
    130                 135                 140
```

<210> SEQ ID NO 66
<211> LENGTH: 159
<212> TYPE: PRT
<213> ORGANISM: Mycobacterium tuberculosis

<400> SEQUENCE: 66

Val Lys Arg Gly Leu Thr Val Ala Val Ala Gly Ala Ile Leu Val
1               5                   10                  15

Ala Gly Leu Ser Gly Cys Ser Ser Asn Lys Ser Thr Thr Gly Ser Gly
            20                  25                  30

Glu Thr Thr Thr Ala Ala Gly Thr Ala Ser Pro Gly Ala Ala Ser
            35                  40                  45

Gly Pro Lys Val Val Ile Asp Gly Lys Asp Gln Asn Val Thr Gly Ser
        50                  55                  60

Val Val Cys Thr Thr Ala Ala Gly Asn Val Asn Ile Ala Ile Gly Gly
65                  70                  75                  80

Ala Ala Thr Gly Ile Ala Ala Val Leu Thr Asp Gly Asn Pro Pro Glu
                85                  90                  95

Val Lys Ser Val Gly Leu Gly Asn Val Asn Gly Val Thr Leu Gly Tyr
            100                 105                 110

Thr Ser Gly Thr Gly Gln Gly Asn Ala Ser Ala Thr Lys Asp Gly Ser
        115                 120                 125

His Tyr Lys Ile Thr Gly Thr Ala Thr Gly Val Asp Met Ala Asn Pro
    130                 135                 140

Met Ser Pro Val Asn Lys Ser Phe Glu Ile Glu Val Thr Cys Ser
145                 150                 155

<210> SEQ ID NO 67
<211> LENGTH: 270
<212> TYPE: PRT
<213> ORGANISM: Mycobacterium tuberculosis

<400> SEQUENCE: 67

Met Ala Asn Pro Phe Val Lys Ala Trp Lys Tyr Leu Met Ala Leu Phe
1               5                   10                  15

Ser Ser Lys Ile Asp Glu His Ala Asp Pro Lys Val Gln Ile Gln Gln
            20                  25                  30

Ala Ile Glu Glu Ala Gln Arg Thr His Gln Ala Leu Thr Gln Gln Ala
        35                  40                  45

Ala Gln Val Ile Gly Asn Gln Arg Gln Leu Glu Met Arg Leu Asn Arg
    50                  55                  60

Gln Leu Ala Asp Ile Glu Lys Leu Gln Val Asn Val Arg Gln Ala Leu
65                  70                  75                  80

Thr Leu Ala Asp Gln Ala Thr Ala Ala Gly Asp Ala Ala Lys Ala Thr
                85                  90                  95

Glu Tyr Asn Asn Ala Ala Glu Ala Phe Ala Ala Gln Leu Val Thr Ala
            100                 105                 110

Glu Gln Ser Val Glu Asp Leu Lys Thr Leu His Asp Gln Ala Leu Ser
        115                 120                 125

Ala Ala Ala Gln Ala Lys Lys Ala Val Glu Arg Asn Ala Met Val Leu
    130                 135                 140

Gln Gln Lys Ile Ala Glu Arg Thr Lys Leu Leu Ser Gln Leu Glu Gln
145                 150                 155                 160

Ala Lys Met Gln Glu Gln Val Ser Ala Ser Leu Arg Ser Met Ser Glu
                165                 170                 175

-continued

Leu Ala Ala Pro Gly Asn Thr Pro Ser Leu Asp Glu Val Arg Asp Lys
                180                 185                 190

Ile Glu Arg Arg Tyr Ala Asn Ala Ile Gly Ser Ala Glu Leu Ala Glu
            195                 200                 205

Ser Ser Val Gln Gly Arg Met Leu Glu Val Glu Gln Ala Gly Ile Gln
        210                 215                 220

Met Ala Gly His Ser Arg Leu Glu Gln Ile Arg Ala Ser Met Arg Gly
225                 230                 235                 240

Glu Ala Leu Pro Ala Gly Gly Thr Thr Ala Thr Pro Arg Pro Ala Thr
                245                 250                 255

Glu Thr Ser Gly Gly Ala Ile Ala Glu Gln Pro Tyr Gly Gln
            260                 265                 270

<210> SEQ ID NO 68
<211> LENGTH: 289
<212> TYPE: PRT
<213> ORGANISM: Mycobacterium tuberculosis

<400> SEQUENCE: 68

Met Thr Leu Lys Val Lys Gly Glu Gly Leu Gly Ala Gln Val Thr Gly
1               5                   10                  15

Val Asp Pro Lys Asn Leu Asp Asp Ile Thr Thr Asp Glu Ile Arg Asp
            20                  25                  30

Ile Val Tyr Thr Asn Lys Leu Val Leu Lys Asp Val His Pro Ser
        35                  40                  45

Pro Arg Glu Phe Ile Lys Leu Gly Arg Ile Ile Gly Gln Ile Val Pro
    50                  55                  60

Tyr Tyr Glu Pro Met Tyr His His Glu Asp His Pro Glu Ile Phe Val
65                  70                  75                  80

Ser Ser Thr Glu Glu Gly Gln Gly Val Pro Lys Thr Gly Ala Phe Trp
                85                  90                  95

His Ile Asp Tyr Met Phe Met Pro Glu Pro Phe Ala Phe Ser Met Val
            100                 105                 110

Leu Pro Leu Ala Val Pro Gly His Asp Arg Gly Thr Tyr Phe Ile Asp
        115                 120                 125

Leu Ala Arg Val Trp Gln Ser Leu Pro Ala Ala Lys Arg Asp Pro Ala
130                 135                 140

Arg Gly Thr Val Ser Thr His Asp Pro Arg Arg His Ile Lys Ile Arg
145                 150                 155                 160

Pro Ser Asp Val Tyr Arg Pro Ile Gly Glu Val Trp Asp Glu Ile Asn
                165                 170                 175

Arg Thr Thr Pro Pro Ile Lys Trp Pro Thr Val Ile Arg His Pro Lys
            180                 185                 190

Thr Gly Gln Glu Ile Leu Tyr Ile Cys Ala Thr Gly Thr Thr Lys Ile
        195                 200                 205

Glu Asp Lys Asp Gly Asn Pro Val Asp Pro Glu Val Leu Gln Glu Leu
210                 215                 220

Met Ala Ala Thr Gly Gln Leu Asp Pro Glu Tyr Gln Ser Pro Phe Ile
225                 230                 235                 240

His Thr Gln His Tyr Gln Val Gly Asp Ile Ile Leu Trp Asp Asn Arg
                245                 250                 255

Val Leu Met His Arg Ala Lys His Gly Ser Ala Ala Gly Thr Leu Thr
            260                 265                 270

Thr Tyr Arg Leu Thr Met Leu Asp Gly Leu Lys Thr Pro Gly Tyr Ala

Ala

<210> SEQ ID NO 69
<211> LENGTH: 199
<212> TYPE: PRT
<213> ORGANISM: Mycobacterium tuberculosis

<400> SEQUENCE: 69

Met Ala Glu Asn Ser Asn Ile Asp Asp Ile Lys Ala Pro Leu Leu Ala
1               5                   10                  15

Ala Leu Gly Ala Ala Asp Leu Ala Leu Ala Thr Val Asn Glu Leu Ile
            20                  25                  30

Thr Asn Leu Arg Glu Arg Ala Glu Glu Thr Arg Thr Asp Thr Arg Ser
        35                  40                  45

Arg Val Glu Glu Ser Arg Ala Arg Leu Thr Lys Leu Gln Glu Asp Leu
    50                  55                  60

Pro Glu Gln Leu Thr Glu Leu Arg Glu Lys Phe Thr Ala Glu Glu Leu
65                  70                  75                  80

Arg Lys Ala Ala Glu Gly Tyr Leu Glu Ala Ala Thr Ser Arg Tyr Asn
                85                  90                  95

Glu Leu Val Glu Arg Gly Glu Ala Ala Leu Glu Arg Leu Arg Ser Gln
            100                 105                 110

Gln Ser Phe Glu Glu Val Ser Ala Arg Ala Glu Gly Tyr Val Asp Gln
        115                 120                 125

Ala Val Glu Leu Thr Gln Glu Ala Leu Gly Thr Val Ala Ser Gln Thr
    130                 135                 140

Arg Ala Val Gly Glu Arg Ala Ala Lys Leu Val Gly Ile Glu Leu Pro
145                 150                 155                 160

Lys Lys Ala Ala Pro Ala Lys Lys Ala Ala Pro Ala Lys Lys Ala Ala
                165                 170                 175

Pro Ala Lys Lys Ala Ala Lys Lys Ala Pro Ala Lys Lys Ala Ala
        180                 185                 190

Ala Lys Lys Val Thr Gln Lys
        195

<210> SEQ ID NO 70
<211> LENGTH: 277
<212> TYPE: PRT
<213> ORGANISM: Mycobacterium tuberculosis

<400> SEQUENCE: 70

Met Ala Arg Cys Asp Val Leu Val Ser Ala Asp Trp Ala Glu Ser Asn
1               5                   10                  15

Leu His Ala Pro Lys Val Val Phe Val Glu Val Asp Glu Asp Thr Ser
            20                  25                  30

Ala Tyr Asp Arg Asp His Ile Ala Gly Ala Ile Lys Leu Asp Trp Arg
        35                  40                  45

Thr Asp Leu Gln Asp Pro Val Lys Arg Asp Phe Val Asp Ala Gln Gln
    50                  55                  60

Phe Ser Lys Leu Leu Ser Glu Arg Gly Ile Ala Asn Glu Asp Thr Val
65                  70                  75                  80

Ile Leu Tyr Gly Gly Asn Asn Asn Trp Phe Ala Ala Tyr Ala Tyr Trp
                85                  90                  95

Tyr Phe Lys Leu Tyr Gly His Glu Lys Val Lys Leu Leu Asp Gly Gly
            100                 105                 110

Arg Lys Lys Trp Glu Leu Asp Gly Arg Pro Leu Ser Ser Asp Pro Val
    115                 120                 125

Ser Arg Pro Val Thr Ser Tyr Thr Ala Ser Pro Pro Asp Asn Thr Ile
130                 135                 140

Arg Ala Phe Arg Asp Glu Val Leu Ala Ala Ile Asn Val Lys Asn Leu
145                 150                 155                 160

Ile Asp Val Arg Ser Pro Asp Glu Phe Ser Gly Lys Ile Leu Ala Pro
                165                 170                 175

Ala His Leu Pro Gln Glu Gln Ser Gln Arg Pro Gly His Ile Pro Gly
            180                 185                 190

Ala Ile Asn Val Pro Trp Ser Arg Ala Ala Asn Glu Asp Gly Thr Phe
        195                 200                 205

Lys Ser Asp Glu Glu Leu Ala Lys Leu Tyr Ala Asp Ala Gly Leu Asp
    210                 215                 220

Asn Ser Lys Glu Thr Ile Ala Tyr Cys Arg Ile Gly Glu Arg Ser Ser
225                 230                 235                 240

His Thr Trp Phe Val Leu Arg Glu Leu Leu Gly His Gln Asn Val Lys
                245                 250                 255

Asn Tyr Asp Gly Ser Trp Thr Glu Tyr Gly Ser Leu Val Gly Ala Pro
            260                 265                 270

Ile Glu Leu Gly Ser
            275

<210> SEQ ID NO 71
<211> LENGTH: 210
<212> TYPE: PRT
<213> ORGANISM: Mycobacterium tuberculosis

<400> SEQUENCE: 71

Met Thr Lys Pro Thr Ser Ala Gly Gln Ala Asp Asp Ala Leu Val Arg
1               5                   10                  15

Leu Ala Arg Glu Arg Phe Asp Leu Pro Asp Gln Val Arg Arg Leu Ala
            20                  25                  30

Arg Pro Pro Val Pro Ser Leu Glu Pro Pro Tyr Gly Leu Arg Val Ala
        35                  40                  45

Gln Leu Thr Asp Ala Glu Met Leu Ala Glu Trp Met Asn Arg Pro His
50                  55                  60

Leu Ala Ala Ala Trp Glu Tyr Asp Trp Pro Ala Ser Arg Trp Arg Gln
65                  70                  75                  80

His Leu Asn Ala Gln Leu Glu Gly Thr Tyr Ser Leu Pro Leu Ile Gly
                85                  90                  95

Ser Trp His Gly Thr Asp Gly Gly Tyr Leu Glu Leu Tyr Trp Ala Ala
            100                 105                 110

Lys Asp Leu Ile Ser His Tyr Tyr Asp Ala Asp Pro Tyr Asp Leu Gly
        115                 120                 125

Leu His Ala Ala Ile Ala Asp Leu Ser Lys Val Asn Arg Gly Phe Gly
    130                 135                 140

Pro Leu Leu Leu Pro Arg Ile Val Ala Ser Val Phe Ala Asn Glu Pro
145                 150                 155                 160

Arg Cys Arg Arg Ile Met Phe Asp Pro Asp His Arg Asn Thr Ala Thr
                165                 170                 175

Arg Arg Leu Cys Glu Trp Ala Gly Cys Lys Phe Leu Gly Glu His Asp
            180                 185                 190

Thr Thr Asn Arg Arg Met Ala Leu Tyr Ala Leu Glu Ala Pro Thr Thr

```
                195                 200                 205
Ala Ala
    210

<210> SEQ ID NO 72
<211> LENGTH: 277
<212> TYPE: PRT
<213> ORGANISM: Mycobacterium tuberculosis

<400> SEQUENCE: 72

Met Ala Arg Cys Asp Val Leu Val Ser Ala Asp Trp Ala Glu Ser Asn
 1               5                  10                  15

Leu His Ala Pro Lys Val Val Phe Val Glu Val Asp Glu Asp Thr Ser
            20                  25                  30

Ala Tyr Asp Arg Asp His Ile Ala Gly Ala Ile Lys Leu Asp Trp Arg
        35                  40                  45

Thr Asp Leu Gln Asp Pro Val Lys Arg Asp Phe Val Asp Ala Gln Gln
    50                  55                  60

Phe Ser Lys Leu Leu Ser Glu Arg Gly Ile Ala Asn Glu Asp Thr Val
65                  70                  75                  80

Ile Leu Tyr Gly Gly Asn Asn Asn Trp Phe Ala Ala Tyr Ala Tyr Trp
                85                  90                  95

Tyr Phe Lys Leu Tyr Gly His Glu Lys Val Lys Leu Leu Asp Gly Gly
            100                 105                 110

Arg Lys Lys Trp Glu Leu Asp Gly Arg Pro Leu Ser Ser Asp Pro Val
        115                 120                 125

Ser Arg Pro Val Thr Ser Tyr Thr Ala Ser Pro Asp Asn Thr Ile
    130                 135                 140

Arg Ala Phe Arg Asp Glu Val Leu Ala Ala Ile Asn Val Lys Asn Leu
145                 150                 155                 160

Ile Asp Val Arg Ser Pro Asp Glu Phe Ser Gly Lys Ile Leu Ala Pro
                165                 170                 175

Ala His Leu Pro Gln Glu Gln Ser Gln Arg Pro Gly His Ile Pro Gly
            180                 185                 190

Ala Ile Asn Val Pro Trp Ser Arg Ala Ala Asn Glu Asp Gly Thr Phe
        195                 200                 205

Lys Ser Asp Glu Glu Leu Ala Lys Leu Tyr Ala Asp Ala Gly Leu Asp
    210                 215                 220

Asn Ser Lys Glu Thr Ile Ala Tyr Cys Arg Ile Gly Glu Arg Ser Ser
225                 230                 235                 240

His Thr Trp Phe Val Leu Arg Glu Leu Leu Gly His Gln Asn Val Lys
                245                 250                 255

Asn Tyr Asp Gly Ser Trp Thr Glu Tyr Gly Ser Leu Val Gly Ala Pro
            260                 265                 270

Ile Glu Leu Gly Ser
        275

<210> SEQ ID NO 73
<211> LENGTH: 195
<212> TYPE: PRT
<213> ORGANISM: Mycobacterium tuberculosis

<400> SEQUENCE: 73

Val Ser Asp Glu Asp Arg Thr Asp Arg Ala Thr Glu Asp His Thr Ile
 1               5                  10                  15

Phe Asp Arg Gly Val Gly Gln Arg Asp Gln Leu Gln Arg Leu Trp Thr
```

```
                20                  25                  30
Pro Tyr Arg Met Asn Tyr Leu Ala Glu Ala Pro Val Lys Arg Asp Pro
            35                  40                  45

Asn Ser Ser Ala Ser Pro Ala Gln Pro Phe Thr Glu Ile Pro Gln Leu
        50                  55                  60

Ser Asp Glu Gly Leu Val Val Ala Arg Gly Lys Leu Val Tyr Ala
65                  70                  75                  80

Val Leu Asn Leu Tyr Pro Tyr Asn Pro Gly His Leu Met Val Val Pro
                85                  90                  95

Tyr Arg Arg Val Ser Glu Leu Gly Asp Leu Thr Asp Leu Glu Ser Ala
            100                 105                 110

Glu Leu Met Ala Phe Thr Gln Lys Ala Ile Arg Val Ile Lys Asn Val
            115                 120                 125

Ser Arg Pro His Gly Phe Asn Val Gly Leu Asn Leu Gly Thr Ser Ala
            130                 135                 140

Gly Gly Ser Leu Ala Glu His Leu His Val His Val Val Pro Arg Trp
145                 150                 155                 160

Gly Gly Asp Ala Asn Phe Ile Thr Ile Ile Gly Gly Ser Lys Val Ile
                165                 170                 175

Pro Gln Leu Leu Arg Asp Thr Arg Arg Leu Leu Ala Thr Glu Trp Ala
            180                 185                 190

Arg Gln Pro
        195

<210> SEQ ID NO 74
<211> LENGTH: 252
<212> TYPE: PRT
<213> ORGANISM: Mycobacterium tuberculosis

<400> SEQUENCE: 74

Met Cys Gly Arg Phe Ala Val Thr Thr Asp Pro Ala Gln Leu Ala Glu
1               5                   10                  15

Lys Ile Thr Ala Ile Asp Glu Ala Thr Gly Cys Gly Gly Gly Lys Thr
            20                  25                  30

Ser Tyr Asn Val Ala Pro Thr Asp Thr Ile Ala Thr Val Val Ser Arg
        35                  40                  45

His Ser Glu Pro Asp Asp Glu Pro Thr Arg Arg Val Arg Leu Met Arg
    50                  55                  60

Trp Gly Leu Ile Pro Ser Trp Ile Lys Ala Gly Pro Gly Gly Ala Pro
65                  70                  75                  80

Asp Ala Lys Gly Pro Pro Leu Ile Asn Ala Arg Ala Asp Lys Val Ala
                85                  90                  95

Thr Ser Pro Ala Phe Arg Ser Ala Val Arg Ser Lys Arg Cys Leu Val
            100                 105                 110

Pro Met Asp Gly Trp Tyr Glu Trp Arg Val Asp Pro Asp Ala Thr Pro
            115                 120                 125

Gly Arg Pro Asn Ala Lys Thr Pro Phe Phe Leu His Arg His Asp Gly
            130                 135                 140

Ala Leu Leu Phe Thr Ala Gly Leu Trp Ser Val Trp Lys Ser Tyr Arg
145                 150                 155                 160

Ser Ala Pro Pro Leu Leu Ser Cys Thr Val Ile Thr Thr Asp Ala Val
                165                 170                 175

Gly Glu Leu Ala Glu Ile His Asp Arg Met Pro Leu Leu Leu Ala Glu
            180                 185                 190
```

```
Glu Asp Trp Asp Asp Trp Leu Asn Pro Asp Ala Pro Pro Asp Pro Glu
        195                 200                 205

Leu Leu Ala Arg Pro Pro Asp Val Arg Asp Ile Ala Leu Arg Gln Val
    210                 215                 220

Ser Thr Leu Val Asn Asn Val Arg Asn Asn Gly Pro Glu Leu Leu Glu
225                 230                 235                 240

Pro Ala Arg Ser Gln Pro Glu Gln Ile Gln Leu Leu
            245                 250

<210> SEQ ID NO 75
<211> LENGTH: 219
<212> TYPE: PRT
<213> ORGANISM: Mycobacterium tuberculosis

<400> SEQUENCE: 75

Val Pro Glu Leu Glu Thr Pro Asp Asp Pro Glu Ser Ile Tyr Leu Ala
1               5                   10                  15

Arg Leu Glu Asp Val Gly Glu His Arg Pro Thr Phe Thr Gly Asp Ile
            20                  25                  30

Tyr Arg Leu Gly Asp Gly Arg Met Val Met Ile Leu Gln His Pro Cys
        35                  40                  45

Ala Leu Arg His Gly Val Asp Leu His Pro Arg Leu Leu Val Ala Pro
    50                  55                  60

Val Arg Pro Asp Ser Leu Arg Ser Asn Trp Ala Arg Ala Pro Phe Gly
65                  70                  75                  80

Thr Met Pro Leu Pro Lys Leu Ile Asp Gly Gln Asp His Ser Ala Asp
                85                  90                  95

Phe Ile Asn Leu Glu Leu Ile Asp Ser Pro Thr Leu Pro Thr Cys Glu
            100                 105                 110

Arg Ile Ala Val Leu Ser Gln Ser Gly Val Asn Leu Val Met Gln Arg
        115                 120                 125

Trp Val Tyr His Ser Thr Arg Leu Ala Val Pro Thr His Thr Tyr Ser
    130                 135                 140

Asp Ser Thr Val Gly Pro Phe Asp Glu Ala Asp Leu Ile Glu Glu Trp
145                 150                 155                 160

Val Thr Asp Arg Val Asp Asp Gly Ala Asp Pro Gln Ala Ala Glu His
                165                 170                 175

Glu Cys Ala Ser Trp Leu Asp Glu Arg Ile Ser Gly Arg Thr Arg Arg
            180                 185                 190

Ala Leu Leu Ser Asp Arg Gln His Ala Ser Ser Ile Arg Arg Glu Ala
        195                 200                 205

Arg Ser His Arg Lys Ser Val Lys Leu Ala Asp
    210                 215

<210> SEQ ID NO 76
<211> LENGTH: 182
<212> TYPE: PRT
<213> ORGANISM: Mycobacterium tuberculosis

<400> SEQUENCE: 76

Met Ala Asp Cys Asp Ser Val Thr Asn Ser Pro Leu Ala Thr Ala Thr
1               5                   10                  15

Ala Thr Leu His Thr Asn Arg Gly Asp Ile Lys Ile Ala Leu Phe Gly
            20                  25                  30

Asn His Ala Pro Lys Thr Val Ala Asn Phe Val Gly Leu Ala Gln Gly
        35                  40                  45
```

```
Thr Lys Asp Tyr Ser Thr Gln Asn Ala Ser Gly Gly Pro Ser Gly Pro
 50                  55                  60

Phe Tyr Asp Gly Ala Val Phe His Arg Val Ile Gln Gly Phe Met Ile
 65                  70                  75                  80

Gln Gly Gly Asp Pro Thr Gly Thr Gly Arg Gly Gly Pro Gly Tyr Lys
                 85                  90                  95

Phe Ala Asp Glu Phe His Pro Glu Leu Gln Phe Asp Lys Pro Tyr Leu
                100                 105                 110

Leu Ala Met Ala Asn Ala Gly Pro Gly Thr Asn Gly Ser Gln Phe Phe
                115                 120                 125

Ile Thr Val Gly Lys Thr Pro His Leu Asn Arg Arg His Thr Ile Phe
130                 135                 140

Gly Glu Val Ile Asp Ala Glu Ser Gln Arg Val Val Glu Ala Ile Ser
145                 150                 155                 160

Lys Thr Ala Thr Asp Gly Asn Asp Arg Pro Thr Asp Pro Val Val Ile
                165                 170                 175

Glu Ser Ile Thr Ile Ser
                180

<210> SEQ ID NO 77
<211> LENGTH: 283
<212> TYPE: PRT
<213> ORGANISM: Mycobacterium tuberculosis

<400> SEQUENCE: 77

Met Gly Ala Gln Pro Phe Ile Gly Ser Glu Ala Leu Ala Ala Gly Leu
 1                5                  10                  15

Ile Ser Trp His Glu Leu Gly Lys Tyr Tyr Thr Ala Ile Met Pro Asn
                 20                  25                  30

Val Tyr Leu Asp Lys Arg Leu Lys Pro Ser Leu Arg Gln Arg Val Ile
                 35                  40                  45

Ala Ala Trp Leu Trp Ser Gly Arg Lys Gly Val Ile Ala Gly Ala Ser
 50                  55                  60

Ala Ser Ala Leu His Gly Ala Lys Trp Val Asp Asp His Ala Leu Val
 65                  70                  75                  80

Glu Leu Ile Trp Arg Asn Ala Arg Ala Pro Asn Gly Val Arg Thr Lys
                 85                  90                  95

Asp Glu Leu Leu Leu Asp Gly Glu Val Gln Arg Leu Cys Gly Leu Thr
                100                 105                 110

Val Thr Thr Val Glu Arg Thr Ala Phe Asp Leu Gly Arg Arg Pro Pro
                115                 120                 125

Leu Gly Gln Ala Ile Thr Arg Leu Asp Ala Leu Ala Asn Ala Thr Asp
130                 135                 140

Phe Lys Ile Asn Asp Val Arg Glu Leu Ala Arg Lys His Pro His Thr
145                 150                 155                 160

Arg Gly Leu Arg Gln Leu Asp Lys Ala Leu Asp Leu Val Asp Pro Gly
                165                 170                 175

Ala Gln Ser Pro Lys Glu Thr Trp Leu Arg Leu Leu Ile Asn Ala
                180                 185                 190

Gly Phe Pro Arg Pro Ser Thr Gln Ile Pro Leu Leu Gly Val Tyr Gly
                195                 200                 205

His Pro Lys Tyr Phe Leu Asp Met Gly Trp Glu Asp Ile Met Leu Ala
                210                 215                 220

Val Glu Tyr Asp Gly Glu Gln His Arg Leu Ser Arg Asp Gln Phe Val
225                 230                 235                 240
```

```
Lys Asp Val Glu Arg Leu Glu Tyr Ile Arg Arg Ala Gly Trp Thr His
                245                 250                 255

Ile Arg Val Leu Ala Asp His Lys Gly Pro Asp Val Val Arg Arg Val
            260                 265                 270

Arg Gln Ala Trp Asp Thr Leu Thr Ser Arg Arg
        275                 280

<210> SEQ ID NO 78
<211> LENGTH: 236
<212> TYPE: PRT
<213> ORGANISM: Mycobacterium tuberculosis

<400> SEQUENCE: 78

Met Met His Arg Thr Ala Leu Pro Ser Pro Val Ala Lys Arg Val
  1               5                  10                  15

Gln Thr Arg Arg Glu His His Gly Asp Val Phe Val Asp Pro Tyr Glu
                20                  25                  30

Trp Leu Arg Asp Lys Asp Ser Pro Glu Val Ile Ala Tyr Leu Glu Ala
            35                  40                  45

Glu Asn Asp Tyr Thr Glu Arg Thr Thr Ala His Leu Glu Pro Leu Arg
 50                  55                  60

Gln Lys Ile Phe His Glu Ile Lys Ala Arg Thr Lys Glu Thr Asp Leu
65                  70                  75                  80

Ser Val Pro Thr Arg Arg Gly Asn Trp Trp Tyr Tyr Ala Arg Thr Phe
                85                  90                  95

Glu Gly Lys Gln Tyr Gly Val His Cys Arg Cys Pro Val Thr Asp Pro
            100                 105                 110

Asp Asp Trp Asn Pro Pro Glu Phe Asp Glu Arg Thr Glu Ile Pro Gly
        115                 120                 125

Glu Gln Leu Leu Leu Asp Glu Asn Val Glu Ala Asp Gly His Asp Phe
    130                 135                 140

Phe Ala Leu Gly Ala Ala Ser Val Ser Leu Asp Asp Asn Leu Leu Ala
145                 150                 155                 160

Tyr Ser Val Asp Val Val Gly Asp Glu Arg Tyr Thr Leu Arg Phe Lys
                165                 170                 175

Asp Leu Arg Thr Gly Glu Gln Tyr Pro Asp Glu Ile Ala Gly Ile Gly
            180                 185                 190

Ala Gly Val Thr Trp Ala Ala Asp Asn His Cys Leu Leu His His Arg
        195                 200                 205

Gly Arg Gly Leu Ala Ser Gly His Ser Val Ala Ile Pro Thr Arg Val
    210                 215                 220

Arg Arg Ile Val Gly Ala Gly Leu Pro Arg Ser Arg
225                 230                 235

<210> SEQ ID NO 79
<211> LENGTH: 243
<212> TYPE: PRT
<213> ORGANISM: Mycobacterium tuberculosis

<400> SEQUENCE: 79

Met Pro Asn Phe Trp Ala Leu Pro Pro Glu Ile Asn Ser Thr Arg Ile
  1               5                  10                  15

Tyr Leu Gly Pro Gly Ser Gly Pro Ile Leu Ala Ala Ala Gln Gly Trp
                20                  25                  30

Asn Ala Leu Ala Ser Glu Leu Glu Lys Thr Lys Val Gly Leu Gln Ser
            35                  40                  45
```

```
Ala Leu Asp Thr Leu Leu Glu Ser Tyr Arg Gly Gln Ser Gln Ala
         50                  55                  60

Leu Ile Gln Gln Thr Leu Pro Tyr Val Gln Trp Leu Thr Thr Thr Ala
 65                  70                  75                  80

Glu His Ala His Lys Thr Ala Ile Gln Leu Thr Ala Ala Asn Ala
                 85                  90                  95

Tyr Glu Gln Ala Arg Ala Ala Met Val Pro Pro Ala Met Val Arg Ala
                100                 105                 110

Asn Arg Val Gln Thr Thr Val Leu Lys Ala Ile Asn Trp Phe Gly Gln
                115                 120                 125

Phe Ser Thr Arg Ile Ala Asp Lys Glu Ala Asp Tyr Glu Gln Met Trp
    130                 135                 140

Phe Gln Asp Ala Leu Val Met Glu Asn Tyr Trp Glu Ala Val Gln Glu
145                 150                 155                 160

Ala Ile Gln Ser Thr Ser His Phe Glu Asp Pro Pro Glu Met Ala Asp
                165                 170                 175

Asp Tyr Asp Glu Ala Trp Met Leu Asn Thr Val Phe Asp Tyr His Asn
                180                 185                 190

Glu Asn Ala Lys Glu Glu Val Ile His Leu Val Pro Asp Val Asn Lys
                195                 200                 205

Glu Arg Gly Pro Ile Glu Leu Val Thr Lys Val Asp Lys Glu Gly Thr
    210                 215                 220

Ile Arg Leu Val Tyr Asp Gly Glu Pro Thr Phe Ser Tyr Lys Glu His
225                 230                 235                 240

Pro Lys Phe

<210> SEQ ID NO 80
<211> LENGTH: 187
<212> TYPE: PRT
<213> ORGANISM: Mycobacterium tuberculosis

<400> SEQUENCE: 80

Met Ala Asp Ala Asp Thr Thr Asp Phe Asp Val Asp Ala Glu Ala Pro
  1               5                  10                  15

Gly Gly Gly Val Arg Glu Asp Thr Ala Thr Asp Ala Asp Glu Ala Asp
                 20                  25                  30

Asp Gln Glu Glu Arg Leu Val Ala Glu Gly Glu Ile Ala Gly Asp Tyr
             35                  40                  45

Leu Glu Glu Leu Leu Asp Val Leu Asp Phe Asp Gly Asp Ile Asp Leu
         50                  55                  60

Asp Val Glu Gly Asn Arg Ala Val Val Ser Ile Asp Gly Ser Asp Asp
 65                  70                  75                  80

Leu Asn Lys Leu Val Gly Arg Gly Glu Val Leu Asp Ala Leu Gln
                 85                  90                  95

Glu Leu Thr Arg Leu Ala Val His Gln Lys Thr Gly Val Arg Ser Arg
                100                 105                 110

Leu Met Leu Asp Ile Ala Arg Trp Arg Arg Arg Arg Glu Glu Leu
                115                 120                 125

Ala Ala Leu Ala Asp Glu Val Ala Arg Val Ala Glu Thr Gly Asp
    130                 135                 140

Arg Glu Glu Leu Val Pro Met Thr Pro Phe Glu Arg Lys Ile Val His
145                 150                 155                 160

Asp Ala Val Ala Ala Val Pro Gly Val His Ser Glu Ser Glu Gly Val
                165                 170                 175
```

Glu Pro Glu Arg Arg Val Val Val Leu Arg Asp
            180                 185

<210> SEQ ID NO 81
<211> LENGTH: 207
<212> TYPE: PRT
<213> ORGANISM: Mycobacterium tuberculosis

<400> SEQUENCE: 81

Leu Cys Ala Lys Pro Tyr Leu Ile Asp Thr Ile Ala His Met Ala Ile
1               5                   10                  15

Trp Asp Arg Leu Val Glu Val Ala Ala Glu Gln His Gly Tyr Val Thr
            20                  25                  30

Thr Arg Asp Ala Arg Asp Ile Gly Val Asp Pro Val Gln Leu Arg Leu
        35                  40                  45

Leu Ala Gly Arg Gly Arg Leu Glu Arg Val Gly Arg Gly Val Tyr Arg
    50                  55                  60

Val Pro Val Leu Pro Arg Gly Glu His Asp Asp Leu Ala Ala Ala Val
65                  70                  75                  80

Ser Trp Thr Leu Gly Arg Gly Val Ile Ser His Glu Ser Ala Leu Ala
                85                  90                  95

Leu His Ala Leu Ala Asp Val Asn Pro Ser Arg Ile His Leu Thr Val
            100                 105                 110

Pro Arg Asn Asn His Pro Arg Ala Ala Gly Gly Glu Leu Tyr Arg Val
        115                 120                 125

His Arg Arg Asp Leu Gln Ala Ala His Val Thr Ser Val Asp Gly Ile
    130                 135                 140

Pro Val Thr Thr Val Ala Arg Thr Ile Lys Asp Cys Val Lys Thr Gly
145                 150                 155                 160

Thr Asp Pro Tyr Gln Leu Arg Ala Ala Ile Glu Arg Ala Glu Ala Glu
                165                 170                 175

Gly Thr Leu Arg Arg Gly Ser Ala Ala Glu Leu Arg Ala Ala Leu Asp
            180                 185                 190

Glu Thr Thr Ala Gly Leu Arg Ala Arg Pro Lys Arg Ala Ser Ala
        195                 200                 205

<210> SEQ ID NO 82
<211> LENGTH: 185
<212> TYPE: PRT
<213> ORGANISM: Mycobacterium tuberculosis

<400> SEQUENCE: 82

Met Ile Asp Glu Ala Leu Phe Asp Ala Glu Glu Lys Met Glu Lys Ala
1               5                   10                  15

Val Ala Val Ala Arg Asp Asp Leu Ser Thr Ile Arg Thr Gly Arg Ala
            20                  25                  30

Asn Pro Gly Met Phe Ser Arg Ile Thr Ile Asp Tyr Tyr Gly Ala Ala
        35                  40                  45

Thr Pro Ile Thr Gln Leu Ala Ser Ile Asn Val Pro Glu Ala Arg Leu
    50                  55                  60

Val Val Ile Lys Pro Tyr Glu Ala Asn Gln Leu Arg Ala Ile Glu Thr
65                  70                  75                  80

Ala Ile Arg Asn Ser Asp Leu Gly Val Asn Pro Thr Asn Asp Gly Ala
                85                  90                  95

Leu Ile Arg Val Ala Val Pro Gln Leu Thr Glu Glu Arg Arg Arg Glu
            100                 105                 110

Leu Val Lys Gln Ala Lys His Lys Gly Glu Glu Ala Lys Val Ser Val
                115                 120                 125

Arg Asn Ile Arg Arg Lys Ala Met Glu Glu Leu His Arg Ile Arg Lys
            130                 135                 140

Glu Gly Glu Ala Gly Glu Asp Glu Val Gly Arg Ala Glu Lys Asp Leu
145                 150                 155                 160

Asp Lys Thr Thr His Gln Tyr Val Thr Gln Ile Asp Glu Leu Val Lys
                165                 170                 175

His Lys Gly Glu Leu Leu Glu Val
            180             185

<210> SEQ ID NO 83
<211> LENGTH: 166
<212> TYPE: PRT
<213> ORGANISM: Mycobacterium tuberculosis

<400> SEQUENCE: 83

Met Pro Lys Leu Ser Ala Gly Val Leu Leu Tyr Arg Ala Arg Ala Gly
 1               5                  10                  15

Val Val Asp Val Leu Leu Ala His Pro Gly Gly Pro Phe Trp Ala Gly
             20                  25                  30

Lys Asp Asp Gly Ala Trp Ser Ile Pro Lys Gly Glu Tyr Thr Gly Gly
         35                  40                  45

Glu Asp Pro Trp Leu Ala Arg Arg Glu Phe Ser Glu Glu Ile Gly
     50                  55                  60

Leu Cys Val Pro Asp Gly Pro Arg Ile Asp Phe Gly Ser Leu Lys Gln
65                  70                  75                  80

Ser Gly Gly Lys Val Val Thr Val Phe Gly Val Arg Ala Asp Leu Asp
                85                  90                  95

Ile Thr Asp Ala Arg Ser Ser Thr Phe Glu Leu Asp Trp Pro Lys Gly
            100                 105                 110

Ser Gly Lys Met Arg Lys Phe Pro Glu Val Asp Arg Val Ser Trp Phe
        115                 120                 125

Pro Val Ala Arg Ala Arg Thr Lys Leu Leu Lys Gly Gln Arg Gly Phe
    130                 135                 140

Leu Asp Arg Leu Met Ala His Pro Ala Val Ala Gly Leu Ser Glu Gly
145                 150                 155                 160

Pro Glu Ser Leu Pro Arg
                165

<210> SEQ ID NO 84
<211> LENGTH: 35
<212> TYPE: DNA
<213> ORGANISM: Artificial Sequence
<220> FEATURE:
<223> OTHER INFORMATION: Synthetic Oligonucleotide Primer

<400> SEQUENCE: 84
gaaggagata taccatgcat catcatcatc atcat                              35

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 85
tgatgatgag aacccccccc                                              20

<210> SEQ ID NO 86
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 86
gaaggagata taccatgcat catcatcatc atcatgtgag cgcttcggag              50

<210> SEQ ID NO 87
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 87
tgatgatgag aacccccccc aggacctcca tgccggcgca                         40

<210> SEQ ID NO 88
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 88
gaaggagata taccatgcat catcatcatc atcatatgct gccgaagaac              50

<210> SEQ ID NO 89
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 89
tgatgatgag aacccccccc gccctcggcg gcgtctttcg                         40

<210> SEQ ID NO 90
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 90
gaaggagata taccatgcat catcatcatc atcatgtgag agttttgttg              50

<210> SEQ ID NO 91
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 91
tgatgatgag aacccccccc ctttcccaga gcccgcaacg                         40

<210> SEQ ID NO 92
<211> LENGTH: 50
<212> TYPE: DNA
<213> ORGANISM: Artificial Sequence

```
<220> FEATURE:
<223> OTHER INFORMATION: Synthetic Oligonucleotide Primer

<400> SEQUENCE: 92
gaaggagata taccatgcat catcatcatc atcatgtggt tatgcctctt          50

<210> SEQ ID NO 93
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 93
tgatgatgag aacccccccc tcccgaccct tcgggctggt                     40

<210> SEQ ID NO 94
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 94
gaaggagata taccatgcat catcatcatc atcatatgtc ggctcccgaa          50

<210> SEQ ID NO 95
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 95
tgatgatgag aacccccccc ggcggtcacc agcgagtagc                     40

<210> SEQ ID NO 96
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 96
gaaggagata taccatgcat catcatcatc atcatatgct cgagaaggcc          50

<210> SEQ ID NO 97
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 97
tgatgatgag aacccccccc gtcgaactga ggcggctcgg                     40

<210> SEQ ID NO 98
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 98
gaaggagata taccatgcat catcatcatc atcatatgcc atccgacacc          50
```

<210> SEQ ID NO 99
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 99
tgatgatgag aacccccccc cgtttccttc cgagttccaa                40

<210> SEQ ID NO 100
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 100
gaaggagata taccatgcat catcatcatc atcatgtgga cgagatcctg       50

<210> SEQ ID NO 101
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 101
tgatgatgag aacccccccc cctcgctcgg cgggccagtc                40

<210> SEQ ID NO 102
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 102
gaaggagata taccatgcat catcatcatc atcatatgac tacgagctac       50

<210> SEQ ID NO 103
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 103
tgatgatgag aaccccccccc aacagccgcg agttcatggt               40

<210> SEQ ID NO 104
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 104
gaaggagata taccatgcat catcatcatc atcatatgag cgtggattac       50

<210> SEQ ID NO 105
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 105
tgatgatgag aaccccccccc gctgaactga gtgtgcggcc                              40

<210> SEQ ID NO 106
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 106
gaaggagata taccatgcat catcatcatc atcatatgca gacaaccccca                  50

<210> SEQ ID NO 107
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 107
tgatgatgag aaccccccccc acgcgccacc gctttggccc                             40

<210> SEQ ID NO 108
<211> LENGTH: 50
<212> TYPE: DNA
<213> ORGANISM: Artificial Sequence
<220> FEATURE:
<223> OTHER INFORMATION: Synthetic Oligonucleotide Primer

<400> SEQUENCE: 108
gaaggagata taccatgcat catcatcatc atcatatgac gatccctgat                   50

<210> SEQ ID NO 109
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 109
tgatgatgag aacccccccc caggccatca aaaaagtcct                              40

<210> SEQ ID NO 110
<211> LENGTH: 501
<212> TYPE: DNA
<213> ORGANISM: Mycobacterium tuberculosis

<400> SEQUENCE: 110
gtgagcgctt cggagttctc ccgtgctgaa ctcgccgccg ccttcgagaa gttcgagaag        60
accgtggccc gcgccgccgc gacgcgcgac tgggattgct gggtgcagca ctacaccccc       120
gacgtcgaat acatcgagca cgcggcgggc atcatgcgag gccgccagcg ggtacgtgcc       180
tggattcaag aaacgatgac gaccttcccg ggcagtcaca tggtggcctt cccgtcgctg       240
tggtcggtga tcgacgagtc caccgggcga attatctgcg aattggacaa ccccatgctc       300
gaccccggcg acggcagcgt gatcagcgcg acgaacattt cgatcatcac ctatgccggc       360
aatggccagt ggtgccgtca agaagacatc tacaacccgt gcggttcct gcgggcggcg       420
atgaagtggt gtcgcaaggc gcaggagttg ggcaccctcg acgaggacgc ggcgcgttgg       480
atgcgccggc atggaggtcc t                                                 501

<210> SEQ ID NO 111
<211> LENGTH: 525
<212> TYPE: DNA
<213> ORGANISM: Mycobacterium tuberculosis

<400> SEQUENCE: 111

| | | | | | | |
|---|---|---|---|---|---|---|
| atgctgccga | agaacaccag | acccacctcg | gaaaccgccg | aagagttctg | ggacaactcg | 60 |
| ctgtggtgca | gctggggcga | ccgagaaacg | ggatacaccc | gcaccgtcac | ggtttcgatc | 120 |
| tgccaggtgg | cggacggcga | acgtgaggcc | gaagggttc | gggacatgat | gcggctggag | 180 |
| tgtccggctg | ggctggatct | acggacaccc | aacccgagg | catacgagat | taccggtcag | 240 |
| cggcccggag | aattcgtgtt | cgtgctcggc | tatctggggc | atgtgcgggc | catcgtgggc | 300 |
| aactgttaca | tcgagatcat | gccgatgggc | accaggtcg | agctgagcaa | gttgccgat | 360 |
| gtggcattgg | atatcggccg | cagtgtcgga | tgctcggcct | acgagaacga | cttcacgctg | 420 |
| ccggacattc | caacgcagtg | gcgcaaccag | ccgctgggct | ggtacacgca | aggccttgcc | 480 |
| ccctacctgc | cggggctgtc | ggacccgaaa | gacgccgccg | agggc | | 525 |

<210> SEQ ID NO 112
<211> LENGTH: 543
<212> TYPE: DNA
<213> ORGANISM: Mycobacterium tuberculosis

<400> SEQUENCE: 112

| | | | | | | |
|---|---|---|---|---|---|---|
| gtgagagttt | tgttgctggg | accgcccggg | gcgggcaagg | ggacgcaggc | ggtgaagctg | 60 |
| gccgagaagc | tcgggatccc | gcagatctcc | accggcgaac | tcttccggcg | caacatcgaa | 120 |
| gagggcacca | agctcggcgt | ggaagccaaa | cgctacttgg | atgccggtga | cttggtgccg | 180 |
| tccgacttga | ccaatgaact | cgtcgacgac | cggctgaaca | atccggacgc | ggccaacgga | 240 |
| ttcatcttgg | atggctatcc | acgctcggtc | gagcaggcca | aggcgcttca | cgagatgctc | 300 |
| gaacgccggg | ggaccgacat | cgacgcggtg | ctggagtttc | gtgtgtccga | ggaggtgttg | 360 |
| ttggagcgac | tcaaggggcg | tggccgcgcc | gacgacaccg | cgacgtcat | cctcaaccgg | 420 |
| atgaaggtct | accgcgacga | gaccgcgccg | ctgctggagt | actaccgcga | ccaattgaag | 480 |
| accgtcgacg | ccgtcggcac | catggacgag | gtgttcgccc | gtgcgttgcg | ggctctggga | 540 |
| aag | | | | | | 543 |

<210> SEQ ID NO 113
<211> LENGTH: 564
<212> TYPE: DNA
<213> ORGANISM: Mycobacterium tuberculosis

<400> SEQUENCE: 113

| | | | | | | |
|---|---|---|---|---|---|---|
| gtggttatgc | ctcttgtcac | gccaaccacc | gcggttccat | caccgggacc | cacacggctg | 60 |
| cgtgtagccg | atctcctgcg | cgccaccgac | caagccgcag | acgacgtgct | ggcggggcgc | 120 |
| tgcgaccacc | tgctacccga | cggtggtgtc | ccgcagacgc | agcgctggta | cacccgcatc | 180 |
| cacggtgacg | aggagctgga | tatctggctg | attagctggg | ttcccggtca | accgaccgag | 240 |
| ctgcacgacc | atggcgggtc | cctgggagcg | ttgaccgtgc | tgagcgggtc | gctcaacgaa | 300 |
| tatcgttggg | acgccgtcg | gttgcgacgg | cgccgcctcg | atgccggtga | tcaggcaggg | 360 |
| ttcccgttgg | gttgggtgca | cgacgtggtg | tgggcgcccc | ggccgattgg | ggggcctgat | 420 |
| gcggccggga | tggctgtggc | gccaaccctg | agcgtgcacg | cctactcgcc | gccgctgacg | 480 |
| gcgatgtcgt | actacgagat | caccgaacgc | aacacgctgc | gccgccagcg | caccgaattg | 540 | accgaccagc ccgaagggtc ggga 564

<210> SEQ ID NO 114
<211> LENGTH: 621
<212> TYPE: DNA
<213> ORGANISM: Mycobacterium tuberculosis

<400> SEQUENCE: 114

| | |
|---|---|
| atgtcggctc ccgaacgggt aaccggcttg tccgggcaac gttacgggga agtccttctc | 60 |
| gtaacacccg gggaggccgg tccacaggcc accgtttaca acagcttccc gcttaacgat | 120 |
| tgtccggccg agctgtggtc cgcgctcgat ccgcaagccc tagccaccga acacaaagcg | 180 |
| gccaccgccc tgctcaacgg tccgcgctat tggttgatga acgccatcga gaaggcgccc | 240 |
| cagggcccgc cggtgacgaa gaccttcggc gggatcgaga tgctccagca ggccacggtg | 300 |
| ctgctgtcat cgatgaaccc tgccccatac ccgtcagcc aggtcagccg caacacggtc | 360 |
| tttgtgttca acgccggcga agaggtctac gaactgcagg accccaaggg acagcgctgg | 420 |
| gtgatgcaga cgtggagtca agtggtggac cccaacctgt cccgagccga cctgcccaag | 480 |
| ctgggtgaac ggctcaacct gccagccggg tggtcctatc ataccccgcgt gcttaccagc | 540 |
| gagttgcggg tcgacactac caaccgggag gcccgcgtcc tgcaagacga cctcaccaac | 600 |
| agctactcgc tggtgaccgc c | 621 |

<210> SEQ ID NO 115
<211> LENGTH: 621
<212> TYPE: DNA
<213> ORGANISM: Mycobacterium tuberculosis

<400> SEQUENCE: 115

| | |
|---|---|
| atgctcgaga aggcccccca gaagtctgtc gccgatttct ggttcgatcc gctgtgcccg | 60 |
| tggtgctgga tcacgtcgcg ctggatcctc gaggtggcaa aggtccgcga catcgaggtg | 120 |
| aacttccacg tcatgagcct ggcaatactc aacgaaaacc gtgacgacct gcccgagcaa | 180 |
| taccgcgaag gcatggcgag ggcatgggga ccggtacggg tggcgatcgc cgccgagcag | 240 |
| gcccatgggg cgaaagtcct ggacccgctg tacaccgcga tgggcaaccg gattcacaac | 300 |
| cagggcaacc acgaactcga cgaggtcatc acccagtcgc tggcggacgc cggtctgccc | 360 |
| gcggagttgg ccaaggccgc taccagcgac gcttacgaca acgccctgcg caaaagccac | 420 |
| cacgccggga tggacgcggt gggcgaggac gtcggtacgc cgacgatcca tgtcaatggt | 480 |
| gtggcgttct tcgggccggt gctctcgaag attccgcgcg gcgaggaagc cggcaagctc | 540 |
| tgggatgcct cggttacctt cgcttcctac ccgcactttt ttgagctcaa gcggacccgc | 600 |
| accgagccgc ctcagttcga c | 621 |

<210> SEQ ID NO 116
<211> LENGTH: 642
<212> TYPE: DNA
<213> ORGANISM: Mycobacterium tuberculosis

<400> SEQUENCE: 116

| | |
|---|---|
| atgccatccg acaccagccc caacgggcta agccgccgtg aggagttgct ggctgttgcc | 60 |
| accaaactat tcgcggcgcg cggttatcac ggcacccgga tggacgacgt cgccgatgtg | 120 |
| atcgggctca acaaagcaac ggtctatcac tactacgcca gcaagtcgct gatcctgttc | 180 |
| gacatttacc gtcaggcggc cgagggcacc ctggccgccg tgcacgacga tccgtcctgg | 240 |

```
acggcccgtg aagcgctgta ccagtacacg gtccggctgc tcactgcgat cgcgagcaac    300
cccgagcggg ccgccgtgta cttccaggag cagccctaca tcaccgagtg gttcaccagc    360
gagcaggtcg ccgaggtccg cgagaaggag cagcaagtct acgagcacgt acacggcctg    420
atcgaccgcg ggattgccag cggcgagttc tatgagtgcg actcgcatgt ggtggcgctg    480
gggtacatcg gatgacgct gggcagctac cgctggctgc ggccgagcgg gcgccgaacg    540
gccaaggaga tcgcggcgga gttcagcacg gcactgctgc gcgggctgat ccgcgacgaa    600
tcgatccgca accagtctcc gcttggaact cggaaggaaa cg                       642

<210> SEQ ID NO 117
<211> LENGTH: 672
<212> TYPE: DNA
<213> ORGANISM: Mycobacterium tuberculosis

<400> SEQUENCE: 117
gtggacgaga tcctggccag ggcaggaatc ttccaaggcg tggagcccag cgcaatcgcc     60
gcactgacga aacagctgca gcccgtcgac ttccccgtg gacacacggt cttcgcggaa    120
ggggagccgg gcgatcggct gtacatcatc atctcgggga aggtcaagat cggtcgccgg    180
gcaccagacg gccgagaaaa cctgttaacc atcatgggcc cgtcggacat gttcggcgag    240
ttgtcgatct tcgacccggg tccgcgcacg tccagcgcga ccacgatcac cgaggtgcgg    300
gcggtgtcga tggaccgcga cgcgctgcgg tcatggatcg ccgatcgtcc cgaaatctcc    360
gaacagctgc tgcgggtgct ggcccgccgg ctgcgccgca ccaacaacaa cctggccgac    420
ctcatcttca ccgatgtgcc cggtcgggtg gccaagcagc tgttgcagct cgcccagcgt    480
ttcggcaccc aggaaggtgg cgcattgcgg gtcacccacg acctgacaca ggaagaaatc    540
gcccagctgg tcggggcctc acgcgagacg gtgaacaagg cactggctga tttcgctcac    600
cgcggctgga tccgccttga gggcaagagt gtgctgatct ctgactccga aagactggcc    660
cgccgagcga gg                                                        672

<210> SEQ ID NO 118
<211> LENGTH: 708
<212> TYPE: DNA
<213> ORGANISM: Mycobacterium tuberculosis

<400> SEQUENCE: 118
atgactacga gctacgccaa gatcgagata accgggacac tgaccgtcct gacgggcctg     60
cagatcgggg ccggcgatgg cttctccgcc atcgcgcgcg tcgacaagcc tgtcgttcgt    120
gatccgctga gcaggctgcc gatgattccg gtaccagcc tgaagggcaa ggtccgcacc    180
ttgctgtccc gccaatacgg cgccgacaca gaaacgtttt acaggaagcc gaatgaggac    240
cacgcccata tccgtcggct tttcggcgac accgaggagt acatgacggg ccgactcgtc    300
ttccgcgaca cgaagctcac caacaaagac gacctcgaag cccgcggcgc taagactctc    360
accgaggtga aattcgagaa cgccatcaac cgggtgaccg caaaggcaaa ccttcgccag    420
atggaacgcg tgatccccgg cagcgagttc gcgttctcac ttgtctacga ggtctccttc    480
ggcacccccg gcgaggaaca gaaggcgtct ctgccttcct ccgatgagat catcgaggac    540
ttcaacgcca tcgcgcgcgg cctgaagttg ctcgaactcg actacctcgg cggcagcgga    600
acccgtggct acgggcaggt caagttcagc aacctgaaag cccgcgccgc agtcggcgcc    660
ctcgacggtt tctctgctgga gaagctaaac catgaactcg cggctgtt              708
```

<210> SEQ ID NO 119
<211> LENGTH: 762
<212> TYPE: DNA
<213> ORGANISM: Mycobacterium tuberculosis

<400> SEQUENCE: 119

| | | | | | |
|---|---|---|---|---|---|
| atgagcgtgg | attacccca | aatggctgct | acccggggaa | gaatagaacc | ggccccgcgg | 60 |
| cgagttcgcg | gctatctcgg | acatgtgctc | gtcttcgaca | ccagtgcggc | gcgctatgtc | 120 |
| tgggaggttc | cctactaccc | gcagtactac | atcccgctgg | cggatgtccg | catggagttc | 180 |
| ctgcgcgacg | agaaccaccc | gcagcgagtg | cagctgggtc | cgtcgcggct | gcactccttg | 240 |
| gtaagcgccg | gtcagaccca | ccgatcggcg | gcgcgggtat | tcgatgtcga | cggcgacagc | 300 |
| ccggtggcgg | gcaccgtgcg | tttcaactgg | gatccgctgc | ggtggttcga | ggaggacgag | 360 |
| ccgatctacg | gccatccgcg | caatccctat | cagcgggccg | atgcgctgcg | ctcgcaccga | 420 |
| cacgtccgtg | tcgagctgga | cggcattgtg | ctcgctgaca | cccgatcgcc | cgttctgcta | 480 |
| ttcgaaactg | ggatacccac | aaggtattac | atcgatccgg | ccgacatcgc | tttcgagcat | 540 |
| ctggagccca | cctcgacgca | gacgttgtgt | ccgtacaagg | ggacgacgtc | gggctattgg | 600 |
| tctgtgcgcg | tcggcgacgc | cgtgcaccgc | gacctggcct | ggacgtatca | ctatccactg | 660 |
| cccgccgttg | ccccgatcgc | cggcctggtg | gcgttttaca | acgagaaggt | cgacctcacc | 720 |
| gtcgacggcg | tcgccctgcc | gcggccgcac | actcagttca | gc | | 762 |

<210> SEQ ID NO 120
<211> LENGTH: 783
<212> TYPE: DNA
<213> ORGANISM: Mycobacterium tuberculosis

<400> SEQUENCE: 120

| | | | | | |
|---|---|---|---|---|---|
| atgcagacaa | ccccaggcaa | gcgtcaacga | cggcagcgcg | gatccatcaa | ccccgaggac | 60 |
| atcatcagcg | gcgcattcga | actcgcccag | caggtatcga | tagacaactt | gagcatgcca | 120 |
| ttgctcggca | aacaccttgg | cgtcggggtc | accagcatct | actggtactt | ccgcaagaag | 180 |
| gacgatctgc | tcaacgcgat | gaccgaccgc | gctttgagca | agtacgtgtt | cgctaccccg | 240 |
| tacatcgaag | ccggcgactg | gcgcgaaacg | ttgcgcaatc | atgcccgctc | gatgcggaag | 300 |
| acgttcgcgg | acaaccccgt | actgtgcgat | ctgatactga | ttcgagcggc | gctgtccccg | 360 |
| aaaacggcgc | ggttgggcgc | ccaagagatg | gagaaggcca | tcgccaatct | ggtgacggcg | 420 |
| ggcctgtcgc | tcgaagacgc | tttcgacatc | tactcggcgg | tttcggtcca | cgtgcgcgga | 480 |
| tcggtggtgc | tagatcggct | ctcccgcaag | agccagtcgg | cgggcagcgg | accatccgcc | 540 |
| attgaacacc | ccgtggccat | cgatcccgcg | acgactccgc | tgcttgctca | cgcaactggg | 600 |
| aggggggcatc | ggatcggggc | ccccgatgaa | accaatttcg | aatatggtct | cgaatgcatc | 660 |
| ctcgaccatg | ctggccggtt | gatcgaacaa | agctcgaaag | ccgctggtga | ggtcgcagtg | 720 |
| cgccgcccca | cggccaccgc | cgatgcgcct | acgccgggcg | cgcgggccaa | agcggtggcg | 780 |
| cgt | | | | | | 783 |

<210> SEQ ID NO 121
<211> LENGTH: 918
<212> TYPE: DNA
<213> ORGANISM: Mycobacterium tuberculosis

<400> SEQUENCE: 121

| | | | | | |
|---|---|---|---|---|---|
| atgacgatcc | ctgatgccca | gacgttgatg | cggccgattc | tcgcgtatct | tgccgatgga | 60 |

-continued

```
caagcgaagt cggccaagga cgtcatcgcg gcgatgtccg acgagttcgg tctgtccgac      120
gacgagcggg cgcagatgtt gcccagcggt cggcaaagga ccatgtacga cagggtgcac      180
tggtctctca ctcacatgtc gcaggccgga ttgctcgacc gtcccacgcg gggccacgtc      240
caggtcacgg acacgggccg tcaagtcctg aaggcgcatc ccgagcgcgt cgacatggct      300
gtgctgcggg agttcccgtc gtacatcgct tttcgtgagc gaaccaaagc caagcagcca      360
gtcgacgcga ccgccaagcg accgtccggg acgatgtgc aggtctcacc cgaggatctc       420
atcgacgctg cgcttgcgga gaaccgggca gccgtcgagg gggagatcct gaagaaggca      480
ctcacgttgt cgcccaccgg gtttgaagat ctggttatca acttttgga ggcgatgggt       540
tacgggcgag ccggcgcggt ggaacggacg agtgcctccg gtgacgctgg catcgacgga      600
atcatcagcc aggacccgct cgggctggac cgcatctacg tgcaggccaa gcatacgcc       660
gtcgaccaaa cgattggccg gccgaagatc cacgagttcg ccggcgccct cctgggcaag      720
cagggcgacc ggggcgtcta catcaccacg tcatcgtttt cccgcggtgc ccgcgaggaa      780
gctgagcgga tcaacgcccg gatcgaactc atcgacggcg ctcggctggc cgagctgctc      840
gtgcggtatc gagtcggtgt ccaggcggtg cagaccgtcg aactcttacg gctcgacgag      900
gacttttttg atggcctg                                                   918
```

<210> SEQ ID NO 122
<211> LENGTH: 167
<212> TYPE: PRT
<213> ORGANISM: Mycobacterium tuberculosis

<400> SEQUENCE: 122

```
Val Ser Ala Ser Glu Phe Ser Arg Ala Glu Leu Ala Ala Ala Phe Glu
  1               5                  10                  15

Lys Phe Glu Lys Thr Val Ala Arg Ala Ala Thr Arg Asp Trp Asp
             20                  25                  30

Cys Trp Val Gln His Tyr Thr Pro Asp Val Glu Tyr Ile Glu His Ala
         35                  40                  45

Ala Gly Ile Met Arg Gly Arg Gln Arg Val Arg Ala Trp Ile Gln Glu
     50                  55                  60

Thr Met Thr Thr Phe Pro Gly Ser His Met Val Ala Phe Pro Ser Leu
 65                  70                  75                  80

Trp Ser Val Ile Asp Glu Ser Thr Gly Arg Ile Ile Cys Glu Leu Asp
                 85                  90                  95

Asn Pro Met Leu Asp Pro Gly Asp Gly Ser Val Ile Ser Ala Thr Asn
            100                 105                 110

Ile Ser Ile Ile Thr Tyr Ala Gly Asn Gly Gln Trp Cys Arg Gln Glu
        115                 120                 125

Asp Ile Tyr Asn Pro Leu Arg Phe Leu Arg Ala Ala Met Lys Trp Cys
    130                 135                 140

Arg Lys Ala Gln Glu Leu Gly Thr Leu Asp Glu Asp Ala Ala Arg Trp
145                 150                 155                 160

Met Arg Arg His Gly Gly Pro
                165
```

<210> SEQ ID NO 123
<211> LENGTH: 175
<212> TYPE: PRT
<213> ORGANISM: Mycobacterium tuberculosis

<400> SEQUENCE: 123

```
Met Leu Pro Lys Asn Thr Arg Pro Thr Ser Glu Thr Ala Glu Glu Phe
  1               5                  10                  15

Trp Asp Asn Ser Leu Trp Cys Ser Trp Gly Asp Arg Glu Thr Gly Tyr
             20                  25                  30

Thr Arg Thr Val Thr Val Ser Ile Cys Gln Val Ala Asp Gly Glu Arg
         35                  40                  45

Glu Ala Glu Gly Val Arg Asp Met Met Arg Leu Glu Cys Pro Ala Gly
 50                  55                  60

Leu Asp Leu Arg Thr Pro Asn Pro Glu Ala Tyr Glu Ile Thr Gly Gln
 65              70                  75                  80

Arg Pro Gly Glu Phe Val Phe Val Leu Gly Tyr Leu Gly His Val Arg
                 85                  90                  95

Ala Ile Val Gly Asn Cys Tyr Ile Glu Ile Met Pro Met Gly Thr Arg
             100                 105                 110

Val Glu Leu Ser Lys Leu Ala Asp Val Ala Leu Asp Ile Gly Arg Ser
             115                 120                 125

Val Gly Cys Ser Ala Tyr Glu Asn Asp Phe Thr Leu Pro Asp Ile Pro
 130                 135                 140

Thr Gln Trp Arg Asn Gln Pro Leu Gly Trp Tyr Thr Gln Gly Leu Ala
145                 150                 155                 160

Pro Tyr Leu Pro Gly Leu Ser Asp Pro Lys Asp Ala Ala Glu Gly
                 165                 170                 175

<210> SEQ ID NO 124
<211> LENGTH: 181
<212> TYPE: PRT
<213> ORGANISM: Mycobacterium tuberculosis

<400> SEQUENCE: 124

Val Arg Val Leu Leu Gly Pro Pro Gly Ala Gly Lys Gly Thr Gln
  1               5                  10                  15

Ala Val Lys Leu Ala Glu Lys Leu Gly Ile Pro Gln Ile Ser Thr Gly
             20                  25                  30

Glu Leu Phe Arg Arg Asn Ile Glu Glu Gly Thr Lys Leu Gly Val Glu
         35                  40                  45

Ala Lys Arg Tyr Leu Asp Ala Gly Asp Leu Val Pro Ser Asp Leu Thr
 50                  55                  60

Asn Glu Leu Val Asp Asp Arg Leu Asn Asn Pro Asp Ala Ala Asn Gly
 65              70                  75                  80

Phe Ile Leu Asp Gly Tyr Pro Arg Ser Val Glu Gln Ala Lys Ala Leu
                 85                  90                  95

His Glu Met Leu Glu Arg Arg Gly Thr Asp Ile Asp Ala Val Leu Glu
             100                 105                 110

Phe Arg Val Ser Glu Glu Val Leu Leu Glu Arg Leu Lys Gly Arg Gly
             115                 120                 125

Arg Ala Asp Asp Thr Asp Asp Val Ile Leu Asn Arg Met Lys Val Tyr
 130                 135                 140

Arg Asp Glu Thr Ala Pro Leu Leu Glu Tyr Tyr Arg Asp Gln Leu Lys
145                 150                 155                 160

Thr Val Asp Ala Val Gly Thr Met Asp Glu Val Phe Ala Arg Ala Leu
                 165                 170                 175

Arg Ala Leu Gly Lys
             180

<210> SEQ ID NO 125
```

<211> LENGTH: 188
<212> TYPE: PRT
<213> ORGANISM: Mycobacterium tuberculosis

<400> SEQUENCE: 125

Val Val Met Pro Leu Val Thr Pro Thr Thr Ala Val Pro Ser Pro Gly
1               5                   10                  15

Pro Thr Arg Leu Arg Val Ala Asp Leu Leu Arg Ala Thr Asp Gln Ala
            20                  25                  30

Ala Asp Asp Val Leu Gly Gly Arg Cys Asp His Leu Leu Pro Asp Gly
        35                  40                  45

Gly Val Pro Gln Thr Gln Arg Trp Tyr Thr Arg Ile His Gly Asp Glu
    50                  55                  60

Glu Leu Asp Ile Trp Leu Ile Ser Trp Val Pro Gly Gln Pro Thr Glu
65                  70                  75                  80

Leu His Asp His Gly Gly Ser Leu Gly Ala Leu Thr Val Leu Ser Gly
                85                  90                  95

Ser Leu Asn Glu Tyr Arg Trp Asp Gly Arg Arg Leu Arg Arg Arg Arg
            100                 105                 110

Leu Asp Ala Gly Asp Gln Ala Gly Phe Pro Leu Gly Trp Val His Asp
        115                 120                 125

Val Val Trp Ala Pro Arg Pro Ile Gly Gly Pro Asp Ala Ala Gly Met
    130                 135                 140

Ala Val Ala Pro Thr Leu Ser Val His Ala Tyr Ser Pro Pro Leu Thr
145                 150                 155                 160

Ala Met Ser Tyr Tyr Glu Ile Thr Glu Arg Asn Thr Leu Arg Arg Gln
                165                 170                 175

Arg Thr Glu Leu Thr Asp Gln Pro Glu Gly Ser Gly
            180                 185

<210> SEQ ID NO 126
<211> LENGTH: 207
<212> TYPE: PRT
<213> ORGANISM: Mycobacterium tuberculosis

<400> SEQUENCE: 126

Met Ser Ala Pro Glu Arg Val Thr Gly Leu Ser Gly Gln Arg Tyr Gly
1               5                   10                  15

Glu Val Leu Leu Val Thr Pro Gly Glu Ala Gly Pro Gln Ala Thr Val
            20                  25                  30

Tyr Asn Ser Phe Pro Leu Asn Asp Cys Pro Ala Glu Leu Trp Ser Ala
        35                  40                  45

Leu Asp Pro Gln Ala Leu Ala Thr Glu His Lys Ala Ala Thr Ala Leu
    50                  55                  60

Leu Asn Gly Pro Arg Tyr Trp Leu Met Asn Ala Ile Glu Lys Ala Pro
65                  70                  75                  80

Gln Gly Pro Pro Val Thr Lys Thr Phe Gly Ile Glu Met Leu Gln
                85                  90                  95

Gln Ala Thr Val Leu Leu Ser Ser Met Asn Pro Ala Pro Tyr Thr Val
            100                 105                 110

Ser Gln Val Ser Arg Asn Thr Val Phe Val Phe Asn Ala Gly Glu Glu
        115                 120                 125

Val Tyr Glu Leu Gln Asp Pro Lys Gly Gln Arg Trp Val Met Gln Thr
    130                 135                 140

Trp Ser Gln Val Val Asp Pro Asn Leu Ser Arg Ala Asp Leu Pro Lys
145                 150                 155                 160

```
Leu Gly Glu Arg Leu Asn Leu Pro Ala Gly Trp Ser Tyr His Thr Arg
                165                 170                 175

Val Leu Thr Ser Glu Leu Arg Val Asp Thr Thr Asn Arg Glu Ala Arg
            180                 185                 190

Val Leu Gln Asp Asp Leu Thr Asn Ser Tyr Ser Leu Val Thr Ala
        195                 200                 205
```

<210> SEQ ID NO 127
<211> LENGTH: 207
<212> TYPE: PRT
<213> ORGANISM: Mycobacterium tuberculosis

<400> SEQUENCE: 127

```
Met Leu Glu Lys Ala Pro Gln Lys Ser Val Ala Asp Phe Trp Phe Asp
  1               5                  10                  15

Pro Leu Cys Pro Trp Cys Trp Ile Thr Ser Arg Trp Ile Leu Glu Val
                20                  25                  30

Ala Lys Val Arg Asp Ile Glu Val Asn Phe His Val Met Ser Leu Ala
             35                  40                  45

Ile Leu Asn Glu Asn Arg Asp Asp Leu Pro Gln Tyr Arg Glu Gly
 50                  55                  60

Met Ala Arg Ala Trp Gly Pro Val Arg Val Ala Ile Ala Ala Glu Gln
 65                  70                  75                  80

Ala His Gly Ala Lys Val Leu Asp Pro Leu Tyr Thr Ala Met Gly Asn
                 85                  90                  95

Arg Ile His Asn Gln Gly Asn His Glu Leu Asp Glu Val Ile Thr Gln
                100                 105                 110

Ser Leu Ala Asp Ala Gly Leu Pro Ala Glu Leu Ala Lys Ala Ala Thr
            115                 120                 125

Ser Asp Ala Tyr Asp Asn Ala Leu Arg Lys Ser His His Ala Gly Met
130                 135                 140

Asp Ala Val Gly Glu Asp Val Gly Thr Pro Thr Ile His Val Asn Gly
145                 150                 155                 160

Val Ala Phe Phe Gly Pro Val Leu Ser Lys Ile Pro Arg Gly Glu Glu
                165                 170                 175

Ala Gly Lys Leu Trp Asp Ala Ser Val Thr Phe Ala Ser Tyr Pro His
            180                 185                 190

Phe Phe Glu Leu Lys Arg Thr Arg Thr Glu Pro Pro Gln Phe Asp
        195                 200                 205
```

<210> SEQ ID NO 128
<211> LENGTH: 214
<212> TYPE: PRT
<213> ORGANISM: Mycobacterium tuberculosis

<400> SEQUENCE: 128

```
Met Pro Ser Asp Thr Ser Pro Asn Gly Leu Ser Arg Arg Glu Glu Leu
  1               5                  10                  15

Leu Ala Val Ala Thr Lys Leu Phe Ala Ala Arg Gly Tyr His Gly Thr
                20                  25                  30

Arg Met Asp Asp Val Ala Asp Val Ile Gly Leu Asn Lys Ala Thr Val
             35                  40                  45

Tyr His Tyr Tyr Ala Ser Lys Ser Leu Ile Leu Phe Asp Ile Tyr Arg
 50                  55                  60

Gln Ala Ala Glu Gly Thr Leu Ala Ala Val His Asp Asp Pro Ser Trp
 65                  70                  75                  80
```

Thr Ala Arg Glu Ala Leu Tyr Gln Tyr Thr Val Arg Leu Leu Thr Ala
                85                  90                  95

Ile Ala Ser Asn Pro Glu Arg Ala Ala Val Tyr Phe Gln Glu Gln Pro
            100                 105                 110

Tyr Ile Thr Glu Trp Phe Thr Ser Glu Gln Val Ala Glu Val Arg Glu
        115                 120                 125

Lys Glu Gln Gln Val Tyr Glu His Val His Gly Leu Ile Asp Arg Gly
    130                 135                 140

Ile Ala Ser Gly Glu Phe Tyr Glu Cys Asp Ser His Val Val Ala Leu
145                 150                 155                 160

Gly Tyr Ile Gly Met Thr Leu Gly Ser Tyr Arg Trp Leu Arg Pro Ser
                165                 170                 175

Gly Arg Arg Thr Ala Lys Glu Ile Ala Ala Glu Phe Ser Thr Ala Leu
            180                 185                 190

Leu Arg Gly Leu Ile Arg Asp Glu Ser Ile Arg Asn Gln Ser Pro Leu
        195                 200                 205

Gly Thr Arg Lys Glu Thr
    210

<210> SEQ ID NO 129
<211> LENGTH: 224
<212> TYPE: PRT
<213> ORGANISM: Mycobacterium tuberculosis

<400> SEQUENCE: 129

Val Asp Glu Ile Leu Ala Arg Ala Gly Ile Phe Gln Gly Val Glu Pro
1               5                   10                  15

Ser Ala Ile Ala Ala Leu Thr Lys Gln Leu Gln Pro Val Asp Phe Pro
            20                  25                  30

Arg Gly His Thr Val Phe Ala Glu Gly Glu Pro Gly Asp Arg Leu Tyr
        35                  40                  45

Ile Ile Ile Ser Gly Lys Val Lys Ile Gly Arg Arg Ala Pro Asp Gly
    50                  55                  60

Arg Glu Asn Leu Leu Thr Ile Met Gly Pro Ser Asp Met Phe Gly Glu
65                  70                  75                  80

Leu Ser Ile Phe Asp Pro Gly Pro Arg Thr Ser Ser Ala Thr Thr Ile
                85                  90                  95

Thr Glu Val Arg Ala Val Ser Met Asp Arg Asp Ala Leu Arg Ser Trp
            100                 105                 110

Ile Ala Asp Arg Pro Glu Ile Ser Glu Gln Leu Leu Arg Val Leu Ala
        115                 120                 125

Arg Arg Leu Arg Arg Thr Asn Asn Asn Leu Ala Asp Leu Ile Phe Thr
    130                 135                 140

Asp Val Pro Gly Arg Val Ala Lys Gln Leu Leu Gln Leu Ala Gln Arg
145                 150                 155                 160

Phe Gly Thr Gln Glu Gly Gly Ala Leu Arg Val Thr His Asp Leu Thr
                165                 170                 175

Gln Glu Glu Ile Ala Gln Leu Val Gly Ala Ser Arg Glu Thr Val Asn
            180                 185                 190

Lys Ala Leu Ala Asp Phe Ala His Arg Gly Trp Ile Arg Leu Glu Gly
        195                 200                 205

Lys Ser Val Leu Ile Ser Asp Ser Glu Arg Leu Ala Arg Arg Ala Arg
    210                 215                 220

-continued

```
<210> SEQ ID NO 130
<211> LENGTH: 236
<212> TYPE: PRT
<213> ORGANISM: Mycobacterium tuberculosis

<400> SEQUENCE: 130

Met Thr Thr Ser Tyr Ala Lys Ile Glu Ile Thr Gly Thr Leu Thr Val
1               5                   10                  15

Leu Thr Gly Leu Gln Ile Gly Ala Gly Asp Gly Phe Ser Ala Ile Gly
            20                  25                  30

Ala Val Asp Lys Pro Val Val Arg Asp Pro Leu Ser Arg Leu Pro Met
        35                  40                  45

Ile Pro Gly Thr Ser Leu Lys Gly Lys Val Arg Thr Leu Leu Ser Arg
50                  55                  60

Gln Tyr Gly Ala Asp Thr Glu Thr Phe Tyr Arg Lys Pro Asn Glu Asp
65                  70                  75                  80

His Ala His Ile Arg Arg Leu Phe Gly Asp Thr Glu Glu Tyr Met Thr
                85                  90                  95

Gly Arg Leu Val Phe Arg Asp Thr Lys Leu Thr Asn Lys Asp Asp Leu
            100                 105                 110

Glu Ala Arg Gly Ala Lys Thr Leu Thr Glu Val Lys Phe Glu Asn Ala
        115                 120                 125

Ile Asn Arg Val Thr Ala Lys Ala Asn Leu Arg Gln Met Glu Arg Val
130                 135                 140

Ile Pro Gly Ser Glu Phe Ala Phe Ser Leu Val Tyr Glu Val Ser Phe
145                 150                 155                 160

Gly Thr Pro Gly Glu Glu Gln Lys Ala Ser Leu Pro Ser Ser Asp Glu
                165                 170                 175

Ile Ile Glu Asp Phe Asn Ala Ile Ala Arg Gly Leu Lys Leu Leu Glu
            180                 185                 190

Leu Asp Tyr Leu Gly Gly Ser Gly Thr Arg Gly Tyr Gly Gln Val Lys
        195                 200                 205

Phe Ser Asn Leu Lys Ala Arg Ala Ala Val Gly Ala Leu Asp Gly Ser
210                 215                 220

Leu Leu Glu Lys Leu Asn His Glu Leu Ala Ala Val
225                 230                 235

<210> SEQ ID NO 131
<211> LENGTH: 254
<212> TYPE: PRT
<213> ORGANISM: Mycobacterium tuberculosis

<400> SEQUENCE: 131

Met Ser Val Asp Tyr Pro Gln Met Ala Ala Thr Arg Gly Arg Ile Glu
1               5                   10                  15

Pro Ala Pro Arg Arg Val Arg Gly Tyr Leu Gly His Val Leu Val Phe
            20                  25                  30

Asp Thr Ser Ala Ala Arg Tyr Val Trp Glu Val Pro Tyr Tyr Pro Gln
        35                  40                  45

Tyr Tyr Ile Pro Leu Ala Asp Val Arg Met Glu Phe Leu Arg Asp Glu
50                  55                  60

Asn His Pro Gln Arg Val Gln Leu Gly Pro Ser Arg Leu His Ser Leu
65                  70                  75                  80

Val Ser Ala Gly Gln Thr His Arg Ser Ala Ala Arg Val Phe Asp Val
                85                  90                  95

Asp Gly Asp Ser Pro Val Ala Gly Thr Val Arg Phe Asn Trp Asp Pro
```

-continued

```
                100                 105                 110
Leu Arg Trp Phe Glu Glu Asp Glu Pro Ile Tyr Gly His Pro Arg Asn
            115                 120                 125

Pro Tyr Gln Arg Ala Asp Ala Leu Arg Ser His Arg His Val Arg Val
        130                 135                 140

Glu Leu Asp Gly Ile Val Leu Ala Asp Thr Arg Ser Pro Val Leu Leu
145                 150                 155                 160

Phe Glu Thr Gly Ile Pro Thr Arg Tyr Tyr Ile Asp Pro Ala Asp Ile
                165                 170                 175

Ala Phe Glu His Leu Glu Pro Thr Ser Thr Gln Thr Leu Cys Pro Tyr
            180                 185                 190

Lys Gly Thr Thr Ser Gly Tyr Trp Ser Val Arg Val Gly Asp Ala Val
        195                 200                 205

His Arg Asp Leu Ala Trp Thr Tyr His Tyr Pro Leu Pro Ala Val Ala
    210                 215                 220

Pro Ile Ala Gly Leu Val Ala Phe Tyr Asn Glu Lys Val Asp Leu Thr
225                 230                 235                 240

Val Asp Gly Val Ala Leu Pro Arg Pro His Thr Gln Phe Ser
                245                 250
```

<210> SEQ ID NO 132
<211> LENGTH: 261
<212> TYPE: PRT
<213> ORGANISM: Mycobacterium tuberculosis

<400> SEQUENCE: 132

```
Met Gln Thr Thr Pro Gly Lys Arg Gln Arg Gln Arg Gly Ser Ile
1               5                   10                  15

Asn Pro Glu Asp Ile Ile Ser Gly Ala Phe Glu Leu Ala Gln Gln Val
            20                  25                  30

Ser Ile Asp Asn Leu Ser Met Pro Leu Leu Gly Lys His Leu Gly Val
        35                  40                  45

Gly Val Thr Ser Ile Tyr Trp Tyr Phe Arg Lys Lys Asp Asp Leu Leu
    50                  55                  60

Asn Ala Met Thr Asp Arg Ala Leu Ser Lys Tyr Val Phe Ala Thr Pro
65                  70                  75                  80

Tyr Ile Glu Ala Gly Asp Trp Arg Glu Thr Leu Arg Asn His Ala Arg
                85                  90                  95

Ser Met Arg Lys Thr Phe Ala Asp Asn Pro Val Leu Cys Asp Leu Ile
            100                 105                 110

Leu Ile Arg Ala Ala Leu Ser Pro Lys Thr Ala Arg Leu Gly Ala Gln
        115                 120                 125

Glu Met Glu Lys Ala Ile Ala Asn Leu Val Thr Ala Gly Leu Ser Leu
    130                 135                 140

Glu Asp Ala Phe Asp Ile Tyr Ser Ala Val Ser Val His Val Arg Gly
145                 150                 155                 160

Ser Val Val Leu Asp Arg Leu Ser Arg Lys Ser Gln Ser Ala Gly Ser
                165                 170                 175

Gly Pro Ser Ala Ile Glu His Pro Val Ala Ile Asp Pro Ala Thr Thr
            180                 185                 190

Pro Leu Leu Ala His Ala Thr Gly Arg Gly His Arg Ile Gly Ala Pro
        195                 200                 205

Asp Glu Thr Asn Phe Glu Tyr Gly Leu Glu Cys Ile Leu Asp His Ala
    210                 215                 220
```

```
Gly Arg Leu Ile Glu Gln Ser Ser Lys Ala Ala Gly Glu Val Ala Val
225                 230                 235                 240

Arg Arg Pro Thr Ala Thr Ala Asp Ala Pro Thr Pro Gly Ala Arg Ala
                245                 250                 255

Lys Ala Val Ala Arg
            260

<210> SEQ ID NO 133
<211> LENGTH: 306
<212> TYPE: PRT
<213> ORGANISM: Mycobacterium tuberculosis

<400> SEQUENCE: 133

Met Thr Ile Pro Asp Ala Gln Thr Leu Met Arg Pro Ile Leu Ala Tyr
1               5                   10                  15

Leu Ala Asp Gly Gln Ala Lys Ser Ala Lys Asp Val Ile Ala Ala Met
                20                  25                  30

Ser Asp Glu Phe Gly Leu Ser Asp Asp Glu Arg Ala Gln Met Leu Pro
            35                  40                  45

Ser Gly Arg Gln Arg Thr Met Tyr Asp Arg Val His Trp Ser Leu Thr
50                  55                  60

His Met Ser Gln Ala Gly Leu Leu Asp Arg Pro Thr Arg Gly His Val
65                  70                  75                  80

Gln Val Thr Asp Thr Gly Arg Gln Val Leu Lys Ala His Pro Glu Arg
                85                  90                  95

Val Asp Met Ala Val Leu Arg Glu Phe Pro Ser Tyr Ile Ala Phe Arg
            100                 105                 110

Glu Arg Thr Lys Ala Lys Gln Pro Val Asp Ala Thr Ala Lys Arg Pro
        115                 120                 125

Ser Gly Asp Asp Val Gln Val Ser Pro Glu Asp Leu Ile Asp Ala Ala
    130                 135                 140

Leu Ala Glu Asn Arg Ala Ala Val Glu Gly Glu Ile Leu Lys Lys Ala
145                 150                 155                 160

Leu Thr Leu Ser Pro Thr Gly Phe Glu Asp Leu Val Ile Arg Leu Leu
                165                 170                 175

Glu Ala Met Gly Tyr Gly Arg Ala Gly Ala Val Glu Arg Thr Ser Ala
            180                 185                 190

Ser Gly Asp Ala Gly Ile Asp Gly Ile Ile Ser Gln Asp Pro Leu Gly
        195                 200                 205

Leu Asp Arg Ile Tyr Val Gln Ala Lys Arg Tyr Ala Val Asp Gln Thr
    210                 215                 220

Ile Gly Arg Pro Lys Ile His Glu Phe Ala Gly Ala Leu Leu Gly Lys
225                 230                 235                 240

Gln Gly Asp Arg Gly Val Tyr Ile Thr Thr Ser Ser Phe Ser Arg Gly
                245                 250                 255

Ala Arg Glu Glu Ala Glu Arg Ile Asn Ala Arg Ile Glu Leu Ile Asp
            260                 265                 270

Gly Ala Arg Leu Ala Glu Leu Leu Val Arg Tyr Arg Val Gly Val Gln
        275                 280                 285

Ala Val Gln Thr Val Glu Leu Leu Arg Leu Asp Glu Asp Phe Phe Asp
    290                 295                 300

Gly Leu
305
```

TUBERCULOSIS NUCLEIC ACIDS, POLYPEPTIDES AND IMMUNOGENIC COMPOSITIONS

The present application claims the benefit under 35 U.S.C. 119(e) of the filing date of U.S. Application Ser. No. 60/632,573 filed on Dec. 1, 2004 and 60/730,951, filed Oct. 26, 2005, which is are incorporated herein by reference.

STATEMENT REGARDING FEDERALLY SPONSORED RESEARCH AND DEVELOPMENT

The research leading to the present invention was supported, at least in part, by a grant from the National Institute of Allergy And Infectious Diseases. Accordingly, the Government may have certain rights in the invention.

BACKGROUND OF THE INVENTION

1. Field of the Invention

The present invention relates to immunogenic *Mycobacterium tuberculosis* (Mtb) peptides, polypeptides, polynucleotides encoding immunogenic Mtb peptides and polypeptides and immunogenic compositions comprising Mtb polypeptides or polynucleotides.

2. Background

Traditional vaccine technology suffers from the problem that it often produces various degrees of immunogenicity in different hosts. Often, the only reliably immunogenic composition is a pathogenic microorganism. But the manufacture and administration of the pathogenic organism carries a risk of infection by the very pathogen the vaccine is designed to treat. Furthermore, recent well-publicized problems with influenza vaccine production highlight the difficulties in producing large quantities of conventional vaccines and the precarious state of worldwide vaccine supplies. In light of general health concerns and the growing threat of bioterrorism, there is a need to develop recombinant and subunit vaccines capable of inducing an appropriate immune response in the context of multiple and genetically diverse hosts. This approach requires the identification of a number of specific antigenic polypeptides. One of the most difficult tasks in developing a protective or therapeutic vaccine, be it a recombinant or genetic, subunit or multi-valent vaccine, is the identification of the appropriate antigens that can stimulate the most rapid, sustained and efficacious immune responses against a particular pathogen for protection and/or therapeutic effect. This is especially challenging when the genome of the pathogen is large and screening for immunogenic antigens is tedious.

Tuberculosis is a chronic infectious disease that kills approximately 3 million people per year. It has been estimated that two billion people are infected with *M. tuberculosis* worldwide, including 7.5 million with active cases of tuberculosis. In recent years there has been an unexpected rise in tuberculosis cases.

In the U.S., tuberculosis continues to be a major problem especially among the homeless, Native Americans, African-Americans, immigrants, and the elderly. Immunocompromised individuals are particularly susceptible to tuberculosis. Of the 88 million, new cases of tuberculosis projected in this decade, approximately 10% are expected to be attributable to HIV infection. The emergence of AIDS has reactivated millions of dormant cases of tuberculosis (Mtb), causing a sharp rise in the number of tuberculosis-associated deaths.

The only available vaccine for tuberculosis, BCG, is both unpredictable and highly variable in protective efficacy. Hundreds of millions of children and newborns have been vaccinated with BCG, yet this has not consistently stopped the spread of the disease. Tuberculosis has become one of the fastest spreading infectious diseases in both industrialized and developing countries worldwide. Doubtful efficacy of vaccination has spurred interest in developing effective alternatives to BCG.

The emergence of multi-drug resistant strains of *M. tuberculosis* e.g. or Mtb, has complicated matters further, with some experts predicting a new tuberculosis epidemic. In the U.S. about 14% of *M. tuberculosis* isolates are resistant to at least one drug, and approximately 3% are resistant to at least two drugs. Some *M. tuberculosis* strains have been isolated that are resistant to as many as seven drugs in the repertoire of drugs commonly used to combat tuberculosis. Resistant strains make treatment of tuberculosis extremely difficult, leading to a mortality rate of about 90%, which is one of the reasons it has gained priority as a defined CDC—Category C Biodefense organism.

In the current age, where treatment of tuberculosis is becoming more challenging and immunosuppressive diseases are more prevalent, new vaccines are essential. Thus, there is a need for developing and commercializing effective and reliable Mtb vaccines. In addition, there is a considerable need for additional diagnostic tests or tests to detect active TB in the face of other diseases such as HIV.

SUMMARY OF THE INVENTION

The present invention provides isolated polynucleotides encoding a Mtb polypeptide that is antigenic in any mammal, including SEQ ID NOS: 46-64, 110-121, and fragments thereof, that encode antigenic polypeptides. The mammal can be, for example, a mouse, rabbit, non-human primate, or human. The invention also provides isolated polynucleotides encoding highly immunogenic Mtb antigens including SEQ ID NOS: 46-64, 110-121 and fragments thereof that encode highly immunogenic polypeptides. In some embodiments, highly immunogenic Mtb antigens react with polyclonal antibodies directed to Mtb bacteria (Mtb) from at least two different species. In another embodiment, highly immunogenic Mtb antigens are detected by ELISA, Western blotting, or both using polyclonal antibodies that are directed to Mtb bacteria.

The present invention also provides TAP polynucleotides, e.g. polynucleotides produced by Transcriptionally-Activated PCR (TAP) technology as described in U.S. Pat. No. 6,280,977, which is expressly incorporated herein by reference. Such polynucleotides include a 5' TAP polynucleotide sequence, a Mtb polynucleotide sequence, and a 3' TAP polynucleotide sequence. The Mtb polynucleotide sequence can, for example, comprise one of SEQ ID NOS: 46-64 and 110-121. In some embodiments, the 5' TAP polynucleotide sequence comprises a promoter. In certain embodiments, the 5' TAP polynucleotide sequence is selected from SEQ ID NOS: 2, 3, 6, and 84. In some embodiments the 3' TAP polynucleotide sequence comprises a terminator. In certain embodiments, the 3' TAP polynucleotide sequence is selected from SEQ ID NOS: 4, 5, 7, and 85.

The present invention also provides primer pairs for amplifying an Mtb polynucleotide. These primer pairs include SEQ ID NOS: 8 and 9; 10 and 11; 12 and 13; 14 and 15; 16 and 17; 18 and 19; 20 and 21; 22 and 23; 24 and 25; 26 and 27; 28 and 29; 30 and 31; 32 and 33; 34 and 35; 36 and 37; 38 and 39; 40 and 41; 42 and 43; 44and 45; 86 and 87; 88 and 89; 90 and 91; 92 and 93; 94 and 95; 96 and 97; 98 and 99; 100 and 101; 102 and 103; 104 and 105; 106 and 107; 108 and 109.

Isolated antigenic Mtb peptides and polypeptides are encompassed by the invention, including SEQ ID NOS: 65-83, 122-133, and fragments thereof. Isolated Mtb peptides and polypeptides that are highly immunogenic, including SEQ ID NOS: 65-83, 122-133, and fragments thereof, that are highly immunogenic, are also included in the invention. In one embodiment immunogenic peptides and polypeptides react with polyclonal antibodies that are directed to Mtb bacteria (Mtb). In one aspect of this embodiment, the peptides and polypeptides react with polyclonal antibodies that are directed to Mtb bacteria from at least two different species. In another embodiment, highly immunogenic peptides and polypeptides are detected by ELISA, Western blotting or both using polyclonal antibodies that are directed to Mtb bacteria.

The present invention also includes recombinant Mtb peptides and polypeptides, wherein the amino terminus of the peptide or polypeptide comprises an HA tag or a (6×)His tag, and the carboxy terminus of the polypeptide is selected from the group consisting of: SEQ ID NOS: 65-83 and 122-133. Also included are recombinant Mtb peptides and polypeptides, wherein the carboxy terminus of the polypeptide comprises a HA tag or a His tag, and the amino terminus of the polypeptide is selected from the group consisting of: SEQ ID NOS: 65-83 and 122-133. The peptides and polypeptides of the invention may be expressed in an appropriate in vitro transcription and translation system, such as a T7 polymerase system.

Immunogenic compositions for inducing an immunological response in a mammalian host against Mtb are also included in the invention. In one embodiment, the immunogenic compositions comprise nucleic acids that encode and express in vivo in a mammalian host cell at least one immunogenic peptide or polypeptide, which may be any one of SEQ ID NOS: 65-83, 122-133, or immunogenic fragments thereof. The nucleic acids can be, for example, plasmids or TAP fragments. The compositions can induce either a humoral- or cell-mediated immune response. Furthermore, the immunogenic compositions can include additional components, such as adjuvants, as well as other applications such as serodiagnostics.

Immunogenic compositions for inducing an immunological response in a mammalian host against Mtb of the invention can also comprise isolated Mtb peptides and/or polypeptides, such as SEQ ID NOS: 65-83, 122-133 and immunogenic fragments thereof. In one embodiment, the immunogenic peptides and polypeptides are expressed in an in vitro transcription and translation system. The immunogenic peptide and polypeptide compositions can induce either a humoral- or cell-mediated immune response. Furthermore, the immunogenic peptide and polypeptide compositions can include additional components, such as adjuvants, and include other applications such as diagnostics.

Similarly, detection of Mtb, its constituent proteins, and/or its immunologically reactive products (e.g. antibodies) is clinically relevant for the diagnosis of Mtb, and to track the efficacy of therapeutic treatments for Mtb, especially as translated to serodiagnostic tests. The present application therefore provides antigens for detection of Mtb for immune assays, including humoral immune assays. These antigens are applicable to detection of active Mtb in the face of HIV- and other Mycobacterial-coinfections, multi-drug resistant infections by Mtb(MDRI), and rapidly mutating forms of Mtb depending on genetic makeup, geographical location, and immunocompetency status.

As such, the present invention also provides diagnostic compositions, including one or more antibodies directed against the peptide epitopes identified herein. Also, the present invention provides diagnostic kits that include at least one or more of such antibodies.

In addition, the invention provides a method of generating an immune response in a mammalian host against Mtb. The method includes administering to said mammalian host an immunogenic composition comprising at least one nucleic acid selected from the group of SEQ ID NO: 46-64, 110-121, fragments thereof or combinations thereof, wherein said nucleic acid encodes and expresses in vivo at least one immunogenic peptide or polypeptide, whereby said immune response against Mtb is generated.

Also, the invention provides a method of generating an immune response in a mammalian host against Mtb, the method including administering to said mammalian host an immunogenic composition comprising at least one nucleic acid encoding and expressing in vivo at least one immunogenic peptide or polypeptide selected from the group of SEQ ID NO: 65-83,122-133, fragments thereof or combinations thereof, whereby said immune response against Mtb is generated.

In addition, the invention provides a method of generating an immune response in a mammalian host against Mtb comprising administering to said mammalian host an immunogenic composition comprising at least one immunogenic peptide or polypeptide selected from SEQ ID NO: 65-83, 122-133, fragment thereof or combinations thereof, whereby said immune response against Mtb is generated.

Also, the invention provides kits. In one embodiment the kits include at least one Mtb immunogenic composition selected from a nucleic acid selected from the group consisting of SEQ ID NO: 46-64, 110-121, fragments thereof or combinations thereof, or a peptide selected from the group consisting of SEQ ID NO: 65-83, 122-133, fragments thereof or combinations thereof and an adjuvant. The kit may also include an expression system. In addition the kit may include at least 2, 5, 10, 15, 20 or more of said immunogenic compositions, including nucleic acids and/or peptides, combinations or fragments thereof. In addition, the kit may include controls, e.g., positive and/or negative controls.

DETAILED DESCRIPTION OF THE INVENTION

Figure 1:
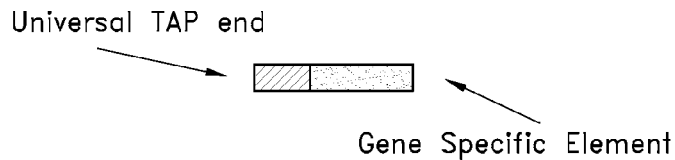
FIG. 1. illustrates one method used to generate TAP Expression Fragments.
Figure 1:
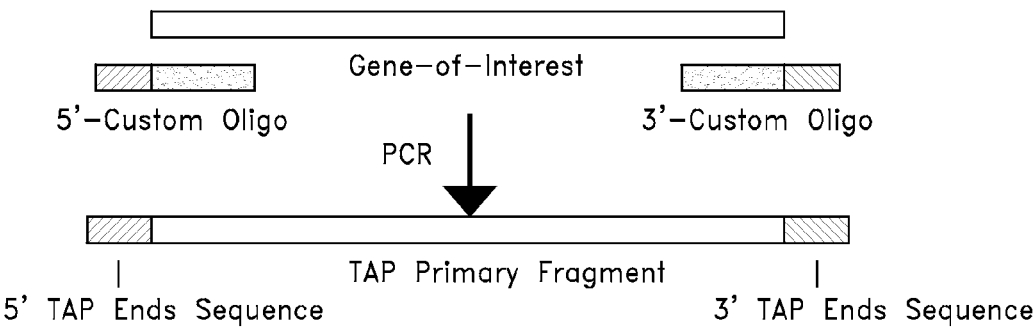
Figure 1:
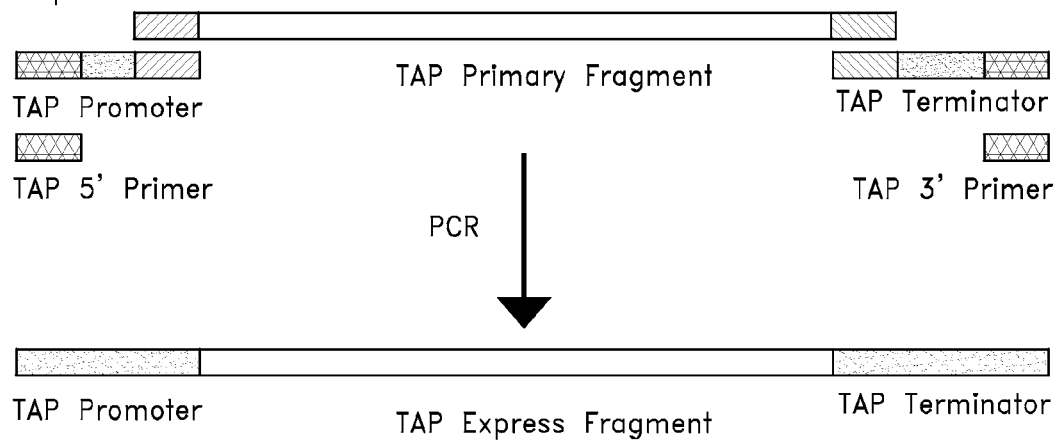

Before proceeding further with a description of the specific embodiments of the present invention, a number of terms will be defined and described in detail.

Unless specific definitions are provided, the nomenclature utilized in connection with, and the laboratory procedures, techniques and methods described herein are those known in the art to which they pertain. Standard chemical symbols and abbreviations are used interchangeably with the full names represented by such symbols. Thus, for example, the terms "carbon" and "C" are understood to have identical meaning. Standard techniques may be used for chemical syntheses, chemical analyses, pharmaceutical preparation, formulation, delivery, and treatment of patients. Standard techniques may be used for recombinant DNA methodology, oligonucleotide synthesis, tissue culture and the like. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. All references cited herein are incorporated by reference in their entirety and are not admitted to be prior art. See e.g., Sambrook et al. *Molecular Cloning: A Laboratory Manual* (3rd ed., Cold Spring Harbor Laboratory Press, Cold Spring Harbor, N.Y. (2000)), Harlow & Lane, *Antibodies: A Laboratory Manual* (Cold Spring Harbor Laboratory Press, Cold Spring Harbor, N.Y. (1988)), which are incorporated herein by reference in their entirety for any purpose.

The terms "polynucleotide" and "nucleic acid (molecule)" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-stranded, double-stranded and triple helical molecules. The following are non-limiting embodiments of polynucleotides: a gene, a gene fragment, exons, introns, mRNA, tRNA, rRNA, ribozymes, cDNA, recombinant polynucleotides, branched polynucleotides, plasmids, cosmids, viruses and other vectors, isolated DNA of any sequence, isolated RNA of any sequence, nucleic acid probes and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentyluracil and 2,6-diaminopurine.

The use of uracil as a substitute for thymine in a deoxyribonucleic acid is also considered an analogous form of pyrimidine.

Sugar modifications (e.g., 2'-o-methyl, 2-fluoro and the like) and phosphate backbone modifications (e.g., morpholino, PNA', thioates, dithioates and the like) can be incorporated singly, or in combination, into the nucleic acid molecules of the present invention. In one embodiment, for example, a nucleic acid of the invention may comprise a modified sugar and a modified phosphate backbone. In another embodiment, a nucleic acid of the invention may comprise modifications to sugar, base and phosphate backbone.

"Oligonucleotide" refers generally to polynucleotides of between 5 and about 100 nucleotides of single- or double-stranded nucleic acid, typically DNA. Oligonucleotides are also known as oligomers or oligos and may be isolated from genes, or synthesized (e.g., chemically or enzymatically) by methods known in the art. A "primer" refers to an oligonucleotide, usually single-stranded, that provides a 3'-hydroxyl end for the initiation of enzyme-mediated nucleic acid synthesis.

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. "Polypeptides" usually comprise at least about 100 to about 1000 amino acids in length, more typically at least about 150 to about 600 amino acids, and frequently at least about 200 to about 500 amino acids. "Proteins" include single polypeptides as well as complexes of multiple polypeptide chains, which may be the same or different. Multiple chains in a protein may be characterized by secondary, tertiary and quaternary structure as well as the primary amino acid sequence structure; may be held together, for example, by disulfide bonds; and may include post-synthetic modifications such as, without limitation, glycosylation, phosphorylation, truncations or other processing. Antibodies such as IgG proteins, for example, are typically comprised of four polypeptide chains (i.e., two heavy and two light chains) that are held together by disulfide bonds. Furthermore, proteins may include additional components such as associated metals (e.g., iron, copper and sulfur), or other moieties. The definitions of peptides, polypeptides and proteins include, without limitation, biologically active and inactive forms; denatured and native forms; as well as variant, modified, truncated, hybrid, and chimeric forms thereof. The peptides, polypeptides and proteins of the present invention may be derived from any source or by any method, including, but not limited to extraction from naturally occurring tissues or other materials; recombinant production in host organisms such as bacteria, fungi, plant, insect or animal cells; and chemical synthesis using methods that will be well known to the skilled artisan.

"Polyclonal antibodies" or "antisera" are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants. Polyclonal antibodies may also be derived from the sera of humans or non-human animals exposed to a pathogen or vaccinated against a pathogen using a commercially available or experimental vaccine. An antiserum against TB (Mtb), for example, may be obtained from a human patient vaccinated with a TB vaccine, or from an animal, such as a mouse, rabbit, goat or sheep immunized with Mtb bacteria or a Mtb preparation.

"Monoclonal antibodies," which are abbreviated MAb, are homogeneous populations of antibodies to a particular antigen, may be obtained by any technique that provides for the production of antibody molecules by continuous cell lines in culture. These include, but are not limited to the hybridoma technique of Kohler and Milstein, *Nature,* 256:495-7 (1975); and U.S. Pat. No. 4,376,110, the human B-cell hybridoma technique (Kosbor, et al., *Immunology Today,* 4:72 (1983); Cote, et al., *Proc. Natl. Acad. Sci. USA,* 80:2026-30 (1983), and the EBV-hybridoma technique (Cole, et al., in Monoclonal Antibodies And Cancer Therapy, Alan R. Liss, Inc., New York, pp. 77-96 (1985)). Such antibodies may be of any immunoglobulin class including IgG, IgM, IgE, IgA, IgD and any subclass thereof. The hybridoma producing the MAb of this invention may be cultivated in vitro or in vivo. Production of high titers of MAbs in vivo makes this a presently preferred method of production.

In addition, techniques developed for the production of "chimeric antibodies" (Morrison, et al., *Proc. Natl. Acad. Sci.,* 81:6851-6855 (1984); Takeda, et al., *Nature,* 314:452-54 (1985)) by splicing the genes from a mouse antibody molecule of appropriate antigen specificity together with genes from a human antibody molecule of appropriate biological activity can be used. A chimeric antibody is a molecule in which different portions are derived from different sources, such as those having a variable region derived from a murine MAb and a human immunoglobulin constant region. Humanized antibodies can also be generated in which certain parts (e.g., framework regions) of a non-human antibody are altered to make the antibody more like a human antibody, while retaining antigen binding features of the parent molecule.

Alternatively, techniques described for the production of single chain antibodies (U.S. Pat. No. 4,946,778; Bird, *Science* 242:423-26 (1988); Huston, et al., *Proc. Natl. Acad. Sci. USA,* 85:5879-83 (1988); and Ward, et al., *Nature,* 334:544-46 (1989)) can be adapted to produce single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the Fab fragments that can be produced by papain digestion of the antibody molecule, the F(ab')$_2$ fragments that can be produced by pepsin digestion of the antibody molecule and the Fab' fragments that can be generated by reducing the disulfide bridges of the F(ab')$_2$ fragments. Alternatively, Fab expression libraries may be constructed (Huse, et al., *Science,* 246:1275-81 (1989)) to allow rapid and easy identification of monoclonal Fab fragments with the desired specificity.

The term "hapten" as used herein, refers to a small proteinaceous or non-protein antigenic determinant that is capable of being recognized by an antibody. Typically, haptens do not elicit antibody formation in an animal unless part of a larger species. For example, small peptide haptens are frequently coupled to a carrier protein such as keyhole limpet hemocyanin in order to generate an anti-hapten antibody response. "Antigens" are macromolecules capable of generating an antibody response in an animal and being recognized by the resulting antibody. Both antigens and haptens comprise at least one antigenic determinant or "epitope," which is the region of the antigen or hapten that binds to the antibody. Typically, the epitope on a hapten is the entire molecule.

By the terms "specifically binding" and "specific binding" as used herein is meant that an antibody or other molecule, binds to a target such as an antigen, with greater affinity than it binds to other molecules under the specified conditions of the present invention. Antibodies or antibody fragments, as known in the art, are polypeptide molecules that contain regions that can bind other molecules, such as antigens. In various embodiments of the invention, "specifically binding" may mean that an antibody or other specificity molecule, binds to a target molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. Whenever a range appears herein, as in "1-10 or one to ten, the range refers without limitation to each integer or unit of measure in the given range. Thus, by 1-10 it is meant that each of 1, 2, 3, 4, 5, 6, 7, 8, 9, 10 and any subunit in between.

"Immunogenic compositions" of the present invention are preparations that, when administered to a human or non-human animal, elicit a humoral and/or cellular immune response. "Vaccine," as used herein, refers to immunogenic compositions that are administered to a human or non-human patient for the prevention, amelioration or treatment of diseases, typically infectious diseases. "Traditional vaccines" or "whole vaccines" typically may be live, attenuated or killed microorganisms, such as bacteria or viruses. Vaccines also encompass preparations that elicit or stimulate an immune response that may be useful in the prevention, amelioration or treatment of non-infectious diseases. For example, a cancer cell vaccine may be administered to stimulate or supplement a patient's immune response to neoplastic disease. "Subunit vaccines" may be prepared from purified or partially purified proteins or other antigens from a microorganism, cancer cell or other vaccine target. The term "recombinant vaccine" refers to any vaccine that is prepared using recombinant DNA technology and includes certain subunit vaccines (for example, where subunits are cloned and expressed in vitro prior to administration) and "polynucleotide vaccines" such as DNA vaccines that may encode immunogenic polypeptides. Vaccines typically contain at least one immunogenic component (e.g. a cell, virus, polypeptide, polynucleotide, and the like) but may also include additional agents such as adjuvants, which may enhance or stimulate the patient's immune response to the immunogenic component. In certain embodiments, vaccines or components of vaccines may be conjugated e.g. to a polysaccharide or other molecule, to improve stability or immunogenicity of one or more vaccine components.

As used herein, the term "promoter" refers to a DNA sequence having a regulatory function, which is recognized (directly or indirectly) and bound by a DNA-dependent RNA polymerase during the initiation of transcription. Promoters are typically adjacent to the coding sequence of a gene and extend upstream from the transcription initiation site. The promoter regions may contain several short (<10 base pair) sequence elements that bind transcription factors, generally located within the first 100-200 nucleotides upstream of the transcription initiation site. Sequence elements that regulate transcription from greater distances are generally referred to as "enhancers" and may be located several hundred or thousand nucleotides away from the gene they regulate. Promoters and enhancers may be cell- and tissue-specific; they may be developmentally programmed; they may be constitutive or inducible e.g., by hormones, cytokines, antibiotics, or by physiological and metabolic states. For example, the human metallothionein (MT) promoter is upregulated by heavy metal ions and glucocorticoids. Inducible promoters and other elements may be operatively positioned to allow the inducible control or activation of expression of the desired TAP fragment. Examples of such inducible promoters and other regulatory elements include, but are not limited to, tetracycline, metallothionine, ecdysone, and other steroid-responsive promoters, rapamycin responsive promoters, and the like (see e.g., No, et al., *Proc. Natl. Acad. Sci. USA,* 93:3346-51 (1996); Furth, et al., *Proc. Natl. Acad. Sci. USA,* 91:9302-6 (1994)). Certain promoters are operative in prokaryotic cells, while different promoter sequences are required for transcription in eukaryotic cells. Additional control elements that can be used include promoters requiring specific transcription factors, such as viral promoters that may require virally encoded factors. Promoters can be selected for incorporation into TAP fragments based on the intended use of the polynucleotide, as one skilled in the art will readily appreciate. For example, if the polynucleotide encodes a polypeptide with potential utility in human cells, then a promoter capable of promoting transcription in mammalian cells can be selected. Typical mammalian promoters include muscle creatine kinase promoter, actin promoter, elongation factor promoter as well as those found in mammalian viruses such as CMV, SV40, RSV, MMV, HIV, and the like. In certain embodiments, it may be advantageous to incorporate a promoter from a plant or a plant pathogen (e.g., cauliflower mosaic virus promoter), a promoter from a fungus such as yeast (e.g., Gal 4 promoter), a promoter from a bacteria or bacterial virus, such as bacteriophage lambda, T3, T7, SP6, and the like.

The term "terminator" refers to DNA sequences, typically located at the end of a coding region, that cause RNA polymerase to terminate transcription. As used herein, the term "terminator" also encompasses terminal polynucleotide sequences that direct the processing of RNA transcripts prior to translation, such as, for example, polyadenylation signals. Any type of terminator can be used for the methods and compositions of the invention. For example, TAP terminator sequences can be derived from a prokaryote, eukaryote, or a virus, including, but not limited to animal, plant, fungal, insect, bacterial and viral sources. In one embodiment, artificial mammalian transcriptional terminator elements are used. A nonexclusive list of terminator sequences that may be used in the present invention include the SV40 transcription terminator, bovine growth hormone (BGH) terminator, synthetic terminators, rabbit β-globin terminator, and the like. Terminators can also be a consecutive stretch of adenine nucleotides at the 3' end of a TAP fragment.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "serodiagnostic test" or grammatical equivalents herein is meant diagnostic tests to detect Mtb by serum of infected organisms, animals or patients.

By "diagnostic test" or grammatical equivalents herein is meant an assay or test to detect Mtb by any scientific technique from infected organisms, animals or patients.

Overview

The present invention generally relates to Mtb polypeptide libraries, methods of determining the immunogenic effect of Mtb polypeptides, and methods of developing vaccines against Mtb, as well as immunogenic and pharmaceutical compositions. The invention also provides immunogenic Mtb polypeptides and mixtures of polypeptides, polynucleotides encoding immunogenic Mtb polypeptides and immunogenic compositions comprising Mtb polypeptides or polynucleotides.

Polypeptide Libraries

According to a method of the present invention, a library or array of Mtb polypeptides, oligonucleotides, or polynucleotides is generated. The immunogenicity of individual polypeptides in the library or array is determined by immunological screening where suitable, highly immunogenic Mtb polypeptides are selected for vaccine development. Conveniently, individual polypeptides in the library may be arranged in an array to facilitate screening in a rapid and high throughput manner.

The term "array" includes any arrangement wherein a plurality of different molecules, compounds or other species are contained, held, presented, positioned, situated, or supported. Arrays can be arranged on microtiter plates, such as 48-well, 96-well, 144-well, 192-well, 240-well, 288-well, 336-well, 384-well, 432-well, 480-well, 576-well, 672-well, 768-well, 864-well, 960-well, 1056-well, 1152-well, 1248-well, 1344-well, 1440-well, or 1536-well plates, tubes, slides, chips, flasks, or any other suitable laboratory apparatus. In one embodiment, molecules arranged in an array are peptides, polypeptides or proteins. In another embodiment, the molecules are oligonucleotides or polynucleotides. In one aspect of the invention, polypeptides or polynucleotides in solution are arranged in 96 well plate arrays. In another embodiment, polypeptides or polynucleotides are immobilized on a solid support in an array format. Furthermore, an array can be sub-divided into a plurality of sub-arrays, as for example, where multiple 96-well plates (each an individual sub-array) are required to hold all of the samples of a single, large array.

The term "library" is likewise to be construed broadly, and includes any non-naturally occurring collection of molecules, whether arranged or not. A library therefore encompasses an array but the two terms are not necessarily synonymous.

TAP Technology

Libraries of Mtb polypeptides may be prepared by any method known in the art. Conveniently, GTS' patented Transcriptionally Active PCR ("TAP") products can be used to amplify DNA in preparation for producing Mtb polypeptide libraries. With TAP technology, a particular polynucleotide of interest can be made transcriptionally active and ready for expression in less than one day. "TAP fragments" are transcriptionally active coding sequences prepared using TAP technology, and the two terms can be used interchangeably. TAP fragments encompass polynucleotides that can be readily expressed, for example, by transfection into animal cells or tissues by any nucleic acid transfection technique, without the need for subcloning into expression vectors or purification of plasmid DNA from bacteria. TAP fragments can be synthesized by amplification (e.g., polymerase chain reaction, or PCR) of any polynucleotide of interest using nested oligonucleotide primers. Two polynucleotide sequences are typically incorporated into TAP fragments, one of which comprises an active transcriptional promoter and the other comprises a transcriptional terminator.

TAP fragments and methods of making the same are described in detail in U.S. Pat. No. 6,280,977, entitled "Method for Generating Transcriptionally Active DNA Fragments" which is hereby incorporated by reference in its entirety. In one embodiment, methods for creating TAP fragments include the steps of: i) designing oligonucleotide primers; ii) amplifying TAP primary fragments; and iii) amplifying TAP expression fragments. FIG. 1 illustrates one method for generating TAP fragments.

TAP fragments can be prepared using custom oligonucleotide primers designed to amplify a target polynucleotide sequence of interest from the Mtb genome. Primers complementary to the 5' and 3' ends of the polynucleotide of interest can be designed and synthesized using methods well known in the art, and can include any suitable number of nucleotides to permit amplification of the coding region. Typically, the polynucleotide sequence of interest is an open reading frame (ORF) that consists of an uninterrupted stretch of triplet amino acid codons, without stop codons. In certain embodiments, the polynucleotide is a Mtb polypeptide-encoding sequence.

In one embodiment of the invention, 5'-custom oligonucleotide primers of about 41, 42, 43, 44, 45 or 46 nucleotides are designed and synthesized; about 6 nucleotides of which comprise the 5'-TAP end universal sequence 5'-GAAG-GAGATATACCATGCATCATCATCATCATCAT-3' (SEQ ID NO: 84) and about 15 to 20 nucleotides are complementary to the Mtb sequence. Accordingly, the target-specific sequence can be, for example, about 15, 16, 17, 18, 19, or 20 nucleotides in length. The 5' oligonucleotide may also incorporate a Kozak consensus sequence (A/GCCAUGG) near an ATG start codon (initiator methionine) for more efficient translation of mRNA. In one embodiment, an ATG start codon is included in the target-specific primer sequence. In another embodiment, an ATG start codon is incorporated into the custom 5'-oligonucleotide when the target sequence encoding a polypeptide of interest lacks an initiation methionine codon at its 5' end.

In one embodiment of the invention, 3'-custom oligonucleotide primers comprise about 35, 36, 37, 38, 39, 40, 41, 42, 43, 44, or 45 nucleotides; of these, about 20 nucleotides comprise the 3'-TAP end universal sequence 5'-TGATGATGAGAAC-CCCCCCC-3' (SEQ ID NO: 85) and about 20 nucleotides are complementary to the target Mtb sequence. In one aspect, a stop codon sequence, can be added to the end of the target Mtb sequence to achieve proper translational termination by incorporating a TCA, TTA, or CTA into the 3'-custom oligonucleotide.

Bioinformatics Analysis of Mtb Polynucleotides

In one embodiment of the invention, a bioinformatics approach is used to identify, prioritize and select Mtb genes, coding sequences, ORFs and other sequences of interest for TAP amplification and to design custom 5' and 3' oligonucleotide primers. According to this approach, a database of Mtb genomic information is compiled from available nucleic acid and amino acid sequence information, including the polynucleotide, gene, locus, polypeptide, and protein names, locations and sizes. In certain embodiments, the location of known coding sequences is included in the database. The sequence information may also be analyzed for unidentified ORFs and putative coding sequences. Any method can be used to identify ORFs and coding sequences including free or commercially available sequence analysis software. For example, the GLIMMER program may be used to predict putative coding regions or genes in prokaryotic nucleotide sequences. See e.g., Salzberg et al., *Nucleic Acids Res.* 26: 544-548 (1998); Delcher, et al., *Nucleic Acids Res.* 27:4636-4641(1999).

In certain aspects of the invention, the genome database includes the entire genomic DNA sequence of Mtb . In one embodiment, the sequence information is obtained from information that is in the public domain. In other embodiments, some or all of the sequence information can be obtained by nucleotide and/or amino acid sequencing.

As previously described in U.S. Ser. No. 10/159,428, which is hereby incorporated by reference in its entirety, the methods of the present invention, particularly TAP technology, enable the skilled artisan to prepare a library representing all or substantially all of the polypeptides expressed in an organism or cell type. In certain embodiments of the present invention, however, it may be preferable to prepare a library of polypeptides with selected properties. Thus, one aspect of the present invention utilizes a set of ranking criteria to identify polypeptides predicted to have properties desirable e.g., for vaccine development. Polypeptide ranking criteria, which may be identified using bioinformatics tools, include but are not limited to, the presence of membrane domains, ORF size, secreted proteins signatures, signal sequences, hydrophobicity, B-cell and T-cell epitopes, homology to human proteins, protein and gene expression levels. The ranking criteria may be assigned a numerical score based on relative importance. Coding regions or putative coding regions identified in the database of Mtb sequences are then scored using the numerical ranking criteria and the sum of the scores for each sequence is used to establish a rank order. According to this aspect of the invention, primers are designed to amplify Mtb-polynucleotides in rank order. A library may be constructed, for example, from the top 5%, 10%, 20%, 30%, 40% or 50% by rank of Mtb polynucleotides.

Amplification of Mtb Polynucleotides

Using the custom 5' and 3' oligonucleotide primers, TAP primary fragment may be amplified by methods well known in the art. The term "TAP primary fragment" refers to an amplified Mtb polynucleotide, and in one embodiment relates to a polynucleotide sequence that has been amplified but is not transcriptionally active. Generation of TAP primary fragments involves performing PCR, which generates a polynucleotide fragment that contains the Mtb polynucleotide sequence with 5'- and 3'-TAP universal end sequences and may contain other sequences incorporated into the custom 5' and 3' oligonucleotide primers. The 5'- and 3'-TAP universal end sequences are particularly useful for incorporating one or more nucleotide sequences into TAP primary fragment that confer transcriptional activity. In one embodiment, these sequences can include TAP Express™ promoter and terminator fragments (e.g., SEQ ID NOS: 2-7). The skilled artisan will be familiar with methods for amplifying polynucleotides, (e.g. by using PCR) and can adjust the above methods in order to optimize the amplification reaction.

An additional step in the generation of TAP fragments involves incorporating at least one polynucleotide sequence that confers transcriptional activity into the TAP primary fragment. Typically, at least one polynucleotide sequence is incorporated by performing a second PCR reaction. Examples of polynucleotide sequences that confer transcriptional activity are promoter sequences (e.g., prokaryotic Pribnow boxes and eukaryotic TATA box sequences) binding sites for transcription factors, and enhancers. In one embodiment, one promoter and one terminator sequence are added to the TAP fragment. These promoter and terminator sequences can be obtained in numerous ways. For example, one can use restriction enzyme digestion of commercially available plasmids and cDNA molecules, or one can synthesize these sequences with an automated DNA synthesizer by methods well known in the art.

The end product of the second PCR reaction is referred to as a "TAP expression fragment," which is a transcriptionally active polynucleotide, and which is generally a transcriptionally active coding sequence. In certain embodiments, the TAP expression fragments are used directly for in vivo or in vitro (e.g. cell-free) expression. In other embodiments, TAP expression fragments are transfected into cultured cells or injected into animals.

Generating TAP fragments is a rapid and efficient way of making a large number of polynucleotide sequences transcriptionally active. Accordingly, a plurality of different genes from Mtb can be made transcriptionally active using TAP technology. Thus, a library representing all, substantially all, or a selected subset of the coding sequences in the Mtb genome can be constructed using TAP technology.

TAP Tags and Linker Molecules

As described above, TAP technology provides powerful methods for amplifying and expressing Mtb polynucleotides. Coding sequences can be rendered transcriptionally active by the PCR-mediated addition of promoter sequences, enhancers, terminators and other regulatory sequences.

In addition, Mtb polynucleotides can be amplified with additional coding or non-coding sequences that can facilitate rapid screening, characterization, purification and study of the polypeptides that they encode. These additional sequences include, for example, reporter genes, affinity tags, antibody tags, PNA binding sites, secretory signals, and the like.

According to the present invention, Mtb polynucleotides can be synthesized with an epitope tag. An "epitope tag" is a short stretch of polynucleotide sequence encoding an epitope. In one embodiment, this epitope is preferably recognized by a well-characterized antibody. By incorporating an epitope tag into TAP fragments, the Mtb polynucleotide of interested can be fused in-frame to an epitope-encoding sequence. Expression of an epitope-tagged TAP fragment produces a fusion protein comprising a tagged Mtb polypeptide. Suitable epitope tags will be well known to those skilled in the art, including the hemagglutinin (HA), the 6×His epitope tag, and the Flag epitope tag. The HA epitope tag is well characterized and highly immunoreactive. Upon transfection of an HA-tagged TAP fragment into cells, the resulting HA-tagged polypeptides can be identified with commercially available anti-HA antibodies. Epitope tagging of TAP fragments is useful for rapidly and conveniently detecting expression of TAP fragments. Epitope tagging of TAP fragments can also help determine the intracellular distribution of Mtb polypeptides and help characterize and purify the Mtb polypeptide. Furthermore, epitope-tagged expression products can be quickly captured and/or purified using antibodies specific for the specific epitope. Antibodies directed against the HA epitope can used in the full range of immunological techniques for detection and analysis of tagged polypeptides including but not limited to Western blotting, ELISAs, radioimmune assays, immunoprecipitation, immunocytochemistry and imnuunofluorescence, fluorescence assisted cell sorting (FACS) and immunoaffinity purification of the desired fusion polypeptides.

The present invention also provides Mtb polypeptides fused to affinity tags. For example, a polynucleotide sequence encoding a histidine tag can be incorporated into the TAP fragment to enable the expressed gene product to be conveniently purified. These His tags consist of six consecutive histidine residues (6×His) and are a powerful tool for recombinant polypeptide purification. The 6×His tag interacts with metals, such as nickel. Thus, polypeptides fused to a 6×His tag can be purified by metal affinity chromatography, for example, using a nickel nitrilotriacetic (Ni-NTA) resin. The 6×His tag is much smaller than most other affinity tags and is uncharged at physiological pH. It rarely alters or contributes to polypeptide immunogenicity, rarely interferes with polypeptide structure or function, does not interfere with secretion, does not require removal by protease cleavage, and is compatible with denaturing buffer systems. Accordingly, this tag is a powerful adjunct to expression and purification of recombinant proteins.

In one aspect of this embodiment, TAP primers can be designed to include the nucleotide sequence encoding the 6×His epitope tag: to add the 6×His epitope to the 5' end of a Mtb polynucleotide, a sequence encoding histidine residues can be included along with the promoter-containing primer; to add the 6×His epitope to the 3' end, the His sequence can be included in the terminator-containing primer.

Commercially available nickel affinity resins can be used to purify 6×His tagged polypeptides. For example, the well-established QIAexpress Protein Expression and Purification Systems are based on the remarkable selectivity and affinity of patented nickel-nitrilotriacetic acid (Ni-NTA) metal-affinity chromatography matrices for polypeptides tagged with 6 consecutive histidine residues (6×His tag) available from QIAGEN (Seattle, Wash.). The QLAexpress System is based on the remarkable selectivity of Ni-NTA (nickel-nitrilotriacetic acid) for polypeptides with an affinity tag of six consecutive histidine residues—the 6×His tag. This technology allows purification, detection, and assay of almost any 6×His-tagged polypeptide from any expression system. Polypeptides with a 6×His tag can be purified through nickel nitrilotriacetic (Ni-NTA) resin.

The HA and the 6×His epitope embodiments are not to be construed as limiting, and are provided for illustrative purposes only. Those skilled in the art will appreciate that any type of tag can be attached to the expressed products such as for example, a 7×, 8×, 9×, or 10×histidine tag, GST tag, fluorescent protein tag, and the like.

In addition to providing a convenient means for detection and purification of Mtb polypeptides, various tags can provide a "linker" through which the polypeptides of the invention can be immobilized on a solid support. The term "linker molecule," as used herein, encompasses any molecule that is capable of immobilizing the polypeptides to a solid support.

TAP Fragment with Secretory Signal

For many gene therapy and DNA vaccine applications it may be beneficial for the gene product to be secreted from the transfected cells. Thus, one embodiment of the invention provides a version of the TAP system designed to express Mtb polypeptides containing a fused a secretory signal. A commonly used signal peptide is the first 23 amino acids from human tissue plasminogen activator (tPA) with the coding sequence as follows: ATG GAT GCA ATG AAG AGA GGG CTC TGC TGT GTG CTG CTG CTG TGT GGA GCA GTC TTC GTT TCG CCC AGC. (SEQ ID NO: 1) This sequence can be built into the TAP promoter fragment to create a new TAP fragment in a fashion similar to the construction of the tagged polypeptides described above.

Incorporating TAP Fragments into a Plasmid Vector

Once the function or immunogenicity of an Mtb polypeptide is identified, it may be of desirable to clone the TAP fragment into a plasmid or other vector to facilitate further gene characterization and manipulation.

Standard cloning techniques can involve the use of restriction enzymes to digest the plasmid and the gene fragment to be inserted. Annealing and ligation of the compatible ends can lead to insertion of the gene into the vector. An alternative method of restriction ends-directed cloning is to prepare a linearized plasmid with T overhangs on the 3' ends of the double-stranded DNA to accommodate DNA fragments amplified with the aid of specific polymerases through PCR. This method is sometimes called "T/A cloning". Other methods of cloning TAP fragments will be well known to those of skill in the art.

In certain embodiments, the TAP Cloning systems, methods, and kits can further simplify the cloning process by taking advantage of the universal 5' and 3' sequences that are present on the TAP Express fragment after the first or second PCR step. These regions overlap with the end sequences of our linearized TAP Express Cloning Vector. When the TAP fragment and the linearized plasmid are mixed together and directly electroporated into TAP Express Electro-Comp cells, endogenous bacterial recombinase activity recombines the two DNA fragments resulting in a plasmid with the inserted TAP Express fragment. This process can replace conventional cloning with two simple PCR steps. In some embodiments it does not require cutting, pasting and ligating DNA fragments. In addition, this process can be highly suited for fast and convenient cloning of TAP PCR fragments without having to resort to restriction enzymes, DNA ligase, Topoisomerase or other DNA modifying enzymes. "TAP" systems, vectors and cells are readily available from Gene Therapy Systems, Inc., San Diego, Calif.

GeneGrip PNA compatible TAP system can also be used to couple polypeptides onto DNA through PNA-Dependent Gene Chemistry, thereby avoiding many of the limitations of previously described methodologies. GeneGrip is available through Gene Therapy Systems, Inc., San Diego, Calif. This approach takes advantage of the property of peptide nucleic acids (PNA) to hybridize with duplex DNA in a sequence specific and very high affinity manner. PNA binding sites can be used for attaching a series of peptides onto DNA in order to target the transfected plasmid and improve transgene expression, for example. This can facilitate a rational approach to improve the efficiency and efficacy of gene delivery by adding elements intended to increase nuclear uptake, facilitate endosomal escape, or target gene delivery to the cell surface or to intracellular receptors.

Incorporating a GeneGrip site into TAP enables peptide nucleic acids (PNAs) to be hybridized to the TAP gene product. Ligands can then be attached to the PNA in order to improve the bioavailability and DNA vaccine potency of the gene.

System for Performing TAP Method

In another embodiment of the invention, a system can be used to perform every step involved in generating TAP fragments from a Tb, and in particular the Mtb genome. Additionally, each individual step is capable of being controlled by a system. For example, a system can design customized PCR primers, obtain said primers, perform PCR reactions utilizing TAP technology, attach promoters and terminators, and attach sequences that encode linker molecules to the primary or expression fragment. The system can be either automated or non-automated. In one embodiment of the invention, the system comprises a computer program linked to robotic technologies for rapid and high throughput gene amplification of the genome.

Expression of the TAP Fragment

TAP fragments can be used directly as templates in various expression systems in order to obtain the corresponding polypeptide for each coding sequence in the Mtb genome. The invention provides simple, efficient methods for generating TAP fragments from Mtb that can be readily transfected into animal cells or tissues by any nucleic acid transfection technique. The methods of the invention can avoid the need for subcloning into expression vectors and for purification of plasmid DNA from bacteria. As skilled artisans can appreciate, TAP fragments can be rapidly expressed using in vivo or in vitro (e.g. cell-free) expression systems. For example, the amplified TAP fragments can be directly transfected into a eukaryotic or prokaryotic cell for expression. Examples of eukaryotic cells that can be used for expression include mammalian, insect (e.g. Baculovirus expression systems), yeast (e.g. *Picchia pastoris*), and the like. An example of a prokaryotic cell expression system includes *E. coli*.

Alternatively, expression can be accomplished in cell-free systems, for example, a T7 transcription and translation system. Cell-free translation systems can include extracts from rabbit reticulocytes, wheat germ and *Escherichia coli*. These systems can be prepared as crude extracts containing the macromolecular components (30S, 70S or 80S ribosomes, tRNAs, aminoacyl-tRNA synthetases, initiation, elongation and termination factors, etc.) required for translation of exogenous RNA. To promote efficient translation, each extract can be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

The use of TAP technology allows skilled artisans to rapidly express polypeptides from a plurality of polynucleotides. After a particular Mtb polynucleotide of interest is rendered transcriptionally active, other Mtb polynucleotides can also be made to be transcriptionally active according to the methods of the invention. Accordingly, in one embodiment of the invention, a plurality of polynucleotides from Mtb are amplified and expressed in order to generate a library or array of Mtb polypeptides.

Other embodiments of the invention relate to expressing the product of a Mtb polynucleotide that encodes an epitope tag, affinity tag or other tags, and which may function as linkers. A polynucleotide sequence encoding a linker molecule can be incorporated into a TAP primary fragment or a TAP expression fragment. Accordingly, the linker molecule can be expressed as a fusion to the Mtb polypeptide.

The generation of Mtb polypeptide libraries according to the methods of the invention allows skilled artisans to easily use them in subsequent research and study. For example, it is possible to organize the expressed Mtb polypeptides into an array for further analysis. The expressed polypeptide arrays can be screened in order to identify, for example, new vaccine and drug targets against microbial, neoplastic disease and the like. The expressed polypeptides can be used to screen antibody libraries, to develop unique research reagents, for functional proteomic studies, and the like. These steps can be rapidly accomplished at rates far exceeding traditional methods.

Adapter Technology

In addition to amplifying Mtb polynucleotides of interest using TAP technology, the present invention also encompasses amplifying Mtb polynucleotides using "adapter technology". In some embodiments adapter technology is performed using a one-step PCR reaction. The term "adapter technology" as used herein relates to methods of cloning a desired polynucleotide into a vector by flanking a desired nucleic acid sequence, a Mtb TAP fragment for example, with first and second adapter sequences. The resulting fragment can be contacted with the vector having sequences homologous to the first and second adapter sequences under conditions such that the nucleic acid fragment is incorporated into the vector by homologous recombination in vivo in a host cell. Accordingly, adapter technology allows for fast and enzyme-less cloning of nucleic acid fragments into vectors and can also be used for forced cloning selection for successful transformation. Adapter technology is described in more detail in U.S. patent application Ser. No. 09/836,436, entitled "Fast and Enzymeless Cloning of Nucleic Acid Fragments", U.S. Pat. No. 6,936,470, entitled "Rapid and Enzymeless Cloning of Nucleic Acid Fragments", and PCT Application No. PCTUS 02/12334, all of which are hereby incorporated by reference in their entirety.

The nucleic acid fragment can be incorporated into any vector using adaptor technology. In certain embodiments, the vector that the fragment is incorporated into can be, for example, a plasmid, a cosmid, a bacterial artificial chromosome (BAC), and the like. The plasmid can be CoE1, PR100, R2, pACYC, and the like. The vector can also include a functional selection marker. The functional selection marker can be, for example, a resistance gene for kanamycin, ampicillin, blasticidin, carbonicillin, tetracycline, chloramphenicol, and the like. The vector further can include a dysfunctional selection marker that lacks a critical element, and wherein the critical element is supplied by said nucleic acid fragment upon successful homologous recombination. The dysfunctional selection marker can be, for example, kanamycin resistance gene, ampicillin resistance gene, blasticidin resistance gene, carbonicillin resistance gene, tetracycline resistance gene, chloramphenicol resistance gene, and the like. Further, the dysfunctional selection marker can be, for example, a reporter gene, such as the lacZ gene, and the like.

The vector can include a negative selection element detrimental to host cell growth. The negative selection element can be disabled by said nucleic acid fragment upon successful homologous recombination. The negative selection element can be inducible. The negative selection element can be, for example, a mouse GATA-1 gene. The vector can include a dysfunctional selection marker and a negative selection element.

The host cell used in adapter technology can be a bacterium. The bacterium can be capable of in vivo recombination. Examples of bacterium include JC8679, TB1, DHα, DH5, HB101, JM101, JM109, LE392, and the like. The plasmid can be maintained in the host cell under the selection condition selecting for the functional selection marker.

The first and second adapters can be any length sufficient to bind to the homologous sequences of the vector such that the desired nucleic acid sequence is incorporated into the vector. The first and second adapter sequences can be, for example, at least 11 bp, 12 bp, 13, bp, 14 bp, 15 bp, 16 bp, 17 bp, 18 bp, 19 bp, 20 bp, 21 bp, 22 bp, 23 bp, 24 bp, 25 bp, 26 bp, 27bp, 28 bp, 29 bp, 30bp,31 bp, 32 bp, 33 bp, 34bp, 35 bp, 36bp, 37 bp, 38 bp, 40 bp, 50 bp, 60 bp and the like. Furthermore, the first and second adapter sequences can be greater than 60 bp.

The first and second adapter sequences further can include a functional element. The functional element can include a promoter, a terminator, a nucleic acid fragment encoding a selection marker gene, a nucleic acid encoding a linker molecule, a nucleic acid fragment encoding a known protein, a fusion tag, a nucleic acid fragment encoding a portion of a selection marker gene, a nucleic acid fragment encoding a growth promoting protein, a nucleic acid fragment encoding a transcription factor, a nucleic acid fragment encoding an autofluorescent protein (e.g. GFP), and the like.

When the common sequences on both the 5' and 3' ends of the nucleic acid fragment are complimentary with terminal sequences in a linearized empty vector, and the fragment and linearized vector are introduced, by electroporation, for example, together into a host cell, they recombine resulting in a new expression vector with the fragment directionally inserted. In alternative embodiments the host cell can include the linearized empty vector so that only the nucleic acid fragment is introduced into the host cell. It should be noted that in alternative embodiments of the present invention the vector can be circularized, and as used herein a vector can be either linearized or circular. The host cell is converted into an expression vector through homologous recombination. In principle this approach can be applied generally as an alternative to conventional cloning methods.

A nucleic acid fragment having first and second adapter sequences can be generated by methods well known to those of skill in the art. For example, a gene of interest with known 5' and 3' sequences undergoes PCR along with overlapping 5' and 3' priming oligonucleotides. The priming oligonucleotides can be obtained by methods known in the art, including manufacture by commercial suppliers. A primary fragment with adapter sequences can be generated. The adapter sequences flanking the gene of interest can be homologous to sequences on a vector or to sequences from other 5' or 3' fragments to be used in a subsequent PCR.

In some embodiments of the invention, a particular polynucleotide of interest from *Mtb* can be amplified with an adapter sequence on both the 3' and 5' ends. In other embodiments adapters can be attached to a plurality of polynucleotides, for example every coding region in the Mtb genome. In certain embodiments adapters can make the desired coding regions transcriptionally active. Once incorporated into the desired vector, the Mtb coding region can be rapidly replicated and expressed, such that a plurality of Mtb 's genes, for example every gene, is expressed.

Pluralities of expression products can be stored in libraries or arrays and can be assayed for their immunogenic properties as will be discussed below. While most embodiments relating to the assay methodologies are discussed in terms of TAP technology, all of the following assays can be used on adapter technology expression products as well. Once the appropriate assays are conducted on the adapter technology expression products, methods of developing vaccines can be utilized. While most of the embodiments relating to developing vaccines, discussed below, pertain to TAP technology, all of the vaccine embodiments can also be used with polypeptide libraries and arrays resulting from adapter technology.

Identifying Immunogenic Polypeptides

Libraries and arrays of polypeptides, prepared through TAP or adapter technology with subsequent expression can be useful in the development of polypeptide or nucleic acid subunit vaccines. DNA vaccines are effective vaccines that are inexpensive to manufacture, easy and safe to deliver, and can be widely distributed. It has been found that plasmid DNA, when injected into mice without being associated with any adjuvant, can generate antibody and CTL responses to viral antigens encoded by the plasmid DNA, and elicit protective immunity against viral infection (Ulmer at al., *Science,* 259:1745, 1993). Starting from this, there have been reported many research results regarding the induction of humoral and cellular immune responses resulting from the introduction of DNA vaccines containing various viral genes in animal models (Chow et al., *J. Virol.,* 71:169, 1997; McClements et al., *Proc. Natl. Acad. Sci. USA,* 93:11414, 1996; Xiang et al., *Virology,* 199:132, 1994; Wang et al., *Virology,* 211:102, 1995; Lee etal., *Vaccine,* 17:473, 1999; Lee etal., *J. Virol.,* 72:8430, 1998). As well, DNA delivery by electroporation techniques has been well-described (Heller et al., *Expert Opin. Drug Deliv.* 2(2): 1-14, 2005)

One of the most difficult tasks in developing a DNA vaccine (or any recombinant subunit vaccine) to a pathogen such as Mtb, is the identification of antigens that can stimulate the most effective immune response against the pathogen, particularly when the genome of the organism is large.

A comprehensive means to accomplish this task, which is embodied by the present invention, is to obtain a plurality of polypeptides from the particular pathogen in the mode of a library or array. These polypeptides can be tested to determine their capability to evoke a humoral and/or a cell-mediated immune response. Polypeptides that evoke immunogenic responses can be tested individually or with other antigens for effectiveness as subunit vaccines. In addition, nucleic acids that encode identified antigenic polypeptides can be used alone or with other nucleic acids that encode antigens to develop a recombinant vaccine, such as a DNA vaccine, for the particular pathogen.

Mtb Scanning

Figure 2:
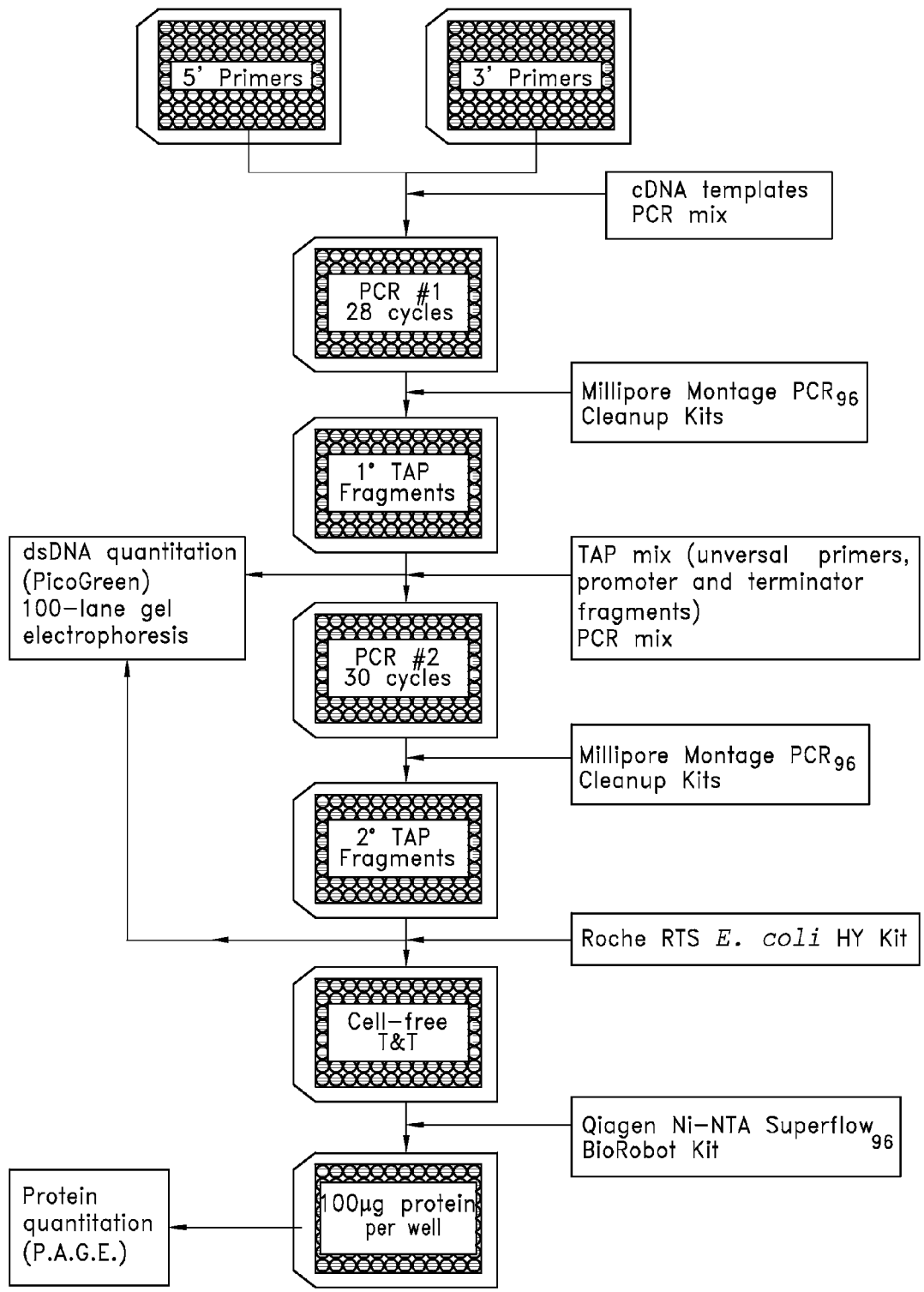
FIG. 2. displays a method of amplifying multiple genes using TAP technology, expressing said genes products, then purifying and quantifying the resulting polypeptides.

One embodiment of the invention, incorporates a Rapid High-Throughput Vaccine Antigen Scanning approach, using TAP Express, that is able to systematically screen and identify all, substantially all, or a subset of the antigens in Mtb that give rise to a humoral and cell-mediated immune response. The identification of the Mtb antigens allows for the development of a highly specific subunit vaccine FIG. 2 illustrates a method for amplifying multiple Mtb polynucleotides using TAP technology, expressing the gene products of the resultant TAP fragments, purifying, and quantifying the resulting polypeptides. FIG. 2 further illustrates a method of preparing polypeptides, which can be assayed to identify their ability to evoke a cell-mediated or humoral immune response.

In certain methods of developing a Mtb vaccine, a plurality of Mtb polynucleotides can be made transcriptionally active. In one embodiment, all of the open reading frames from *Mtb* genome can be made transcriptionally active using TAP technology. The present invention thus provides Mtb polynucleotides (SEQ ID NOS: 46-64, 110-121) that have been made transcriptionally active.

The resulting Mtb TAP fragments of the present invention can be purified and expressed in vitro or in vivo according to any method known in the art. The expression products, which encompass SEQ ID NOS: 65-83, 122-133, can be assayed by various methods to determine their ability to evoke a humoral and/or a cell-mediated immunogenic response. Polypeptides that are identified as capable of evoking an immune response can be used as candidates to develop polynucleotide or polypeptide subunit vaccines. The complete method will be described in more detail below.

According to one embodiment of the present invention, TAP fragments from Mtb are used to generate a DNA array, and then, if desired, a protein array. In certain embodiments, primers are designed for every gene in the Mtb genome. In another embodiment, designing the primers allows a skilled artisan to make any given Mtb polynucleotide transcriptionally active using TAP technology. In yet another embodiment, coding regions, ORFs and other polynucleotide sequences of interest are ranked according to and the top Mtb polynucleotides are made transcriptionally active using TAP technology.

As mentioned above, the custom PCR primers can be designed by using an automated system, such as a computerized robotics system. For example, in order to design custom primers for use in the TAP process, a robotic workstation can be interfaced with a dual Pentium III CPU (1.4 GHz) computer running the Linux operating system. In addition, a customized MySQL database can manage the input sequence data from GenBank and from other sources. This database can track all the operations, samples and analytical data generated by the robot. In another embodiment, PCR primers, PCR products and polypeptides can be tracked by the database. For example, PCR primers, PCR products and polypeptides can be tracked by using bar coded 96-well plates. While the embodiments below discuss using 96-well plates in certain embodiments, those skilled in the art can appreciate that any sized well plate can be used. For example, the well plates can consist of about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more wells. In addition to well plates, the PCR products and polypeptides can be tracked using any suitable receptacles, for example test tubes.

Custom oligonucleotide pairs of the present invention (SEQ ID NOS: 8 and 9; 10 and 11; 12 and 13; 14 and 15; 16 and 17; 18 and 19; 20 and 21; 22 and 23; 24 and 25; 26 and 27; 28 and 29; 30 and 31; 32 and 33; 34 and 35; 36 and 37; 38 and 39; 40 and 41; 42 and 43; 44 and 45; 86 and 87; 88 and 89; 90 and 91; 92 and 93; 94 and 95; 96 and 97; 98 and 99; 100 and 101; 102 and 103; 104 and 105; 106 and 107; 108 and 109), which are needed for the TAP PCR reactions, can be synthesized or obtained in order to perform the TAP technology. In certain embodiments, the Mtb genome sequence data and primer design software (e.g., Primer 3) can be used by the system to generate custom primer pairs for all, substantially all, or a subset of the genes in the Mtb genome. The primers can be organized into arrays of about 48, about 96, about 144, about 192, about 240, about 288, about 336, about 384, about 432, about 480, about 576, about 672, about 768, about 864, about 960, about 1056, about 1152, about 1248, about 1344, about 1440, or about 1536 5' primers and 3' primers according to polynucleotide size and GC content, such PCR reaction conditions can be optimized on a plate by plate basis. The present invention further contemplates that sequences for each of the custom Mtb primer pairs can be sent to an oligonucleotide synthesis provider (e.g., MWG Biotech, Inc., High Point, N.C.) where they can be synthesized. Synthesized primers can be organized and dispensed into bar-coded plates at a desired concentration, such as 100 pmole/μl, frozen and shipped to the practitioner. In one embodiment, 600 Mtb-specific PCR primers, which are capable of amplifying 300 Mtb coding sequences are designed, generated, ordered, and organized.

After obtaining or generating the custom Mtb PCR primers, the Mtb polynucleotides of interest can be amplified. In one embodiment, the primers can be organized into arrays of 96 5' primers and 96 3' primers according to polynucleotide size, and placed onto a robotic workstation. The robot can be programmed to generate a plate of about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 PCR reactions by mixing the appropriate 5' and 3' primers with Taq polymerase and Mtb genomic DNA. In addition to Taq, any thermally stable polymerase can be used in the PCR reactions. For example, Vent, Pfu, Tfl, Tth, and Tgo polymerases can be used. The robotic workstation can transfer the PCR reaction plate containing the mixed reagents to a PCR machine for amplification. In one embodiment, the robotic workstation can use a robotic arm to transfer the PCR reaction plate to the PCR machine.

The first TAP PCR procedure can be run for any number of cycles. In one embodiment, the PCR machine is run for about 20, 21, 22, 23, 24, 25, 26, 27, 28, 29, 30, 31, 32, 33, 34, 35, 36, 37, 38, 39, 40, or more cycles. The first TAP PCR reactions can be transferred robotically to a Millipore Montage 96-well cleanup kit, for example, when desired. Any method, kit or system can, however, be used to purify the PCR products from these reactions. According to one embodiment, a vacuum station of the robotic platform can carry out the purification step. In some embodiments, an aliquot of the resulting product can be transferred robotically to an analysis plate containing the Pico-Green fluorescent probe (Molecular Probes, Eugene, Oreg.) that reacts only with the dsDNA products.

Depending on the number of wells, the plate can be transferred to an about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more well fluorescent plate reader. The fluorescent signal can be compared to a standard curve to determine the amount of double stranded PCR product generated in this first PCR step. Persons with skill in the art can adjust the above methods in order to optimize their particular PCR reaction, should the need arise.

In addition to the first TAP PCR procedure, a second TAP PCR reaction can be performed to add at least one sequence that confers transcriptional activity to the primary TAP primary fragment. In one embodiment, a robot can be programmed to transfer an aliquot of each TAP primary fragment from the first TAP PCR reaction into a PCR reaction containing a promoter- and a terminator-containing primers. In a particular embodiment, the promoter can be a T7-his tag promoter sequence and the terminator can be a T7-His tag terminator sequence. Those with skill in the art can appreciate that any promoter or terminator sequence can be added to the primary transcript. In addition, any polynucleotide sequence that encodes a tag or linker allowing the expressed polypeptide to be detected or purified is also contemplated.

Like the first TAP PCR reaction, the second TAP PCR reaction can be run for any desired number of cycles. In one embodiment, the second TAP PCR reaction is run for about 20, 21, 22, 23, 24, 25, 26, 27, 28, 29, 30, 31, 32, 33, 34, 35, 36, 37, 38, 39, 40 cycles or more. Furthermore, any type of thermally stable polymerase can be used for the second TAP PCR reaction. In a particular embodiment the polymerase can be Taq. In some embodiments Vent, Pfu, Tfl, Tth, and Tgo polymerases can be used. The resulting TAP Express PCR fragments from the second PCR reaction can be cleaned by any kit, method or system. A particular kit that can be used to clean the resulting TAP fragments is a Millipore Montage 96-well cleanup kit. Additionally, as discussed above, the level of PCR product recovered can be determined using any detection agent, for example, Pico-Green.

The resulting TAP fragments can be expressed by using any method of gene expression. In one embodiment, the TAP fragments can be expressed using in vivo or in vitro (e.g. cell-free) systems. For example, the fragments can be directly transfected into any eukaryotic or prokaryotic cell for expression. Examples of eukaryotic cells that can be used for expression include mammalian, insect, yeast, and the like. An example of a prokaryotic cell expression system includes *E. Coli*. The TAP fragments can also be expressed by a cell-free system. According to one embodiment of the invention, the resulting TAP fragments can be expressed in a high-throughput cell-free expression machine, such as, for example, the Roche RTS (Rapid Translation System)-100. In a further embodiment, the TAP fragments can be incubated in Roche RTS 100 system at 30° C. for 5 hours. A person with skill in the art can readily appreciate the utility in following the particular cell-free translation machine's instructions. If a T7-histadine promoter or terminator fragment is added to a primary transcript, translation of the TAP fragment can result in histidine tagged polypeptides, which can be purified as discussed below. As discussed herein, any tag can be used.

The expressed Mtb polypeptides can be purified using any purification method for purifying expressed polypeptides. In one embodiment histidine tagged polypeptides can be purified with Qiagen nickel columns, such as Ni-NTA Superflow 96 Biorobot Kit. A person with skill in the art can readily appreciate the utility in following the instructions of the particular polypeptide purification system. Other methods that can be used to purify polypeptides include ultrafiltration, extraction, and chromatography.

The identity, quantity and purity of the purified Mtb polypeptides can be verified by SDS gel electrophoresis. According to one embodiment of the invention, MALDI-TOF MS (Matrix Assisted Laser Desorption/Ionization-Time of Flight Mass Spectrometry) can be employed to confirm the fidelity of the purified polypeptides. According to this embodiment, aliquots of each polypeptide (1-2 µg) can be aliquoted into about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more well plates and digested with modified trypsin. The resulting material can be mixed with matrix (alpha-cyano-4-hydroxycinnamic acid (CHCA)) and spotted onto any target plate with a suitable number of spots, for example, 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more spots. In one embodiment, a 384-spot "anchor chip" target plate (Bruker Daltonics, Billerica, Mass.) can be used. The plate can be transferred to the sample stage of a Bruker Autoflex MALDI-TOF mass spectrometer. The spectrometer can be set up to automatically scan the plate and search the Mascot polypeptide database via the Internet. Accordingly, a very rapid verification system can verify purity, identity, and quantity in less than a day, for example, depending on the amount of polypeptides. Purified *Mtb* polypeptides can be placed in libraries or organized into arrays for subsequent testing and analysis.

Humoral Immune Response

Use of the Mtb polypeptide libraries and arrays prepared, for example, according the methods above (e.g. using TAP or adapter technology) can be used to identify antigenic targets of humoral immunity in Mtb non-human animals and human patients. A humoral immune response relates to the generation of antibodies and their ability to bind to a particular antigen. In general, the humoral immune system uses white blood cells (B-cells), which have the ability to recognize antigens, to generate antibodies that are capable of binding to the antigens.

In one embodiment, the Mtb polypeptides of the invention are generated according to the methods described above. In certain aspects of this embodiment additional polynucleotide sequences that encode linker molecules are added to the TAP primary fragment or the TAP expression fragment such that the expressed Mtb polypeptides are fused to a linker molecule. As discussed previously, the term "linker molecule" encompasses molecules that are capable of immobilizing the polypeptides to a solid support.

In a particular embodiment, a Mtb polynucleotide of interest is fused to a HA epitope tag such that the expressed product can include the Mtb gene product fused to the HA epitope. In another embodiment, a Mtb polynucleotide of interest is combined with a histidine (His) coding sequence, such that the expressed product can include the Mtb gene product and a 6×, 7×, 8×, 9×, or 10× histidine tag. In other embodiments a Mtb polynucleotide is combined with a sequence that codes for a GST tag, fluorescent protein tag, or Flag tag. Using these methods it is possible to express and tag every Mtb polypeptide encoded by its genome. In another embodiment, the tagged Mtb polypeptide can be attached to a solid support, such as a 96-well plate. The immobilize polypeptides can be contacted with an antiserum or other fluid containing antibodies from an animal that has been immunized with one or more antigens from Mtb. In one embodiment, ELISA and Western blot assays are performed in parallel to detect the presence of immunogenic Mtb polypeptides.

As an example of an ELISA assay, tagged Mtb polypeptides can be immobilized on a solid support, such as a 96-well plate. The immobilized Mtb polypeptides are then incubated with serum from an animal that has been immunized with one or more antigens from Mtb, or has been infected directly with Mtb by inoculation, aerosol delivery, or the like. The reaction mixture can be washed to remove any unbound serum antibodies. The ability of the serum antibodies to bind to the bound Mtb polypeptides can then be detected using any one of a number of methods. For example, enzyme linked secondary antibodies can be added to detect the presence of an antigen specific antibody. Any enzyme linked secondary antibody can be used in this invention, depending on the source of the serum. For example, if vaccinated mouse serum is used to provide the primary antibody, enzyme linked anti-mouse antibody can be used as a secondary antibody. Likewise if human serum is used to provide the primary antibody, enzyme linked anti-human serum can be used as a secondary enzyme.

Any suitable assay can be used to determine the amount of bound polypeptide specific antibody. Also, skilled artisans can develop the enzyme assay to determine the amount of polypeptide specific antibody that is bound. In one embodiment, the readout from an assay can show the presence of different levels of antibody in each of the 96 wells. For example, while some Mtb polypeptides are not able to elicit any serum antibodies, other Mtb polypeptides can elicit intermediate levels of antibodies, and some can elicit high antibody levels. In one embodiment, polypeptides that generate high antibody titers can be further researched to determine which polypeptides are present on the surface of the virus. In a particular embodiment of the invention Mtb polypeptides that generate high antibody titers and that are located on the surface of the virus are candidates for use in the development of a subunit Mtb vaccine.

In addition, serodiagnostic tests may be developed using antigens identified and characterized by these methods. That is, the peptide (epitopes) identified herein find use in detecting antibodies in serum from Mtb infected or exposed organisms, animals or patients.

Figure 3:
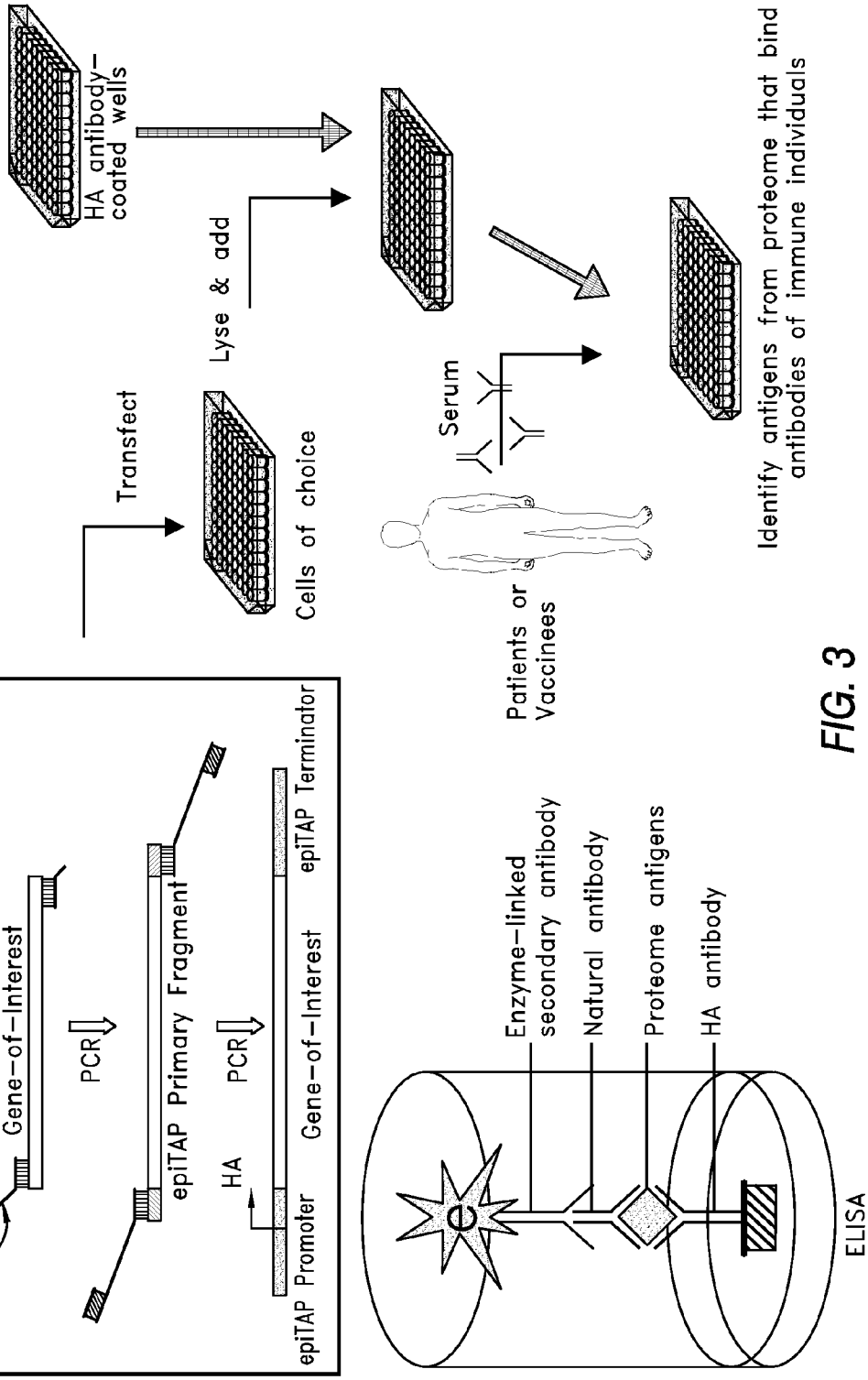
FIG. 3. demonstrates how a plurality of polypeptides from a target organism can be assayed to determine each polypeptide's ability to elicit a humoral immune response.

FIG. 3 demonstrates one embodiment of determining the humoral immune response generated by an array of polypeptides. One of skill in the art may deviate in certain details from those shown in FIG. 3. For example, the HA tag, or any other tag as described above, may be placed at either the C-terminal or N-terminal end of the polypeptide to insure that epitopes are not concealed due to binding to the plate. Instead of HA tagged polypeptides, a histidine tag can be used, and the polypeptides can be bound to nickel coated plates. For example a 6×, 7×, 8×, 9×, or 10× histidine tag can be used. Alternatively, histidine tagged polypeptides can be purified from either transfected cells or from the in vitro transcription translation system. Furthermore, purified Mtb polypeptides can be attached non-specifically to polypeptide-absorbing plates such as Immulon plates, for example.

In one aspect of the present invention, highly immunogenic Mtb antigens are detected by comparing the results of Western blotting analysis with ELISA. Western blotting and ELISA are two independent yet complementary methods that may be used to detect immunogenic Mtb in qualitative and quantitative ways. Western blotting is often used to examine the quality of a polypeptide or protein sample, including such parameters as purity, protein integrity, and degradation. Western blotting detects polypeptides in their denatured form. In one aspect of this embodiment, ELISA, which detects native polypeptides, is used to further examine Western-positive Mtb polypeptides in a more quantitative fashion, to illustrate the strength of the Mtb epitope's immunogenicity.

Cell-Mediated Immune Response

Use of the TAP-expressed Mtb polypeptide libraries and arrays prepared according the methods above (e.g. using TAP or adapter technology) can also be exploited to identify the highly immunogenic targets of cell-mediated immunity in Mtb vaccinated non-human animals. In contrast to a humoral immune response, where an antibody binds directly binding to an antigen, a cell-mediated immune response relates to T-cells binding to the surface of other cells that display the antigen. When certain T-cells come into contact with a presented antigen, they produce and release cytokines such as interferon-γ (IFN-γ) or Tumor Necrosis Factor-alpha (TNF-α). Cytokines are cellular signals that can alter the behavior or properties of another cell. For example, cytokines may inhibit viral replication, induce increased expression of MHC class I and peptide transporter molecules in infected cells, or activate macrophages. Accordingly, cytokines released by T-cells, associated with the binding to an antigen, can be used to identify and detect T-cell/antigen interactions.

Some cells have MHC molecules on their membranes to present antigens to T-cells. Efficient T-cell function relies on proper recognition of the MHC-antigen complex. There are two types of MHC molecules: Class I and Class II. The two different classes of MHC molecules bind peptides from different sources inside the cell for presentation at the cell surface to different classes of T-cells. Any T-cell can be used in the present invention, and include for example both $CD4^+$ and $CD8^+$ T-cells. $CD8^+$ cells (cytotoxic T-cells) bind epitopes that are part of class I MHC molecules. $CD4^+$ T-Cells, which includes inflammatory CD4 T-cells and helper CD4 T-cells, bind epitopes that are part of class II MHC molecules. Only specialized antigen-presenting cells express class II molecules.

There are three main types of antigen-presenting cells: B cells, macrophages and dendritic cells. Each of these cell types is specialized to process and present antigens from different sources to T-cells, and two of them, the macrophages and the B cells, are also the targets of subsequent actions of armed effector T-cells. These three cell types can express the specialized co-stimulatory molecules that enable them to activate naïve T-cells, although macrophages and B cells express those molecules only when suitably activated by infection.

Embodiments of the present invention relate to detecting Mtb polypeptides capable of evoking a cell-mediated immune response in order to identify potential candidates for use in a subunit vaccine or other pharmaceutical composition. According to one method of detecting a cell-mediated immune response, an Mtb polypeptide is delivered to an antigen-presenting cell where it can be presented in a manner that is recognized by antigen specific T-cells. In another embodiment of the invention, a transcriptionally active gene can be delivered to an antigen-presenting cell where expressed and presented in a manner that can be recognized by antigen specific T-cells. Mtb antigen specific T-cells can be acquired from numerous sources. For example, animals that have been infected, or immunized with one or more antigens from Mtb virus are a good source of antigen specific T-cells.

Alternatively, human Mtb patients and volunteers immunized with Mtb can be a source of antigen specific T-cells.

Figure 4:
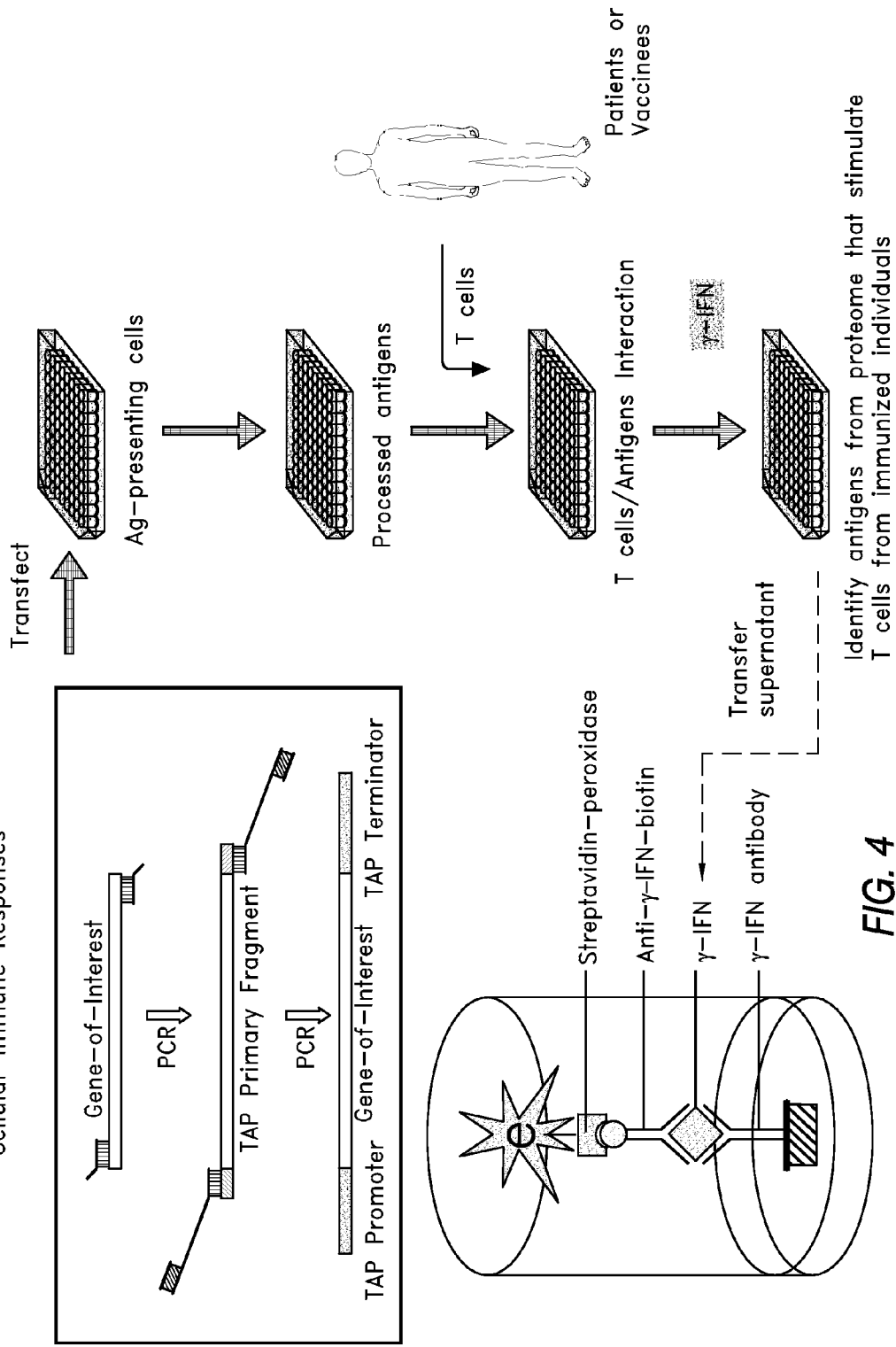
FIG. 4. demonstrates how a plurality of polypeptides from a target organism can be assayed to determine each polypeptide's ability to elicit a cell-mediated response.
Figure 5B:
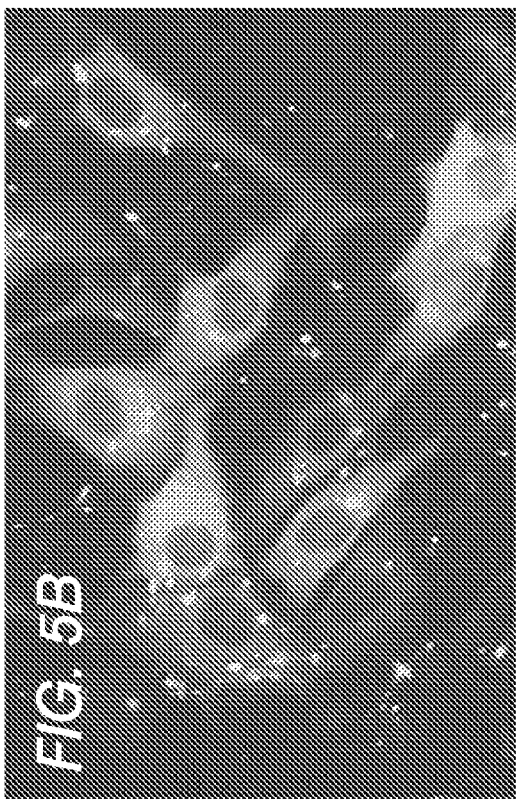
FIG. 5. demonstrates that fluorescent proteins (goat IgG antibody) can be more effectively delivered into either NIH-3T3 cells (A&B) and human dendritic cells (C&D) with a protein delivery reagent (B&D) as opposed to without a protein delivery reagent (A&C).
Figure 5D:
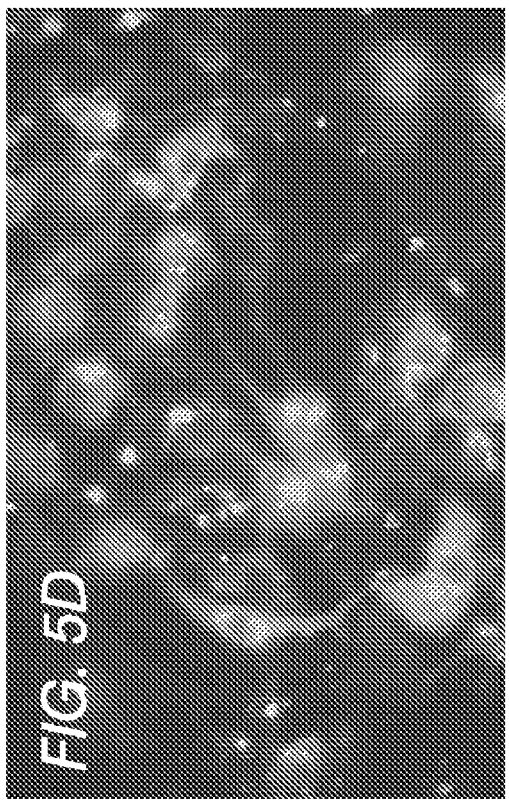
Figure 5A:
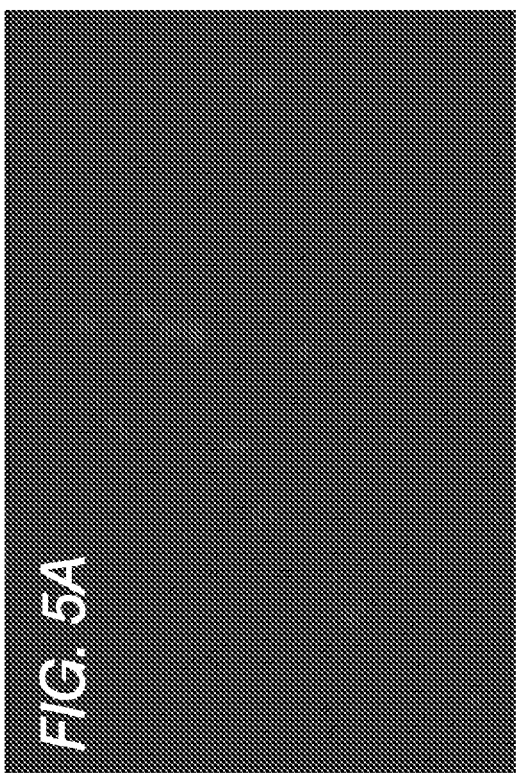
Figure 5C:
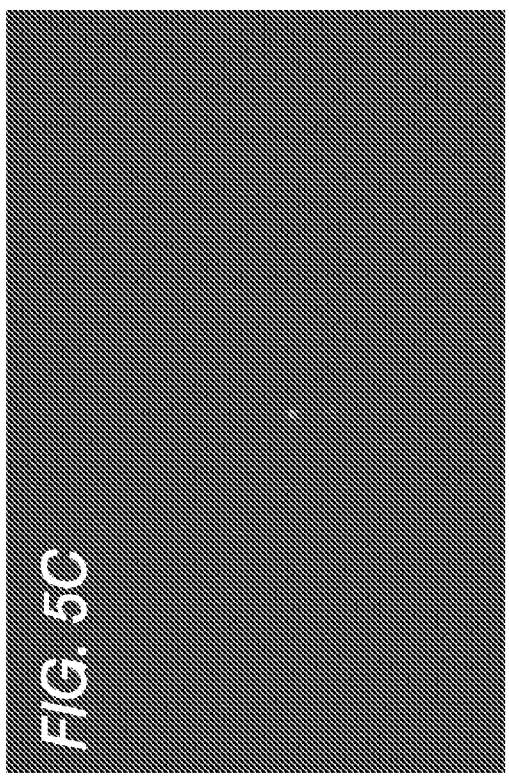

FIG. 4 demonstrates one embodiment of determining the cell-mediated immune response generated by an array of polypeptides. One of skill in the art may deviate in certain details from those shown in FIG. 4.

In order to test the ability of Mtb polypeptides to elicit a cell-mediated response, a plurality of Mtb polynucleotides can be amplified and made transcriptionally active using TAP technology. In one embodiment about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266 Mtb polynucleotides are made transcriptionally active using TAP technology.

In one embodiment, transcriptionally active Mtb polynucleotides can be transfected into an antigen-presenting cell and expressed within the cell. In another embodiment, instead of transfecting the genes into an antigen-presenting cell, the Mtb TAP fragments can be expressed in an in vivo or in vitro (cell-free) expression system and the expressed polypeptide can be delivered into the antigen-presenting cell. The polypeptide can be delivered into the antigen-presenting cell according to any method. In one embodiment, the polypeptide can be delivered using the technology described in U.S. patent application Ser. No. 09/738046, entitled "Intracellular Protein Delivery Reagent" and U.S. patent application Ser. No. 10/141535, entitled "Intracellular Protein Delivery Compositions and Methods of Use," both of which are hereby incorporated by reference in their entirety. The reagents described therein are capable of delivering any type of polypeptide into any type of cell. Furthermore, the results of FIG. 5 demonstrate that dendritic cells can present antigens to T-cells supplied from an immunized host after antigenic polypeptides were delivered to the dendritic cells with reagents from the above mentioned applications.

In certain embodiments of the invention, reagents used to deliver polypeptides into cultured cells can be a cationic lipid formulation. In one embodiment, these reagents can deliver fluorescently labeled antibodies, high and low molecular weight dextrans, phycoerythrin-BSA, caspase 3, caspase 8, granzyme B, and β-galactosidase into the cytoplasm of a variety of different adherent and suspension cells. Caspases delivered to cells with are functional, since they can be shown to send cells into apoptosis. In one embodiment, Mtb polypeptides are delivered into dendritic cells using these reagents.

Detecting a T-cell's ability to bind to an antigen-presenting cell, after the antigen-presenting cell has processed a particular polypeptide, is useful in determining whether the particular polypeptide evokes a cell-mediated immune response. Once a particular polypeptide is delivered into or expressed in the antigen-presenting cell, an assay can be performed to identify T-cell interaction with the MHC-antigen complex. In one embodiment, it can be determined if T-cells obtained from an animal that was immunized with Mtb can bind to a particular antigen presented by an antigen-presenting cell. For example, an ELIspot assay (Enzyme-Linked Immuno spotting; ELIspot) can be performed to identify antigen specific T-cells. Similar immunoassays can be performed to identify Mtb antigens (presented by an antigen-presenting cells) that stimulate T-cells from active Mtb patients or immunized individuals.

One method of detecting a T-cell/antigen interaction is to measure the amount of a particular cytokine released by the T-cell when it interacts with a MHC-antigen complex. The skilled artisan can appreciate that other cellular signals can be used to indicate a cell-mediated immune response. In one embodiment, the levels of IFN-γ released by T-cells can indicate whether a particular peptide is capable of evoking a cell-mediated immune response. In a particular embodiment, an antibody specific for IFN-γ can be coated onto a solid support. Unbound antibodies can be washed away and IFN-γ obtained from the supernatant containing T-cells plus antigen-presenting cells or antigen transduced antigen-presenting cells, can be added to the wells. A biotinylated secondary antibody specific for IFN-γ can be added. Excess secondary antibody can be removed and Streptavidin-Peroxidase can be added to the mixture. Streptavidin-Peroxidase is capable of binding to the biotinylated antibody to complete the four-member immunoassay "sandwich." Excess or unbound Streptavidin-Peroxidase is easily removed from the mixture. In order to detect amount of bound Streptavidin-Peroxidase, a substrate solution can be added which reacts with the Streptavidin-Peroxidase to produce color. The intensity of the colored product is directly proportional to the concentration of IFN-γ present in the T-cell/antigen-presenting cell supernatant. Kits for performing these types of immunoassay are readily available from many commercial suppliers or the necessary reagents composing such kits can be purchased separately or produced in-house. In one embodiment, processed and presented Mtb polypeptide that evokes T-cells to produce a high level of IFN-γ can be considered a strong candidate for use in developing a subunit vaccine.

Those with skill in the art will appreciate that other methods can be used to detect T-cell/Antigen interactions. These methods include bead based assays, flow-based assays, RT-PCR based assays, cytokine ELISAs, lymphoproliferation assays, cytotoxic T cell assays, or any other assay that can detect the interaction of a T-cell with a responder cell (e.g. macrophage).

Developing a Subunit Vaccine, Pharmaceutical Composition, or Immunogenic Composition A particular Mtb polypeptide that has been identified to elicit a humoral or cell-mediated immune response, can be further explored to determine its ability to be used in a subunit vaccine, pharmaceutical composition, or immunogenic composition. The terms "subunit vaccine," "DNA vaccine," "recombinant vaccine" and "immunogenic composition" encompass vaccines that are comprised of polypeptides, nucleic acids or a combination of both. Further exploration of a Mtb polypeptide vaccine candidate includes testing the Mtb polypeptide or nucleic acid encoding the Mtb polypeptide in a large number of animal subjects, volunteers or patients. In a particular embodiment, surface antigens can be studied closely because of the likelihood that they can inhibit virus infectivity. In one embodiment, every polypeptide encoded by the Mtb genome is assayed to determine its immunogenic effect. Polypeptides that elicit an immune response, whether cell-mediated or humoral, can be more closely studied to determine potential use alone or in conjunction with other polypeptides and genes as a subunit vaccine, pharmaceutical composition, or immunogenic composition. Suitable methodologies for electing and detecting an immune response are well established in the art.

Uses of Vaccine Compositions

As noted previously, the present invention provides peptide immunogens and nucleic acids encoding the immunogens. As such, the present invention also provides methods of using the immunogens to generate an immune response in a mammalian host.

Methods of generating immune responses in a host are known in the art. However, according to the present invention, the method includes administering to the host an immunogenic composition. The immunogenic composition includes at least one nucleic acid selected from SEQ ID NO: 46-64 and/or 110-121. In addition, fragments of these sequences can be used. Also, it should be noted that combinations of these sequences may be used to generate an immune response against Mtb. When using nucleic acids to generate an immune response the nucleic acids preferably encode peptides found in SEQ ID NO: 65-83 and/or 122-133. In addition, fragments of these sequences can be used. Also, combinations of these sequences can be used.

When combinations of the above immunogenic compositions are to be used at least 2, 3, 4 or 5 or more of the nucleic acids or fragments thereof can be combined to generate an immunogenic composition. Any combination of the nucleic acids finds use in this method.

Also, methods of generating an immune response include administering to the host at least one peptide selected from the peptides found in SEQ ID NO: 65-83 and/or 122-133. In addition, fragments of these sequences can be used. Also, it should be noted that combinations of these sequences may be used to generate an immune response against Mtb. When combinations of the above immunogenic compositions are to be used at least 2, 3, 4 or 5 or more of the nucleic acids or fragments thereof can be combined to generate an immunogenic composition. Any combination of screened nucleic acids finds use in this method.

Kits

Various nucleic acids and peptides have been identified that generate an immune response. As such, the nucleic acids and peptides find use in kits. The kits of the invention are useful for a variety of applications including combining reagents necessary for producing vaccine compositions. Such vaccine compositions include the polypeptides and polynucleotides described herein as well as carriers, diluents and other pharmaceutically acceptable carriers. It should be noted, as described above, that the kits may include fragments of the nucleic acids or peptides described herein as well as combinations of the nucleic acids and/or peptides described herein. Preferably the kits include at least 2, 3, 5, 10, 15, 20, 25, 30 or more nucleic acids or peptides described herein. Any combination of the nucleic acids or peptides can be used. In addition, the kits may include adjuvants. In addition, the kits may include instructions for preparing and administering the vaccines.

In addition, the kits of the invention find use as diagnostic kits. In particular, the kits find use as serodiagnostic kits. As such, the kits include at least one peptide as described herein. Preferably, however, the kits include a plurality of peptides, such as at least 2, 3, 5, 10, 15 or 20 or more peptides for diagnosis of Mtb infection or exposure of an organism, animal or patient.

In some embodiments, the nucleic acids encoding the polypeptides find use in diagnostic kits. The nucleic acids encoding the antigenic peptides find use as probes to detect complementary nucleic acids of Mtb. However, in an alternative embodiment the kits include the polypeptides produced from the in vitro transcription-translation reaction find use in detecting antibodies from an organism, animal or patient exposed to Mtb.

EXAMPLES

Example 1

Procedure for Generating Histidine Tagged TAP Express Fragments

A detailed procedure that is used to produce tagged T7-TAP Express fragments is as follows: 96 different genes were amplified from a mixture of plasmid templates. A first PCR reaction was run with customized 5' and 3' primers. The 5' primers contained between 43-48 bases. In particular, the T-7-His TAP ends contained 28 bases while the gene-specific component contained between 15-20 bases. The 3' primers contained between 45-50 bases. Specifically, the T7-terminator TAP ends contained 30 bases while the gene specific component contained between 15-20 bases. The reaction temperature and times for the first PCR reaction were: 94° C. for 2 minutes, followed by 28 cycles of: 94° C. for 20 seconds, 58° C. for 35 seconds, and 70° C. for 2 minutes (for genes that contained more than 2 kb, 1 minute was added for each kb).

After the first PCR reaction was performed, an aliquot of each PCR reaction from the previous step was transferred into a PCR reaction containing the T7-histidine promoter fragment and T7 terminator fragment. The T7 promoter primer contained 25 bases, while the T7-promoter-His tag fragment contained a 104 base EcoRV/BglII fragment. The T7-terminator fragment was a 74 base oligonucleotide. The reaction temperature and times for the second PCR reaction were: 94° C. for 2 minutes, followed by 30 cycles of: 94° C. for 20 seconds, 60° C. for 35 seconds, and 70° C. for 2 minutes (for genes that contained more than 2 kb, 1 minute was added for each kb).

Example 2

Using the Mtb Proteome to Identify the Antigenic Targets of Humoral Immunity in Mtb Mice and Humans The following is a method used to systematically screen and identify antigens in Mtb that give rise to a protective humoral immune response. A bioinformatics approach was used to order the *M. tuberculosis* polynucleotide sequences for amplification. The Mtb genome was first analyzed for hydrophobicity by the method of Doolittle. Hydrophilic polynucleotides sequences were then further grouped by size. Hydrophilic open reading frames/coding regions longer than 500 bp were selected for TAP amplification. Initially, three hundred Mtb genes were synthesized by TAP and ~100 proteins were translated and purified in arrays; as described below.

TAP PCR

The PCR reactions were performed such that a nucleotide sequence encoding a 6×His tag was fused to these amplified transcriptionally active genes. The resulting His tagged TAP fragments were expressed to produce ~100 Mtb polypeptides containing the His tag.

A detailed procedure that was used to produce tagged T7-TAP Express fragments is as follows: groups of 96 Mtb polynucleotide sequences were amplified from Mtb genomic DNA. A first PCR reaction was performed using customized 5' and 3' primers, as shown in Table 1 (SEQ ID NOS: 8 and 9; 10 and 11; 12 and 13; 14 and 15; 16 and 17; 18 and 19; 20 and 21; 22 and 23; 24 and 25; 26 and 27; 28 and 29; 30 and 31; 32 and 33; 34 and 35; 36 and 37; 38 and 39; 40 and 41; 42 and 43; 44 and 45; 86 and 87; 88 and 89; 90 and 91; 92 and 93; 94 and 95; 96 and 97; 98 and 99; 100 and 101; 102 and 103; 104 and 105; 106 and 107; 108 and 109). The 5' primers contained between 43-48 bases. In particular, the T-7-His TAP ends contained 28 bases while the gene-specific component contained between 15-20 bases. The 3' primers contained between 45-50 bases. Specifically, the T7-terminator TAP ends contained 30 bases while the gene specific component contained between 15-20 bases.

TABLE 1

Immunogenic Mtb Polypeptides: Primers, Polynucleotide Sequences, and Amino Acid Sequences All polynucleotide sequences are shown in the 5' to 3' orientation Rv2031c HEAT SHOCK PROTEIN HSPX (ALPHA-CRSTALLIN HOMOLOG)
14 kDa ANTIGEN) (HSP16.3)
5' primer:
GAAGGAGATATACCATGCATCATCATCATCATCATATGGCCACCACCCTT (SEQ ID NO:8)

3' primer:
TGATGATGAGAACCCCCCCCGTTGGTGGACCGGATCTGAA (SEQ ID NO:9)

Polynucleotide sequence:
ATGGCCACCACCCTTCCCGTTCAGCGCCACCCGCGGTCCCTCTTCCCCGAGTTTTCTGAGCT
GTTCGCGGCCTTCCCCGTCATTCGCCGGACTCCGGCCCACCTTCGACACCCGGTTGATGCGGC
TGGAAGACGAGATGAAAGAGGGGCGCTACGAGGTACGCGCGGAGCTTCCCGGGGTCGACCCC
GACAAGGACGTCGACATTATGGTCCGCGATGGTCAGCTGACCATCAAGGCCGAGCGCACCGA
GCAGAAGGACTTCGACGGTCGCTCGGAATTCGCGTACGGTTCCTTCGTTCGCACGGTGTCGC
TGCCGGTAGGTGCTGACGAGGACGACATTAAGGCCACCTACGACAAGGGCATTCTTACTGTG
TCGGTGGCGGTTTCGGAAGGGAAGCCAACCGAAAAGCACATTCAGATCCGGTCCACCAAC
435 bp (SEQ ID NO:46)

Amino acid sequence:
MATTLPVQRHPRSLFPEFSELFAAFPSFAGLRPTFDTRLMRLEDEMKEGRYEVRAELPGVDP
DKDVDIMVRDGQLTIKAERTEQKDFDGRSEFAYGSFVRTVSLPVGADEDDIKATYDKGILTV
SVAVSEGKPTEKHIQIRSTN(SEQ ID NO:65)

RV3763

19 KDA LIPOPROTEIN ANTIGEN PRECURSOR LPQH
5' primer:
GAAGGAGATATACCATGCATCATCATCATCATCATGTGAAGCGTGGACTG(SEQ ID NO:10)

3' primer:
TGATGATGAGAACCCCCCCCGGAACAGGTCACCTCGATTT (SEQ ID NO:11)

Polynucleotide sequence:
GTGAAGCGTGGACTGACGGTCGCGGTAGCCGGAGCCGCCATTCTGGTCGCAGGTCTTTCCGG
ATGTTCAAGCAACAAGTCGACTACAGGAAGCGGTGAGACCACGACCGCGGCAGGCACGACGG
CAAGCCCCGGCGCCGCCTCCGGGCCGAAGGTCGTCATCGACGGTAAGGACCAGAACGTCACC
GGCTCCGTGGTGTGCACAACCGCGGCCGGCAATGTCAACATCGCGATCGGCGGGCGGCGAC
CGGCATTGCCGCCGTGCTCACCGACGGCAACCCTCCGGAGGTGAAGTCCGTTGGGCTCGGTA
ACGTCAACGGCGTCACGCTGGGATACACGTCGGGCACCGGACAGGGTAACGCCTCGGCAACC
AAGGACGGCAGCCACTACAAGATCACTGGGACCGCTACCGGGGTCGACATGGCCAACCCGAT
GTCACCGGTGAACAAGTCGTTCGAAATCGAGGTGACCTGTTCC 480 bp (SEQ ID NO:47)

Amino acid sequence:
VKRGLTVAVAGAAILVAGLSGCSSNKSTTGSGETTTAAGTTASPGAASGPKVVIDGKDQNVT
GSVVCTTAAGNVNIAIGGAATGIAAVLTDGNPPEVKSVGLGNVNGVTLGYTSGTGQGNASAT
KDGSHYKITGTATGVDMANPMSPVNKSFEIEVTCS (SEQ ID NO:66)

TABLE 1-continued

Immunogenic Mtb Polypeptides: Primers, Polynucleotide
Sequences, and Amino Acid Sequences Rv2744c CONSERVED 35 KDA ALANINE RICH PROTEIN
5' primer:
GAAGGAGATATACCATGCATCATCATCATCATCATATGGCCAATCCGTTC (SEQ ID
NO:12)

3' primer:
TGATGATGAGAACCCCCCCCCTGACCGTAGGGCTGCTCGG (SEQ ID NO:13)

Polynucleotide sequence:
ATGGCCAATCCGTTCGTTAAAGCCTGGAAGTACCTCATGGCGCTGTTCAGCTCGAAGATCGA
CGAGCATGCCGACCCCAAGGTGCAGATTCAACAGGCCATTGAGGAAGCACAGCGCACCCACC
AAGCGCTGACTCAACAGGCGGCGCAAGTGATCGGTAACCAGCGTCAATTGGAGATGCGACTC
AACCGACAGCTGGCGGACATCGAAAAGCTTCAGGTCAATGTGCGCCAAGCCCTGACGCTGGC
CGACCAGGCCACCGCCGCCGGAGACGCTGCCAAGGCCACCGAATACAACAACGCCGCCGAGG
CGTTCGCAGCCCAGCTGGTGACCGCCGAGCAGAGCGTCGAAGACCTCAAGACGCTGCATGAC
CAGGCGCTTAGCGCCGCAGCTCAGGCCAAGAAGGCCGTCGAACGAAATGCGATGGTGCTGCA
GCAGAAGATCGCCGAGCGAACCAAGCTGCTCAGCCAGCTCGACGCAGGCGAAGATGCAGGAGC
AGGTCAGCGCATCGTTGCGGTCGATGAGTGAGCTCGCCGCGCCAGGCAACACGCCGAGCCTC
GACGAGGTGCGCGACAAGATCGAGCGTCGCTACGCCAACGCGATCGGTTCGGCTGAACTTGC
CGAGAGTTCGGTGCAGGGCCGGATGCTCGAGGTGGAGCAGGCCGGGATCCAGATGGCCGGTC
ATTCACGGTTGGAACAGATCCGCGCATCGATGCGCGGTGAAGCGTTGCCGGCCGGCGGGACC
ACGGCTACCCCCAGACCGGCCACCGAGACTTCTGGCGGGGCTATTGCCGAGCAGCCCTACGG
TCAG 813 bp (SEQ ID NO:48)

Amino acid sequence:
MANPFVKAWKYLMALFSSKIDEHADPKVQIQQAIEEAQRTHQALTQQAAQVIGNQRQLEMRL
NRQLADIEKLQVNVRQALTLADQATAAGDAAKATEYNNAAEAFAAQLVTAEQSVEDLKTLHD
QALSAAAQAKKAVERNAMVLQQKIAERTKLLSQLEQAKMQEQVSASLRSMSELAAPGNTPSL
DEVRDKIERRYANAIGSAELAESSVQGRMLEVEQAGIQMAGHSRLEQIRASMRGEALPAGGT
TATPRPATETSGGAIAEQPYGQ (SEQ ID NO:67)

Rv0097

POSSIBLE OXIDOREDUCTASE
5' primer:
GAAGGAGATATACCATGCATCATCATCATCATCATATGACGCTTAAGGTC (SEQ ID
NO:14)

3' primer:
TGATGATGAGAACCCCCCCCTGCCGCGTATCCCGGCGTCT (SEQ ID NO:15)

Polynucleotide sequence:
ATGACGCTTAAGGTCAAAGGCGAGGGACTCGGTGCGCAGGTCACAGGGGTCGATCCCAAGAA
TCTGGACGATATAACCACCGACGAGATCCGGGATATCGTTTACACGAACAAGCTCGTTGTGC
TAAAAGACGTCCATCCGTCTCCGCGGGAGTTCATCAAACTCGGCAGGATAATTGGACAAATC
GTTCCGTATTACGAACCCATGTACCATCACGAAGACCACCCGGAGATCTTTGTCTCCTCCAC
TGAGGAAGGTCAGGGGGTCCCAAAAACCGGCGCGTTCTGGCATATCGACTATATGTTTATGC
CGGAACCTTTCGCGTTTTCCATGGTGCTGCCGCTGGCGGTGCCTGGACACGACCGGCACGGT
TATTTCATCGATCTCGCCAGGGTCTGGCAGTCGCTGCCCGCCGCCAAGCGAGACCCGGCCCG
CGGAACCGTCAGCACCCACGACCCTCGACGCCACATCAAGATCCGACCCAGCGACGTCTACC
GGCCCATCGGAGAGGTATGGGACGAGATCAACCGGACCACGCCCCCAATAAAGTGGCCTACG
GTCATCCGGCACCCAAAGACCGGCCAAGAGATCCTCTACATCTGCGCGACGGGCACCACCAA
GATCGAGGACAAGGACGGCAATCCGGTTGATCCGGAGGTGCTGCAAGAACTCATGGCCGCGA
CCGGACAGCTCGATCCTGAGTACCAGTCGCCGTTCATACATACTCAGCACTACCAGGTTGGC
GACATCATCTTGTGGGACAACCGGGTTCTCATGCACCGAGCGAAGCACGGCAGCGCCGCGGG
CACTCTGACGACCTACCGCCTGACCATGCTTGATGGCCTCAAGACGCCGGGATACGCGGCA
870 (SEQ ID NO:49)

Amino acid sequence:
MTLKVKGEGLGAQVTGVDPKNLDDITTDEIRDIVYTNKLVVLKDVHPSPREFIKLGRIIGQI
VPYYEPMYHHEDHPEIFVSSTEEGQGVPKTGAFWHIDYMFMPEPFAFSMVLPLAVPGHDRGT
YFIDLARVWQSLPAAKRDPARGTVSTHDPRRHIKIRPSDVYRPIGEVWDEINRTTPPIKWPT
VIRHPKTGQEILYICATGTTKIEDKDGNPVDPEVLQELMAATGQLDPEYQSPFIHTQHYQVG
DIILWDNRVLMHRAKHGSAAGTLTTYRLTMLDGLKTPGYAA (SEQ ID NO:68)

Rv0475

IRON-REGULATED HEPARIN BINDING HEMAGGLUTININ HBHA (ADHESIN)
5' primer:

TABLE 1-continued

Immunogenic Mtb Polypeptides: Primers, Polynucleotide
Sequences, and Amino Acid Sequences

GAAGGAGATATACCATGCATCATCATCATCATCATATGGCTGAAAACTCG (SEQ ID
NO:16)

3' primer:
TGATGATGAGAACCCCCCCCCTTCTGGGTGACCTTCTTGG(SEQ ID NO:17)

Polynucleotide sequence:
ATGGCTGAAAACTCGAACATTGATGACATCAAGGCTCCGTTGCTTGCCGCGCTTGGAGCGGC
CGACCTGGCCTTGGCCACTGTCAACGAGTTGATCACGAACCTGCGTGAGCGTGCGGAGGAGA
CTCGTACGGACACCCGCAGCCGGGTCGAGGAGAGCCGTGCTCGCCTGACCAAGCTGCAGGAA
GATCTGCCCGAGCAGCTCACCGAGCTGCGTGAGAAGTTCACCGCCGAGGAGCTGCGTAAGGC
CGCCGAGGGCTACCTCGAGGCCGCGACTAGCCGGTACAACGAGCTGGTCGAGCGCGGTGAGG
CCGCTCTAGAGCGGCTGCGCAGCCAGCAGAGCTTCGAGGAAGTGTCGGCGCGCCGAAGGC
TACGTGGACCAGGCGGTGGAGTTGACCCAGGAGGCGTTGGGTACGGTCGCATCGCAGACCCG
CGCGGTCGGTGAGCGTGCCGCCAAGCTGGTCGGCATCGAGCTGCCTAAGAAGGCTGCTCCGG
CCAAGAAGGCCGCTCCGGCCAAGAAGGCCGCTCCGGCCAAGAAGGCGGCGGCCAAGAAGGCG
CCCGCGAAGAAGGCGGCGGCCAAGAAGGTCACCCAGAAG 600 bp (SEQ ID NO:50)

Amino acid sequence:
MAENSNIDDIKAPLLAALGAADLALATVNELITNLRERAEETRTDTRSRVEESRARLTKLQE
DLPEQLTELREKFTAEELRKAAEGYLEAATSRYNELVERGEAALERLRSQQSFEEVSARAEG
YVDQAVELTQEALGTVASQTRAVGERAAKLVGIELPKKAAPAKKAAPAKKAAPAKKAAAKKA
PAKKAAAKKVTQK(SEQ ID NO:69)

Rv3117

PROBABLE THIOSULFATE SULFURTRANSFERASE CYSA3 (RHODANESE-LIKE
PROTEIN) (THIOSULFATE CYANIDE TRANSSULFURASE) (THIOSULFATE
THIOTRANSFERASE)
5' primer:
GAAGGAGATATACCATGCATCATCATCATCATCATATGGCACGCTGCGAT (SEQ ID
NO:18)

3' primer:
TGATGATGAGAACCCCCCCCCGCTTCCCAACTCGATCGGGG (SEQ ID NO:19)

Polynucleotide sequence:
ATGGCACGCTGCGATGTCCTGGTCTCCGCCGACTGGGCTGAGAGCAATCTGCACGCGCCGAA
GGTCGTTTTCGTCGAAGTGGACGAGGACACCAGTGCATATGACCGTGACCATATTGCCGGCG
CGATCAAGTTGGACTGGCGCACCGACCTGCAGGATCCGGTCAAACGTGACTTCGTCGACGCC
CAGCAATTCTCCAAGCTGCTGTCCGAGCGTGGCATCGCCAACGAGGACACGGTGATCCTGTA
CGGCGGCAACAACAATTGGTTCGCCGCCTACGCGTACTGGTATTTCAAGCTCTACGGCCATG
AGAAGGTCAAGTTGCTCGACGGCGGCCGCAAGAAGTGGGAGCTCGACGGACGCCCGCTGTCC
AGCGACCCGGTCAGCCGGCCGGTGACCTCCTACACCGCCTCCCCGCCGGATAACACGATTCG
GGCATTCCGCGACGAGGTCCTGGCGGCCATCAACGTCAAGAACCTCATCGACGTGCGCTCTC
CCGACGAGTTCTCCGGCAAGATCCTGGCCCCCGCGCACCTGCCGCAGGAACAAAGCCAGCGG
CCCGGACACATTCCTGGTGCCATCAACGTGCCGTGGAGCAGGGCCGCCAACGAGGACGGCAC
CTTCAAGTCCGATGAGGAGTTGGCCAAGCTTTACGCCGACGCCGGCCTAGACAACAGCAAGG
AAACGATTGCCTACTGCCGAATCGGGGAACGGTCCTCGCACACCTGGTTCGTGTTGCGGGAA
TTACTCGGACACCAAAACGTCAAGAACTACGACGGCAGTTGGACAGAATACGGCTCCCTGGT
GGGCGCCCCGATCGAGTTGGGAAGC 834 bp (SEQ ID NO:51)

Amino acid sequence:
MARCDVLVSADWAESNLHAPKVVFVEVDEDTSAYDRDHIAGAIKLDWRTDLQDPVKRDFVDA
QQFSKLLSERGIANEDTVILYGGNNNWFAAYAYWYFKLYGHEKVKLLDGGRKKWELDGRPLS
SDPVSRPVTSYTASPPDNTIRAFRDEVLAAINVKNLIDVRSPDEFSGKILAPAHLPQEQSQR
PGHIPGAINVPWSRAANEDGTFKSDEELAKLYADAGLDNSKETIAYCRIGERSSHTWFVLRE
LLGHQNVKNYDGSWTEYGSLVGAPIELGS (SEQ ID NO:70)

Rv1347c

CONSERVED HYPOTHETICAL PROTEIN
5' primer:
GAAGGAGATATACCATGCATCATCATCATCATCATATGACCAAACCCACA (SEQ ID
NO:20)

3' primer:
TGATGATGAGAACCCCCCCCCGCAGCCGTGGTCGGAGCTT (SEQ ID NO:21)

Polynucleotide sequence:
ATGACCAAACCCACATCCGCTGGCCAGGCCGACGACGCGCTGGTTCGGCTAGCCCGCGAGCG
ATTCGACCTACCTGACCAGGTACGACGCCTCGCCCGCCCGCCCGTTCCATCGTTGGAGCCGC
CATACGGGTTGCGGGTCGCACAGCTGACCGACGCGGAGATGTTGGCGGAGTGGATGAACCGT
CCTCATCTGGCGGCGGCCTGGGAGTACGACTGGCCGGCGTCACGTTGGCGTCAACACCTGAA
CGCCCAACTTGAGGGAACCTATTCGTTGCCATTGATCGGCAGCTGGCACGGAACAGATGGTG
GTTATCTCGAATTATACTGGGCAGCAAAGGATTTGATTTCTCACTACTACGACGCAGACCCC TABLE 1-continued Immunogenic Mtb Polypeptides: Primers, Polynucleotide
Sequences, and Amino Acid Sequences TACGATTTGGGGCTGCACGCGGCCATCGCGGACTTGTCGAAGGTCAATCGGGGCTTCGGCCC
GCTGCTGCTACCGCGGATCGTGGCCAGCGTCTTTGCCAACGAGCCGCGTTGCCGGCGGATCA
TGTTCGACCCCGATCACCGCAACACCGCGACCCGTCGGTTGTGTGAGTGGGCCGGATGCAAG
TTCCTCGGTGAGCATGACACGACAAACCGGCGCATGGCGCTCTACGCTTTGGAAGCTCCGAC
CACGGCTGCG 633 bp (SEQ ID NO:52)

Amino acid sequence:
MTKPTSAGQADDALVRLARERFDLPDQVRRLARPPVPSLEPPYGLRVAQLTDAEMLAEWMNR
PHLAAAWEYDWPASRWRQHLNAQLEGTYSLPLIGSWHGTDGGYLELYWAAKDLISHYYDADP
YDLGLHAAIADLSKVNRGFGPLLLPRIVASVFANEPRCRRIMFDPDHRNTATRRLCEWAGCK
FLGEHDTTNRRMALYALEAPTTAA (SEQ ID NO:71)

Rv0815c

PROBABLE THIOSULFATE SULFURTRANSFERASE CYSA2 (RHODANESE-LIKE
PROTEIN) (THIOSULFATE CYANIDE TRANSSULFURASE) (THIOSULFATE
THIOTRANSFERASE)
5' primer:
GAAGGAGATATACCATGCATCATCATCATCATCATATGGCACGCTGCGAT (SEQ ID
NO:22)

3' primer:TGATGATGAGAACCCCCCCCGCTTCCCAACTCGATCGGGG(SEQ
ID NO:23)

Polynucleotide sequence:
ATGGCACGCTGCGATGTCCTGGTCTCCGCCGACTGGGCTGAGAGCAATCTGCACGCGCCGAA
GGTCGTTTTCGTCGAAGTGGACGAGGACACCAGTGCATATGACCGTGACCATATTGCCGGCG
CGATCAAGTTGGACTGGCGCACCGACCTGCAGGATCCGGTCAAACGTGACTTCGTCGACGCC
CAGCAATTCTCCAAGCTGCTGTCCGAGCGTGGCATCGCCAACGAGGACACGGTGATCCTGTA
CGGCGGCAACAACAATTGGTTCGCCGCCTACGCGTACTGGTATTTCAAGCTCTACGGCCATG
AGAAGGTCAAGTTGCTCGACGGCGGCCGCAAGAAGTGGGAGCTCGACGGACGCCCGCTGTCC
AGCGACCCGGTCAGCCGGCCGGTGACCTCCTACACCGCCTCCCCGCCGGATAACACGATTCG
GGCATTCCGCGACGAGGTCCTGGCGGCCATCAACGTCAAGAACCTCATCGACGTGCGCTCTC
CCGACGAGTTCTCCGGCAAGATCCTGGCCCCCGCGCACCTGCCGCAGGAACAAAGCCAGCGG
CCCGGACACATTCCTGGTGCCATCAACGTGCCGTGGAGCAGGGCCGCAACGAGGACGGCAC
CTTCAAGTCCGATGAGGAGTTGGCCAAGCTTTACGCCGACGCCGGCCTAGACAACAGCAAGG
AAACGATTGCCTACTGCCGAATCGGGGAACGGTCCTCGCACACCTGGTTCGTGTTGCGGGAA
TTACTCGGACACCAAAACGTCAAGAACTACGACGGCAGTTGGACAGAATACGGCTCCCTGGT
GGGCGCCCCGATCGAGTTGGGAAGC 834 bp (SEQ ID NO:53)

Amino acid sequence:
MARCDVLVSADWAESNLHAPKVVFVEVDEDTSAYDRDHIAGAIKLDWRTDLQDPVKRDFVDA
QQFSKLLSERGIANEDTVILYGGNNNWFAAYAYWYFKLYGHEKVKLLDGGRKKWELDGRPLS
SDPVSRPVTSYTASPPDNTIRAFRDEVLAAINVKNLIDVRSPDEFSGKILAPAHLPQEQSQR
PGHIPGAINVPWSRAANEDGTFKSDEELAKLYADAGLDNSKETIAYCRIGERSSHTWFVLRE
LLGHQNVKNYDGSWTEYGSLVGAPIELGS (SEQ ID NO:72)

Rv2613c

CONSERVED HYPOTHETICAL PROTEIN
5' primer:
GAAGGAGATATACCATGCATCATCATCATCATCATGTGAGTGACGAGGAC (SEQ ID
NO:24)

3' primer: TGATGATGAGAACCCCCCCCTGGTTGCCGAGCCCACTCGG (SEQ
ID NO:25)

Polynucleotide sequence:
GTGAGTGACGAGGACCGCACGGATCGGGCCACCGAGGACCACACCATCTTCGATCGGGGTGT
CGGCCAGCGCGACCAGCTGCAGCGGTTATGGACCCCCTACCGGATGAACTACCTGGCCGAAG
CGCCAGTGAAGCGTGACCCCAATTCCTCGGCCAGCCCTGCCGCAGCCGTTCACCGAGATCCCG
CAGCTGTCCGACGAAGAGGGTCTGGTGGTCGCTCGTGGCAAGCTGGTCTACGCCGTGCTCAA
CCTGTACCCGTACAACCCCGGGCACTTGATGGTGGTGCCCTATCGTCGGGTATCCGAACTCG
AGGATCTCACCGATTTGGAGAGCGCCGAGTTGATGGCGTTCACCCAGAAGGCGATTCGCGTG
ATCAAGAACGTGTCGCGTCCGCACGGCTTCAATGTCGGCCTGAACCTAGGGACATCGGCGGG
CGGGTCGCTGGCCGAGCACCTGCACGTGCATGTGGTGCCACGGTGGGGTGGCGATGCGAATT
TCATCACCATCATCGGGGGCTCCAAGGTGATTCCGCAGCTGCTGCGCGACACCCGTCGGCTG
CTTGCCACCGAGTGGGCTCGGCAACCA 588 bp (SEQ ID NO:54)

Amino acid sequence:
VSDEDRTDRATEDHTIFDRGVGQRDQLQRLWTPYRMNYLAEAPVKRDPNSSASPAQPFTEIP
QLSDEEGLVVARGKLVYAVLNLYPYNPGHLMVVPYRRVSELEDLTDLESAELMAFTQKAIRV TABLE 1-continued Immunogenic Mtb Polypeptides: Primers, Polynucleotide
Sequences, and Amino Acid Sequences IKNVSRPHGFNVGLNLGTSAGGSLAEHLHVHVVPRWGGDANFITIIGGSKVIPQLLRDTRRL
LATEWARQP(SEQ ID NO:73)

Rv3226c

CONSERVED HYPOTHETICAL PROTEIN
5' primer:
GAAGGAGATATACCATGCATCATCATCATCATCATATGTGCGGACGGTTT (SEQ ID
NO:26)

3' primer:
TGATGATGAGAACCCCCCCCCAGCAGCTGGATCTGCTCGG (SEQ ID NO:27)

Polynucleotide sequence:
ATGTGCGGACGGTTTGCGGTCACCACTGATCCGGCCCAGCTGGCCGAGAAAATCACGGCCAT
AGACGAGGCCACCGGGTGCGGTGGCGGGAAGACGAGCTACAACGTGGCACCCACCGACACGA
TCGCGACAGTGGTGTCCCGCCACAGCGAGCCCGACGACGAGCCCACCCGCCGGGTGCGGCTC
ATGCGCTGGGGACTGATTCCGTCGTGGATCAAGGCCGGGCCCGGCGGCGCACCCGATGCCAA
AGGCCCACCGCTGATCAACGCCCGCGCCGATAAGGTCGCCACGTCGCCGGCGTTCCGGAGTG
CGGTCAGAAGTAAGCGTTGCCTGGTGCCGATGGACGGCTGGTACGAATGGCGCGTCGACCCC
GACGCCACCCCGGGGAGGCCGAACGCCAAGACGCCGTTCTTCCTGCACCGCCACGACGGCGC
CCTGTTGTTCACGGCCGGGCTGTGGTCGGTTTGGAAGTCTTACAGGTCCGCCCCACCGCTGC
TGAGCTGCACGGTGATCACCACCGATGCCGTGGGCGAGCTGGCCGAGATCCATGACCGGATG
CCGCTGCTGCTGGCCGAAGAGGACTGGGACGACTGGCTGAATCCAGACGCCCCGCCGGATCC
TGAGCTGCTGGCCCGCCCGCCGGATGTGCGCGACATCGCGCTGCGCCAAGTGTCCACGTTGG
TCAACAACGTGCGCAACAACGGGCCTGAGCTGTTGGAGCCGGCCAGGTCGCAGCCCGAGCAG
ATCCAGCTGCTG 759 bp (SEQ ID NO:55)

Amino acid sequence:
MCGRFAVTTDPAQLAEKITAIDEATGCGGGKTSYNVAPTDTIATVVSRHSEPDDEPTRRVRL
MRWGLIPSWIKAGPGGAPDAKGPPLINARADKVATSPAFRSAVRSKRCLVPMDGWYEWRVDP
DATPGRPNAKTPFFLHRHDGALLFTAGLWSVWKSYRSAPPLLSCTVITTDAVGELAEIHDRM
PLLLAEEDWDDWLNPDAPPDPELLARPPDVRDIALRQVSTLVNNVRNNGPELLEPARSQPEQ
IQLL(SEQ ID NO:74)

Rv0349

HYPOTHETICAL PROTEIN
5' primer:
GAAGGAGATATACCATGCATCATCATCATCATCATGTGCCAGAGCTGGAG (SEQ ID
NO:28)

3' primer:
TGATGATGAGAACCCCCCCCGTCCGCCAGCTTGACCGACT (SEQ ID NO:29)

Polynucleotide sequence:
GTGCCAGAGCTGGAGACGCCCGACGACCCAGAGTCGATATACCTTGCCCGCCTCGAGGATGT
CGGAGAACACAGACCGACGTTCACGGGCGACATCTACCGACTCGGCGATGGTCGCATGGTGA
TGATCCTCCAGCACCCATGCGCGCTGCGGCACGGCGTTGACCTCCATCCGCGACTGCTGGTC
GCTCCCGTAAGACCCGACTCGCTTCGTTCCAACTGGGCTAGAGCCCCGTTCGGCACGATGCC
GCTTCCGAAGCTCATCGACGGTCAGGATCACTCGGCGGACTTCATCAATCTTGAACTCATCG
ATTCACCAACGCTTCCGACCTGTGAGCGGATCGCGGTGCTCAGCCAGTCAGGCGTCAACTTG
GTCATGCAACGGTGGGTGTACCACAGCACCCGGCTCGCCGTGCCCACGCACACCTACTCCGA
CAGCACCGTTGGCCCGTTCGATGAGGCAGACCTGATCGAGGAGTGGGTGACGGATCGCGTCG
ACGATGGGGCCGACCCGCAGGCGGCCGAACACGAATGCGCCTCCTGGCTCGATGAAAGAATC
AGCGGCCGCACTCGGCGAGCGCTGCTCAGCGACCGTCAGCACGCCAGTTCAATACGGCGAGA
AGCGCGTTCTCATCGAAAGTCGGTCAAGCTGGCGGAC 660 bp (SEQ ID NO:56)

Amino acid sequence:
VPELETPDDPESIYLARLEDVGEHRPTFTGDIYRLGDGRMVMILQHPCALRHGVDLHPRLLV
APVRPDSLRSNWARAPFGTMPLPKLIDGQDHSADFINLELIDSPTLPTCERIAVLSQSGVNL
VMQRWVYHSTRLAVPTHTYSDSTVGPFDEADLIEEWVTDRVDDGADPQAAEHECASWLDERI
SGRTRRALLSDRQHASSIRREARSHRKSVKLAD (SEQ ID NO:75)

Rv0009

PROBABLE IRON-REGULATED PEPTIDYL-PROLYL CIS-TRANS ISOMERASE A
PPIA (PPIase A) (ROTAMASE A)
5' primer:
GAAGGAGATATACCATGCATCATCATCATCATCATATGGCAGACTGTGAT (SEQ ID
NO:30)

TABLE 1-continued

Immunogenic Mtb Polypeptides: Primers, Polynucleotide
Sequences, and Amino Acid Sequences 3' primer:
TGATGATGAGAACCCCCCCCGGAGATGGTGATCGACTCGA (SEQ ID NO:31)

Polynucleotide sequence:
ATGGCAGACTGTGATTCCGTGACTAACAGCCCCCTTGCGACCGCTACCGCCACGCTGCACAC
TAACCQCGGCGACATCAAGATCGCCCTGTTCGGAAACCATGCGCCCAAGACCGTCGCCAATT
TTGTGGGCCTTGCGCAGGGCACCAAGGACTATTCGACCCAAAACGCATCAGGTGGCCCGTCC
GGCCCGTTCTACGACGGCGCGGTCTTTCACCGGGTGATCCAGGGCTTCATGATCCAGGGTGG
CGATCCAACCGGGACGGGTCGCGGCGGACCCGGCTACAAGTTCGCCGACGAGTTCCACCCCG
AGCTGCAATTCGACAAGCCCTATCTGCTCGCGATGGCCAACGCCGGTCCGGGCACCAACGGC
TCACAGTTTTTCATCACCGTCGGCAAGACTCCGCACCTGAACCGGCGCCACACCATTTTCGG
TGAAGTGATCGACGCGGAGTCACAGCGGGTTGTGGAGGCGATCTCCAAGACGGCCACCGACG
GCAACGATCGGCCGACGGACCCGGTGGTGATCGAGTCGATCACCATCTCC 549 bp
(SEQ ID NO:57)

Amino acid sequence:
MADCDSVTNSPLATATATLHTNRGDIKIALFGNHAPKTVANFVGLAQGTKDYSTQNASGGPS
GPFYDGAVFHRVIQGFMIQGGDPTGTGRGGPGYKFADEFHPELQFDKPYLLAMANAGPGTNG
SQFFITVGKTPHLNRRHTIFGEVIDAESQRVVEAISKTATDGNDRPTDPVVIESITIS
(SEQ ID NO:76)

Rv1073

CONSERVED HYPOTHETICAL PROTEIN
5' primer:
GAAGGAGATATACCATGCATCATCATCATCATCATATGGGGGCGCAGCCG (SEQ ID NO:32)

3' primer:
TGATGATGAGAACCCCCCCCACGTCGTGATGTCAACGTGT (SEQ ID NO:33)

Polynucleotide sequence:
ATGGGGGCGCAGCCGTTCATCGGCAGCGAGGCGTTGGCGGCGGGACTCATCAGCTGGCATGA
GCTGGGCAAGTACTACACCGCGATCATGCCCAACGTCTATCTGGACAAGCGGCTGAAGCCCT
CCCTGCGGCAACGCGTTATCGCGGCCTGGCTGTGGTCGGGCCGCAAAGGGGTGATCGCCGGC
GCTTCGGCATCAGCGCTGCACGGCGCGAAATGGGTCGATGACCACGCATTGGTGGAGTTGAT
CTGGCGCAACGCCAGGGCGCCGAACGGGGTGCGGACTAAGGATGAGCTACTGCTCGACGGCG
AAGTCCAGCGCTTGTGCGGGCTTACTGTGACTACCGTTGAACGTACGGCCTTCGACTTGGGC
AGGCGTCCACCCTTAGGTCAGGCGATAACCAGACTGGATGCGCTTGCCAATGCCACCGATTT
CAAGATCAACGATGTTAGGGAGCTCGCGAGGAAGCACCCCCATACTCGCGGGCTGCGTCAAC
TAGACAAGGCGCTGGATCTCGTCGACCCAGGTGCGCAGTCGCCGAAGGAGACGTGGCTGCGG
CTCTTGCTGATAAACGCCGGCTTTCCACGGCCGTCCACTCAGATCCCCTTGCTCGGCGTCTA
CGGGCATCCAAAGTATTTCCTCGACATGGGATGGGAGGACATCATGCTCGCGGTCGAGTACG
ACGGCGAGCAACACCGTCTCAGCCGAGACCAGTTCGTCAAAGACGTCGAACGCCTGGAATAC
ATCCGGCGCGCCGGCTGGACTCACATCAGGGTGCTGGCAGACCACAAGGGACCCGACGTCGT
CCGCCGGGTTCGGCAGGCTTGGGACACGTTGACATCACGACGT 852 bp (SEQ ID NO:58)

Amino acid sequence:
MGAQPFIGSEALAAGLISWHELGKYYTAIMPNVYLDKRLKPSLRQRVIAAWLWSGRKGVIAG
ASASALHGAKWVDDHALVELIWRNARAPNGVRTKDELLLDGEVQRLCGLTVTTVERTAFDLG
RRPPLGQAITRLDALANATDFKINDVRELARKHPHTRGLRQLDKALDLVDPGAQSPKETWLR
LLLINAGFPRPSTQIPLLGVYGHPKYFLDMGWEDIMLAVEYDGEQHRLSRDQFVKDVERLEY
IRRAGWTHIRVLADHKGPDVVRRVRQAWDTLTSRR (SEQ ID NO:77)

Rv0781

PROBABLE PROTEASE II PTRBA [FIRST PART] (OLIGOPEPTIDASE B)
5' primer:
GAAGGAGATATACCATGCATCATCATCATCATCATATGATGCACCGAACC (SEQ ID NO:34)

3' primer:
TGATGATGAGAACCCCCCCCTCGGCTTCGTGGTAAACCCG (SEQ ID NO:35)

Polynucleotide sequence:
ATGATGCACCGAACCGCACTACCCTCACCGCCCGTGGCCAAGCGGGTGCAGACCCGC:
CGGGAGCACCACGGCGACGTCTTTGTCGACCCATATGAATGGTTGCGCGACAAGGACAGCCC
TGAAGTAATCGCCTACCTCGAAGCTGAAAACGACTACACCGAACGGACCACCGCGCACCTTG
AGCCATTGCGGCAAAAGATCTTCCACGAAATCAAAGCGCGTACCAAGGAAACCGACTTATCG
GTGCCGACGCGACGTGGCAACTGGTGGTACTACGCGCGGACCTTTGAGGGAAAGCAGTATGG
CGTACACTGTCGTTGCCCGGTAACCGATCCCGACGACTGGAACCCACCAGAGTTCGACGAGC
GCACCGAAATACCCGGTGAACAGCTTCTGCTCGACGAGAACGTGGAAGCTGACGGCCACGAC
TTCTTCGCACTGGGCGCGGCCAGCGTCAGCCTGGACGATAACCTCTTAGCGTATTCCGTTGA
TGTCGTAGGTGACGAACGATATACCTTGCGGTTCAAGGATTTACGCACCGGAGAACAGTACC TABLE 1-continued Immunogenic Mtb Polypeptides: Primers, Polynucleotide
Sequences, and Amino Acid Sequences CGGACGAGATCGCCGGGATCGGAGCGGGAGTCACCTGGGCAGCTGACAACCACTGTCTACTA
CACCACCGTGGACGCGGCCTGGCGTCCGGACACAGTGTGGCGATACCGACTAGGGTCCGGCG
AATCGTCGGAGCGGGTTTACCACGAAGCCGA 711 bp (SEQ ID NO:59)

Amino acid sequence:
MMHRTALPSPPVAKRVQTRREHHGDVFVDPYEWLRDKDSPEVIAYLEAENDYTERTTAHLEP
LRQKIFHEIKARTKETDLSVPTRRGNWWYYARTFEGKQYGVHCRCPVTDPDDWNPPEFDERT
EIPGEQLLLDENVEADGHDFFALGAASVSLDDNLLAYSVDVVGDERYTLRFKDLRTGEQYPD
EIAGIGAGVTWAADNHCLLHHRGRGLASGHSVAIPTRVRRIVGAGLPRSR (SEQ ID
NO:78)

Rv2108

PPE FAMILY PROTEIN
5' primer:
GAAGGAGATATACCATGCATCATCATCATCATCATATGCCCAATTTCTGG (SEQ ID
NO:36)

3' primer:
TGATGATGAGAACCCCCCCCAAACTTAGGATGTTCCTTGT (SEQ ID NO:37)

Polynucleotide sequence:
ATGCCCAATTTCTGGGCGTTGCCGCCCGAGATCAACTCCACCCGGATATATCTCGGCCCGGG
TTCTGGCCCGATACTGGCCGCCGCCCAGGGATGGAACGCTCTGGCCAGTGAGCTGGAAAAGA
CGAAGGTGGGGTTGCAGTCAGCGCTCGACACGTTGCTGGAGTCGTATAGGGGTCAGTCGTCG
CAGGCTTTGATACAGCAGACCTTGCCGTATGTGCAGTGGCTGACCACGACCGCCGAGCACGC
CCATAAGACCGCGATCCAGCTCACGGCAGCGGCGAACGCCTACGAGCAGGCTAGAGCGGCGA
TGGTGCCGCCGGCGATGGTGCGCGCGAACCGCGTGCAGACCACAGTGTTGAAGGCAATCAAC
TGGTTCGGGCAATTCTCCACCAGGATCGCCGACAAGGAGGCCGACTACGAACAGATGTGGTT
CCAAGACGCGCTAGTGATGGAGAACTATTGGGAAGCCGTGCAAGAGGCGATACAGTCGACGT
CGCATTTTGAGGATCCACCGGAGATGGCCGACGACTACGACGAGGCCTGGATGCTCAACACC
GTGTTCGACTATCACAACGAGAACGCAAAGAGGAGGTCATCCATCTCGTGCCCGACGTGAA
CAAGGAGAGGGGGCCCATCGAACTCGTAACCAAGGTAGACAAAGAGGGGACCATCAGACTCG
TCTACGATGGGGAGCCCACGTTTTCATACAAGGAACATCCTAAGTTT 732 bp
(SEQ ID NO:60)

Amino acid sequence:
MPNFWALPPEINSTRIYLGPGSGPILAAAQGWNALASELEKTKVGLQSALDTLLESYRGQSS
QALIQQTLPYVQWLTTTAEHAHKTAIQLTAAANAYEQARAAMVPPAMVRANRVQTTVLKAIN
WFGQFSTRIADKEADYEQMWFQDALVMENYWEAVQEAIQSTSHFEDPPEMADDYDEAWMLNT
VFDYHNENAKEEVIHLVPDVNKERGPIELVTKVDKEGTIRLVYDGEPTFSYKEHPKF (SEQ
ID NO:79)

Rv3920c

HYPOTHETICAL PROTEIN SIMILAR TO JAG PROTEIN
5' primer:
GAAGGAGATATACCATGCATCATCATCATCATCATATGGCCGACGCTGAC (SEQ ID
NO:38)

3' primer:
TGATGATGAGAACCCCCCCCGTCGCGGAGCACAACGACTC (SEQ ID NO:39)

Polynucleotide sequence:
ATGGCCGACGCTGACACCACCGACTTCGACGTCGACGCAGAAGCACCGGGTGGAGGCGTCCG
GGAGGACACGGCGACGGATGCTGACGAGGCCGACGATCAAGAAGAGAGATTGGTCGCCGAGG
GCGAGATTGCAGGCGACTACCTGGAAGAGTTATTGGACGTGTTGGACTTCGATGGCGACATC
GACCTCGATGTCGAAGGCAATCGTGCGGTGGTGAGCATCGACGGCAGTGACGACCTGAACAA
GTTGGTCGGGCGCGGGGGCGAGGTGCTCGACGCTCTGCAGGAACTCACCCGGTTGGCGGTGC
ATCAGAAGACCGGTGTGCGGAGCCGGTTGATGCTAGACATCGCGAGGTGGCGACGGCGGCGC
CGGGAGGAATTGGCGGCGCTGGCCGACGAGGTGGCGCGGCGAGTGGCCGAAACCGGTGACCG
CGAGGAACTCGTTCCAATGACGCCGTTCGAACGGAAGATCGTCCACGATGCGGTTGCAGCGG
TGCCAGGTGTGCACAGCGAAAGCGAAGGCGTGGAGCCAGAACGCCGAGTCGTTGTGCTCCGC
GAC 564 (SEQ ID NO:61)

Amino acid sequence:
MADADTTDFDVDAEAPGGVREDTATDADEADDQEERLVAEGEIAGDYLEELLDVLDFDGDI
DLDVEGNRAVVSIDGSDDLNKLVGRGGEVLDALQELTRLAVHQKTGVRSRLMLDIARWRRRR
REELAALADEVARRVAETGDREELVPMTPFERKIVHDAVAAVPGVHSESEGVEPERRVVVLR
D (SEQ ID NO:80)

TABLE 1-continued

Immunogenic Mtb Polypeptides: Primers, Polynucleotide
Sequences, and Amino Acid Sequences Rv1044

CONSERVED HYPOTHETICAL PROTEIN
5' primer:
GAAGGAGATATACCATGCATCATCATCATCATCATTTGTGTGCAAAACCG (SEQ ID
NO:40)

3' primer:
TGATGATGAGAACCCCCCCCCGCCGATGCTCGCTTCGGCC (SEQ ID NO:41)

Polynucleotide sequence:
TTGTGTGCAAAACCGTATCTAATTGATACGATTGCGCACATGGCTATCTGGGATCGCCTCGT
CGAGGTTGCCGCCGAGCAACATGGCTACGTCACGACTCGCGATGCGCGAGACATCGGCGTCG
ACCCTGTGCAGCTCCGCCTCCTAGCGGGGCGCGGACGTCTTGAGCGTGTCGGCCGAGGTGTG
TACCGGGTGCCCGTGCTGCCGCGTGGTGAGCACGACGATCTCGCAGCCGCAGTGTCGTGGAC
TTTGGGGCGTGGCGTTATCTCGCATGAGTCGGCCTTGGCGCTTCATGCCCTCGCTGACGTGA
ACCCGTCGCGCATCCATCTCACCGTCCCGCGCAACAACCATCCGCGTGCGGCCGGGGGCGAG
CTGTACCGAGTTCACCGCCGCGACCTCCAGGCAGCCCACGTCACTTCGGTCGACGGAATACC
CGTCACGACGGTTGCGCGCACCATCAAAGACTGCGTGAAGACGGGCACGGATCCTTATCAGC
TTCGGGCCGCGATCGAGCGAGCCGAAGCCGAGGGCACGCTTCGTCGTGGGTCAGCAGCTGAG
CTACGCGCTGCGCTCGATGAGACCACTGCCGGATTACGCGCTCGGCCGAAGCGAGCATCGGC
G 624 bp (SEQ ID NO:62)

Amino acid sequence:
LCAKPYLIDTIAHMAIWDRLVEVAAEQHGYVTTRDARDIGVDPVQLRLLAGRGRLERVGRGV
YRVPVLPRGEHDDLAAAVSWTLGRGVISHESALALHALADVNPSRIHLTVPRNNHPRAAGGE
LYRVHRRDLQAAHVTSVDGIPVTTVARTIKDCVKTGTDPYQLRAAIERAEAEGTLRRGSAAE
LRAALDETTAGLRARPKRASA(SEQ ID NO:81)

Rv2882c

RIBOSOME RECYCLING FACTOR FRR (RIBOSOME RELEASING FACTOR)
(RRF)
5' primer:
GAAGGAGATATACCATGCATCATCATCATCATCATATGATTGATGAGGCT (SEQ ID
NO:42)

3' primer:
TGATGATGAGAACCCCCCCCGACCTCCAGCAGCTCGCCTT (SEQ ID NO:43)

Polynucleotide sequence:
ATGATTGATGAGGCTCTCTTCGACGCCGAAGAGAAAATGGAGAAGGCTGTGGCGGTGGCACG
TGACGACCTGTCAACTATCCGTACCGGCCGCGCCAACCCTGGCATGTTCTCTCGGATCACCA
TCGACTACTACGGTGCGGCCACCCCGATCACGCAACTGGCCAGCATCAATGTCCCCGAGGCG
CGGCTAGTCGTGATAAAGCCGTATGAAGCCAATCAGTTGCGCGCTATCGAGACTGCAATTCG
CAACTCCGACCTTGGAGTGAATCCCACCAACGACGGCGCCCTTATTCGCGTGGCCGTACCGC
AGCTCACCGAAGAACGTCGGCGAGAGCTGGTCAAACAGGCAAAGCATAAGGGGGAGGAGGCC
AAGGTTTCGGTGCGTAATATCCGTCGCAAAGCGATGGAGGAACTCCATCGCATCCGTAAGGA
AGGCGAGGCCGGCGAGGATGAGGTCGGTCGCGCAGAAAAGGATCTCGACAAGACCACGCACC
AATACGTCACCCAAATTGATGAGCTGGTTAAACACAAAGAAGGCGAGCTGCTGGAGGTC
558 bp (SEQ ID NO:63)

Amino acid sequence:
MIDEALFDAEEKMEKAVAVARDDLSTIRTGRANPGMFSRITIDYYGAATPITQLASINVPEA
RLVVIKPYEANQLRAIETAIRNSDLGVNPTNDGALIRVAVPQLTEERRRELVKQAKHKGEEA
KVSVRNIRRKAMEELHRIRKEGEAGEDEVGRAEKDLDKTTHQYVTQIDELVKHKEGELLEV
(SEQ ID NO:82)

Rv3733c

CONSERVED HYPOTHETICAL PROTEIN
5' primer:
GAAGGAGATATACCATGCATCATCATCATCATCATATGCCCAAGCTCAGC (SEQ ID
NO.:44)

3' primer:
TGATGATGAGAACCCCCCCCGCGAGGCAGGGATTCTGGTC (SEQ ID NO:45)

Polynucleotide sequence:
ATGCCCAAGCTCAGCGCGGGTGTGCTGCTGTATCGGGCGCGCGCCGGTGTCGTCGACGTCCT
TCTGGCCATCCGGGCGGCCCGTTTTGGGCGGGAAAGGACGACGGCGCTTGGTCGATCCCGA
AGGGCGAATACACCGGCGGCGAAGATCCGTGGCTGGCCGCCCGGCGCGAGTTCTCCGAGGAG
ATCGGGTTGTGCGTGCCTGACGGGCCGCGAATCGACTTCGGGTCGCTGAAACAGTCCGGCGG
CAAGGTGGTGACCGTGTTCGGTGTCCGGGCGGATCTGGACATCACCGACGCACGAAGCAGCA
CCTTCGAATTGGACTGGCCGAAGGGCTCGGGCAAGATGCGTAAGTTCCCCGAGGTCGACCGG TABLE 1-continued Immunogenic Mtb Polypeptides: Primers, Polynucleotide
Sequences, and Amino Acid Sequences

GTGAGCT

TABLE 1-continued

Immunogenic Mtb Polypeptides: Primers, Polynucleotide
Sequences, and Amino Acid Sequences GCACCAAGCTCGGCGTGGAAGCCAAACGCTACTTGGATGCCGGTGACTTGGTGCCGTCCGAC
TTGACCAATGAACTCGTCGACGACCGGCTGAACAATCCGGACGCGGCCAACGGATTCATCTT
GGATGGCTATCCACGCTCGGTCGAGCAGGCCAAGGCGCTTCACGAGATGCTCGAACGCGGG
GGACCGACATCGACGCGGTGCTGGAGTTTCGTGTGTCCGAGGAGGTGTTGTTGGAGCGACTC
AAGGGGCGTGGCCGCGCCGACGACACCGACGACGTCATCCTCAACCGGATGAAGGTCTACCG
CGACGAGACCGCGCCGCTGCTGGAGTACTACCGCGACCAATTGAAGACCGTCGACGCCGTCG
GCACCATGGACGAGGTGTTCGCCCGTGCGTTGCGGGCTCTGGGAAAG (SEQ ID
NO:112)

Amino acid sequence:
VRVLLLGPPGAGKGTQAVKLAEKLGIPQISTGELFRRNIEEGTKLGVEAKRYLDAGDLVP
SDLTNELVDDRLNNPDAANGFILDGYPRSVEQAKALHEMLERRGTDIDAVLEFRVSEEVL
LERLKGRGRADDTDDVILNRMKVYRDETAPLLEYYRDQLKTVDAVGTMDEVFARALRALG
K (SEQ ID NO:124)

Rv1065

CONSERVED HYPOTHETICAL PROTEIN
5' primer:
GAAGGAGATATACCATGCATCATCATCATCATCATGTGGTTATGCCTCTT (SEQ ID
NO:92)

3' primer:
TGATGATGAGAACCCCCCCCTCCCGACCCTTCGGGCTGGT (SEQ ID NO:93)

Polynucleotide sequence:
GTGGTTATGCCTCTTGTCACGCCAACCACCGCGGTTCCATCACCGGGACCCACACGGCTGCG
TGTAGCCGATCTCCTGCGCGCCACCGACCAAGCCGCAGACGACGTGCTTGGCGGGCGCTGCG
ACCACCTGCTACCCGACGGTGGTGTCCCGCAGACGCAGCGCTGGTACACCCGCATCCACGGT
GACGAGGAGCTGGATATCTGGCTGATTAGCTGGGTTCCCGGTCAACCGACCGAGCTGCACGA
CCATGGCGGGTCCCTGGGAGCGTTGACCGTGCTGAGCGGGTCGCTCAACGAATATCGTTGGG
ACGGCCGTCGGTTGCGACGGCGCCGCCTCGATGCCGGTGATCAGGCAGGGTTCCCGTTGGGT
TGGGTGCACGACGTGGTGTGGGCGCCCCGGCCGATTGGGGGGCCTGATGCGGCCGGGATGGC
TGTGGCGCCAACCCTGAGCGTGCACGCCTACTCGCCGCCGCTGACGGCGATGTCGTACTACG
AGATCACCGAACGCAACACGCTGCGCCGCCAGCGCACCGAATTGACCGACCAGCCCGAAGGG
TCGGGA (SEQ ID NO:113)

Amino acid sequence:
VVMPLVTPTTAVPSPGPTRLRVADLLRATDQAADDVLGGRCDHLLPDGGVPQTQRWYTRI
HGDEELDIWLISWVPGQPTELHDHGGSLGALTVLSGSLNEYRWDGRRLRRRRLDAGDQAG
FPLGWVHDVVWAPRPIGGPDAAGMAVAPTLSVHAYSPPLTAMSYYEITERNTLRRQRTEL
TDQPEGSG (SEQ ID NO:125)

Rv2114

HYPOTHETICAL PROTEIN
5' primer:
GAAGGAGATATACCATGCATCATCATCATCATCATATGTCGGCTCCCGAA (SEQ ID
NO:94)

3' primer:
TGATGATGAGAACCCCCCCCGGCGGTCACCAGCGAGTAGC (SEQ ID NO:95)

Polynucleotide sequence:
ATGTCGGCTCCCGAACGGGTAACCGGCTTGTCCGGGCAACGTTACGGGGAAGTCCTTCTCGT
AACACCCGGGGAGGCCGGTCCACAGGCCACCGTTTACAACAGCTTCCCGCTTAACGATTGTC
CGGCCGAGCTGTGGTCCGCGCTCGATCCGCAAGCCCTAGCCACCGAACACAAAGCGGCCACC
GCCCTGCTCAACGGTCCGCGCTATTGGTTGATGAACGCCATCGAGAAGGCGCCCCAGGGCCC
GCCGGTGACGAAGACCTTCGGCGGGATCGAGATGCTCCAGCAGGCCACGGTGCTGCTGTCAT
CGATGAACCCTGCCCCATACACCGTCAGCCAGGTCAGCCGCAACACGGTCTTTGTGTTCAAC
GCCGGCGAAGAGGTCTACGAACTGCAGGACCCCAAGGGACAGCGCTGGGTGATGCAGACGTG
GAGTCAAGTGGTGGACCCCAACCTGTCCCGAGCCGACCTGCCCAAGCTGGGTGAACGGCTCA
ACCTGCCAGCCGGGTGGTCCTATCATACCCGCGTGCTTACCAGCGAGTTGCGGGTCGACACT
ACCAACCGGGAGGCCCGCGTCCTGCAAGACGACCTCACCAACAGCTACTCGCTGGTGACCGC
C (SEQ ID NO:114)

Amino acid sequence:
MSAPERVTGLSGQRYGEVLLVTPGEAGPQATVYNSFPLNDCPAELWSALDPQALATEHKA
ATALLNGPRYWLMNAIEKAPQGPPVTKTFGGIEMLQQATVLLSSMNPAPYTVSQVSRNTV
FVFNAGEEVYELQDPKGQRWVMQTWSQVVDPNLSRADLPKLGERLNLPAGWSYHTRVLTS
ELRVDTTNREARVLQDDLTNSYSLVTA (SEQ ID NO:126)

TABLE 1-continued

Immunogenic Mtb Polypeptides: Primers, Polynucleotide
Sequences, and Amino Acid Sequences Rv2466c CONSERVED HYPOTHETICAL PROTEIN
5' primer:
GAAGGAGATATACCATGCATCATCATCATCATCATATGCTCGAGAAGGCC (SEQ ID
NO:96)
3' primer:
TGATGATGAGAACCCCCCCGTCGAACTGAGGCGGCTCGG (SEQ ID NO:97)

Polynucleotide sequence:
ATGCTCGAGAAGGCCCCCCAGAAGTCTGTCGCCGATTTCTGGTTCGATCCGCTGTGCCCGTG
GTGCTGGATCACGTCGCGCTGGATCCTCGAGGTGGCAAAGGTCCGCGACATCGAGGTGAACT
TCCACGTCATGAGCCTGGCAATACTCAACGAAAACCGTGACGACCTGCCCGAGCAATACCGC
GAAGGCATGGCGAGGGCATGGGGACCGGTACGGGTGGCGATCGCCGCCGAGCAGGCCCATGG
GGCGAAAGTCCTGGACCCGCTGTACACCGCGATGGGCAACCGGATTCACAACCAGGGCAACC
ACGAACTCGACGAGGTCATCACCCAGTCGCTGGCGGACGCCGGTCTGCCCGCGGAGTTGGCC
AAGGCCGCTACCAGCGACGCTTACGACAACGCCCTGCGCAAAAGCCACCACGCCGGGATGGA
CGCGGTGGGCGAGGACGTCGGTACGCCGACGATCCATGTCAATGGTGTGGCGTTCTTCGGGC
CGGTGCTCTCGAAGATTCCGCGCGGCGAGGAAGCCGGCAAGCTCTGGGATGCCTCGGTTACC
TTCGCTTCCTACCCGCACTTTTTTGAGCTCAAGCGGACCCGCACCGAGCCGCCTCAGTTCGA
C (SEQ ID NO:115)

Amino acid sequence:
MLEKAPQKSVADFWFDPLCPWCWITSRWILEVAKVRDIEVNFHVMSLAILNENRDDLPEQ
YREGMARAWGPVRVAIAAEQAHGAKVLDPLYTAMGNRIHNQGNHELDEVITQSLADAGLP
AELAKAATSDAYDNALRKSHHAGMDAVGEDVGTPTIHVNGVAFFGPVLSKIPRGEEAGKL
WDASVTFASYPHFFELKRTRTEPPQFD (SEQ ID NO:127)

Rv0158

PROBABLE TRANSCRIPTIONAL REGULATORY PROTEIN (POSSIBLY TETR-
FAMILY)
5' primer:
GAAGGAGATATACCATGCATCATCATCATCATCATATGCCATCCGACACC (SEQ ID
NO:98)

3' primer:
TGATGATGAGAACCCCCCCCCGTTTCCTTCCGAGTTCCAA (SEQ ID NO:99)

Polynucleotide sequence:
ATGCCATCCGACACCAGCCCCAACGGGCTAAGCCGCCGTGAGGAGTTGCTGGCTGTTGCCAC
CAAACTATTCGCGGCGCGCGGTTATCACGGCACCCGGATGGACGACGTCGCCGATGTGATCG
GGCTCAACAAAGCAACGGTCTATCACTACTACGCCAGCAAGTCGCTGATCCTGTTCGACATT
TACCGTCAGGCGGCCGAGGGCACCCTGGCCGCCGTGCACGACGATCCGTCCTGGACGGCCCG
TGAAGCGCTGTACCAGTACACGGTCCGGCTGCTCACTGCGATCGCGAGCAACCCCGAGCGGG
CCGCCGTGTACTTCCAGGAGCAGCCCTACATCACCGAGTGGTTCACCCAGCGAGCAGGTCGCC
GAGGTCCGCGAGAAGGAGCAGCAAGTCTACGAGCACGTACACGGCCTGATCGACCGCGGGAT
TGCCAGCGGCGAGTTCTATGAGTGCGACTCGCATGTGGTGGCGCTGGGGTACATCGGGATGA
CGCTGGGCAGCTACCGCTGGCTGCGGCCGAGCGGGCGCCGAACGGCAAGGAGATCGCGGCG
GAGTTCAGCACGGCACTGCTGCGCGGGCTGATCCGCGACGAATCGATCCGCAACCAGTCTCC
GCTTGGAACTCGGAAGGAAACG (SEQ ID NO:116)

Amino acid sequence:
MPSDTSPNGLSRREELLAVATKLFAARGYHGTRMDDVADVIGLNKATVYHYYASKSLILF
DIYRQAAEGTLAAVHDDPSWTAREALYQYTVRLLTAIASNPERAAVYFQEQPYITEWFTS
EQVAEVREKEQQVYEHVHGLIDRGIASGEFYECDSHVVALGYIGMTLGSYRWLRPSGRRT
AKEIAAEFSTALLRGLIRDESIRNQSPLGTRKET (SEQ ID NO:128)

Rv3676

PROBABLE TRANSCRIPTIONAL REGULATORY PROTEIN (PROBABLY CRP/
FNR-FAMILY)
5' primer:
GAAGGAGATATACCATGCATCATCATCATCATCATGTGGACGAGATCCTG (SEQ ID
NO:100)

3' primer:
TGATGATGAGAACCCCCCCCCCTCGCTCGGCGGGCCAGTC (SEQ ID NO:101)

Polynucleotide sequence:
GTGGACGAGATCCTGGCCAGGGCAGGAATCTTCCAAGGCGTGGAGCCCAGCGCAATCGCCGC
ACTGACGAAACAGCTGCAGCCCGTCGACTTCCCCCGTGGACACACGGTCTTCGCGGAAGGGG
AGCCGGGCGATCGGCTGTACATCATCATCTCGGGGAAGGTCAAGATCGGTCGCCGGGCACCA
GACGGCCGAGAAACCTGTTAACCATCATGGGCCCGTCGGACATGTTCGGCGAGTTGTCGAT
CTTCGACCCGGGTCCGCGCACGTCCAGCGCGACCACGATCACCGAGGTGCGGGCGGTGTCGA TABLE 1-continued Immunogenic Mtb Polypeptides: Primers, Polynucleotide
Sequences, and Amino Acid Sequences TGGACCGCGACGCGCTGCGGTCATGGATCGCCGATCGTCCCGAAATCTCCGAACAGCTGCTG
CGGGTGCTGGCCCGCCGGCTGCGCCGCACCAACAACAACCTGGCCGACCTCATCTTCACCGA
TGTGCCCGGTCGGGTGGCCAAGCAGCTGTTGCAGCTCGCCCAGCGTTTCGGCACCCAGGAAG
GTGGCGCATTGCGGGTCACCCACGACCTGACACAGGAAGAAATCGCCCAGCTGGTCGGGGCC
TCACGCGAGACGGTGAACAAGGCACTGGCTGATTTCGCTCACCGCGGCTGGATCCGCCTTGA
GGGCAAGAGTGTGCTGATCTCTGACTCCGAAAGACTGGCCCGCCGAGCGAGG (SEQ ID
NO:117)

Amino acid sequence:
VDEILARAGIFQGVEPSAIAALTKQLQPVDFPRGHTVFAEGEPGDRLYIIISGKVKIGRR
APDGRENLLTIMGPSDMFGELSIFDPGPRTSSATTITEVRAVSMDRDALRSWIADRPEIS
EQLLRVLARRLRRTNNNLADLIFTDVPGRVAKQLLQLAQRFGTQEGGALRVTHDLTQEEI
AQLVGASRETVNKALADFAHRGWIRLEGKSVLISDSERLARRAR (SEQ ID NO:129)

Rv2821c

CONSERVED HYPOTHETICAL PROTEIN
5' primer:
GAAGGAGATATACCATGCATCATCATCATCATCATATGACTACGAGCTAC (SEQ ID
NO:102)

3' primer:
TGATGATGAGAACCCCCCCAACAGCCGCGAGTTCATGGT (SEQ ID NO:103)

Polynucleotide sequence:
ATGACTACGAGCTACGCCAAGATCGAGATAACCGGGACACTGACCGTCCTGACGGGCCTGCA
GATCGGGGCCGGCGATGGCTTCTCCGCCATCGGCGCGGTCGACAAGCCTGTCGTTCGTGATC
CGCTGAGCAGGCTGCCGATGATTCCGGGTACCAGCCTGAAGGGCAAGGTCCGCACCTTGCTG
TCCCGCCAATACGGCGCCGACACAGAAACGTTTTACAGGAAGCCGAATGAGGACCACGCCCA
TATCCGTCGGCTTTTCGGCGACACCGAGGAGTACATGACGGGCCGACTCGTCTTCCGCGACA
CGAAGCTCACCAACAAAGACGACCTCGAAGCCCGCGGCGCTAAGACTCTCACCGAGGTGAAA
TTCGAGAACGCCATCAACCGGGTGACCGCAAAGGCAAACCTTCGCCAGATGGAACGCGTGAT
CCCCGGCAGCGAGTTCGCGTTCTCACTTGTCTACGAGGTCTCCTTCGGCACCCCCGGCGAGG
AACAGAAGGCGTCTCTGCCTTCCTCCGATGAGATCATCGAGGACTTCAACGCCATCGCGCGC
GGCCTGAAGTTGCTCGAACTCGACTACCTCGGCGGCAGCGGAACCCGTGGCTACGGGCAGGT
CAAGTTCAGCAACCTGAAAGCCCGCGCCGCAGTCGGCGCCCTCGACGGTTCTCTGCTGGAGA
AGCTAAACCATGAACTCGCGGCTGTT (SEQ ID NO:118)

Amino acid sequence:
MTTSYAKIEITGTLTVLTGLQIGAGDGFSAIGAVDKPVVRDPLSRLPMIPGTSLKGKVRT
LLSRQYGADTETFYRKPNEDHAHIRRLFGDTEEYMTGRLVFRDTKLTNKDDLEARGAKTL
TEVKFENAINRVTAKANLRQMERVIPGSEFAFSLVYEVSFGTPGEEQKASLPSSDEIIED
FNAIARGLKLLELDYLGGSGTRGYGQVKFSNLKARAAVGALDGSLLEKLNHELAAV
(SEQ ID NO:130)

Rv1056

CONSERVED HYPOTHETICAL PROTEIN
5' primer:
GAAGGAGATATACCATGCATCATCATCATCATCATATGAGCGTGGATTAC (SEQ ID
NO:104)

3' primer:
TGATGATGAGAACCCCCCCCGCTGAACTGAGTGTGCGGCC (SEQ ID NO:105)

Polynucleotide sequence:
ATGAGCGTGGATTACCCCCAAATGGCTGCTACCCGGGGAAGAATAGAACCGGCCCCGCGGCG
AGTTCGCGGCTATCTCGGACATGTGCTCGTCTTCGACACCAGTGCGGCGCGCTATGTCTGGG
AGGTTCCCTACTACCCGCAGTACTACATCCCGCTGGCGGATTCCGCATGGAGTTCCTGCGC
GACGAGAACCACCCGCAGCGAGTGCAGCTGGGTCCGTCGCGGCTGCACTCCTTGGTAAGCGC
CGGTCAGACCCACCGATCGGCGGCGCGGGTATTCGATGTCGACGGCGACAGCCCGGTGGCGG
GCACCGTGCGTTTCAACTGGGATCCGCTGCGGTGGTTCGAGGAGGACGAGCCGATCTACGGC
CATCCGCGCAATCCCTATCAGCGGGCCGATGCGTGCGCTCGCACCGACACGTCCGTGTCGA
GCTGGACGGCATTGTGCTCGCTGACACCCGATCGCCCGTTCTGCTATTCGAAACTGGGATAC
CCACAAGGTATTACATCGATCCGGCCGACATCGCTTTCGAGCATCTGGAGCCCACCTCGACG
CAGACGTTGTGTCCGTACAAGGGGACGACGTCGGGCTATTGGTCTGTGCGCGTCGGCGACGC
CGTGCACCGCGACCTGGCCTGGACGTATCACTATCCACTGCCCGCCGTTGCCCCGATCGCCG
GCTGGTGGCGTTTTACAACGAGAAGGTCGACCTCACCGTCGACGGCGTCGCCCTGCCGCGG
CCGCACACTCAGTTCAGC (SEQ ID NO:119)

Amino acid sequence:
MSVDYPQMAATRGRIEPAPRRVRGYLGHVLVFDTSAARYVWEVPYYPQYYIPLADVRMEF
LRDENHPQRVQLGPSRLHSLVSAGQTHRSAARVFDVDGDSPVAGTVRFNWDPLRWFEEDE
PIYGHPRNPYQRADALRSHRHVRVELDGIVLADTRSPVLLFETGIPTRYYIDPADIAFEH
LEPTSTQTLCPYKGTTSGYWSRVGDAVHRDLAWTYHYPLPAVAPIAGLVAFYNEKVDLT
VDGVALPRPHTQFS (SEQ ID NO:131)

TABLE 1-continued

Immunogenic Mtb Polypeptides: Primers, Polynucleotide
Sequences, and Amino Acid Sequences Rv1353c PROBABLE TRANSCRIPTIONAL REGULATORY PROTEIN
5' primer:
GAAGGAGATATACCATGCATCATCATCATCATCATATGCAGACAACCCCA (SEQ ID
NO:106)

3' primer:
TGATGATGAGAACCCCCCCCACGCGCCACCGCTTTGGCCC (SEQ ID NO:107)

Polynucleotide sequence:
ATGCAGACAACCCCAGGCAAGCGTCAACGACGGCAGCGCGGATCCATCAACCCCGAGGACAT
CATCAGCGGCGCATTCGAACTCGCCCAGCAGGTATCGATAGACAACTTGAGCATGCCATTGC
TCGGCAAACACCTTGGCGTCGGGGTCACCAGCATCTACTGGTACTTCCGCAAGAAGGACGAT
CTGCTCAACGCGATGACCGACCGCGCTTTGAGCAAGTACGTGTTCGCTACCCCGTACATCGA
AGCCGGCGACTGGCGCGAAACGTTGCGCAATCATGCCCGCTGATGCGGAAGACGTTCGCGG
ACAACCCCGTACTGTGCGATCTGATACTGATTCGAGCGGCGCTGTCCCCGAAAACGGCGCGG
TTGGGCGCCCAAGAGATGGAGAAGGCCATCGCCAATCTGGTGACGGCGGGCCTGTCGCTCGA
AGACGCTTTCGACATCTACTCGGCGGTTTCGGTCCACGTGCGCGGATCGGTGGTGCTAGATC
GGCTCTCCCGCAAGAGCCAGTCGGCGGGCAGCGGACCATCCGCCATTGAACACCCCGTGGCC
ATCGATCCCGCGACGACTCCGCTGCTTGCTCACGCAACTGGGAGGGGGCATCGGATCGGGGC
CCCCGATGAAACCAATTTCGAATATGGTCTCGAATGCATCCTCGACCATGCTGGCCGGTTGA
TCGAACAAAGCTCGAAAGCCGCTGGTGAGGTCGCAGTGCGCCGCCCCACGGCCACCGCCGAT
GCGCCTACGCCGGGCGCGCGGGCCAAAGCGGTGGCGCGT (SEQ ID NO:120)

Amino acid sequence:
MQTTPGKRQRRQRGSINPEDIISGAFELAQQVSIDNLSMPLLGKHLGVGVTSIYWYFRKK
DDLLNAMTDRALSKYVFATPYIEAGDWRETLRNHARSMRKTFADNPVLCDLILIRAALSP
KTARLGAQEMEKAIANLVTAGLSLEDAFDIYSAVSVHVRGSVVLDRLSRKSQSAGSGPSA
IEHPVAIDPATTPLLAHATGRGHRIGAPDETNFEYGLECILDHAGRLIEQSSKAAGEVAV
RRPTATADAPTPGARAKAVAR (SEQ ID NO:132)

Rv2528c

PROBABLE RESTRICTION SYSTEM PROTEIN MRR
5' primer:
GAAGGAGATATACCATGCATCATCATCATCATCATATGACGATCCCTGAT (SEQ ID
NO:108)

3' primer:
TGATGATGAGAACCCCCCCCCAGGCCATCAAAAAAGTCCT (SEQ ID NO:109)

Polynucleotide sequence:
ATGACGATCCCTGATGCCCAGACGTTGATGCGGCCGATTCTCGCGTATCTTGCCGATGGA
CAAGCGAAGTCGGCCAAGGACGTCATCGCGGCGATGTCCGACGAGTTCGGTCTGTCCGAC
GACGAGCGGGCGCAGATGTTGCCCAGCGGTCGGCAAAGGACCATGTACGACAGGGTGCAC
TGGTCTCTCACTCACATGTCGCAGGCCGGATTGCTCGACCGTCCCACGCGGGGCCACGTC
CAGGTCACGGACACGGGCCGTCAAGTCCTGAAGGCGCATCCCGAGCGCGTCGACATGGCT
GTGCTGCGGGAGTTCCCGTCGTACATCGCTTTTCGTGAGCGAACCAAAGCCAAGCAGCCA
GTCGACGCGACCGCCAAGCGACCGTCCGGGGACGATGTGCAGGTCTCACCCGAGGATCTC
ATCGACGCTGCGCTTGCGGAGAACCGGGCAGCCGTCGAGGGGGAGATCCTGAAGAAGGCA
CTCACGTTGTCGCCCACCGGGTTTGAAGATCTGGTTATCAGACTTTTGGAGGCGATGGGT
TACGGGCGAGCCGGCGCGGTGGAACGGACGAGTGCCTCCGGTGACGCTGGCATCGACGGA
ATCATCAGCCAGGACCCGCTCGGGCTGGACCGCATCTACGTGCAGGCCAAGCGATACGCC
GTCGACCAAACGATTGGCCGGCCGAAGATCCACGAGTTCGCCGGCGCCCTCCTGGGCAAG
CAGGGCGACCGGGGCGTCTACATCACCACGTCATCGTTTTCCCGCGGTGCCCGCGAGGAA
GCTGAGCGGATCAACGCCCGGATCGAACTCATCGACGGCGCTCGGCTGGCCGAGCTGCTC
GTGCGGTATCGAGTCGGTGTCCAGGCGGTGCAGACCGTCGAACTCTTACGGCTCGACGAG
GACTTTTTTGATGGCCTG (SEQ ID NO:121)

Amino acid sequence:
MTIPDAQTLMRPILAYLADGQAKSAKDVIAAMSDEFGLSDDERAQMLPSGRQRTMYDRVH
WSLTHMSQAGLLDRPTRGHVQVTDTGRQVLKAHPERVDMAVLREFPSYIAFRERTKAKQP
VDATAKRPSGDDVQVSPEDLIDAALAENRAAVEGEILKKALTLSPTGFEDLVIRLLEAMG
YGRAGAVERTSASGDAGIDGIISQDPLGLDRIYVQAKRYAVDQTIGRPKIHEFAGALLGK
QGDRGVYITTSSFSRGAREEAERINARIELIDGARLAELLVRYRVGVQAVQTVELLRLDE
DFFDGL (SEQ ID NO:133)

The PCR reactions contained 100 ng Mtb genomic DNA, 25 nM final concentration of 5' and 3' primers. Polymerase, PCR buffer and nucleotides were from Clontech. The reaction temperature and times for the first PCR reaction were: 94° C. for 2 minutes, followed by 30 cycles of: 94° C. for 30 seconds, 48° C. for 1 min., and 68° C. for 2.5 minutes.

Following the first PCR reaction, an aliquot of each PCR reaction containing 100 ng of PCR product from the previous step was transferred into a PCR reaction containing the TAP promoter and terminator fragments. The sequences of these fragments were:

Promoter Fragment:

(SEQ ID NO:6)
5'CGGTCACGCTTGGGACTGCCATAGGCTGGCCCGGTGATGCCGGCCACG

ATGCGTCCGGCGTAGAGGATCGAGATCTCGATCCCGCGAAATTAATACGA

CTCACTATAGGGAGACCACAACGGTTTCCCTCTAGAAATAATTTTGTTTA

ACTTTAAGAAGGAGATATACC 3'

Terminator Fragment:

(SEQ ID NO: 7)
5'GGGGGGGGTTCTCATCATCATCATCATCATTAATAAAAGGGCGAATTC

CAGCACACTGGCGGCCGTTACTAGTGGATCCGGCTGCTAACAAAGCCCGA

AAGGAAGCTGAGTTGGCTGCTGCCACCGCTGAGCAATAACTAGCATAACC

CCTTGGGGCCTCTAAACGGGTCTTGAGGGGTTTTTTGCTGAAAGGAGGAA

CTATATCCGGAGCGACTCCCACGGCACGTTGGCAAGCTCG 3'

The reaction temperature and times for the second PCR reaction were: 94° C. for 2 minutes, followed by 30 cycles of: 94° C. for 30 seconds, 48° C. for 60 seconds, and 68° C. for 2.5 minutes.

Protein Expression

The TAP fragments generated by PCR were used as templates for in vitro protein expression using a Roche RTS100 transcription/translation kit according to manufacturer's instructions. Approximately 0.5~1.0 μg PCR product was used as template, producing approximately 0.5~5.0 μg of protein per template.

Protein Purification

MagneHis nickel-coated magnetic beads (Promega) were used to purify the expressed proteins. 15 μl of Ni-magnetic beads (Promega) were pipetted into each well of a microtiter plate. To each well 50 μl wash buffer (50 mM NaHPO$_4$, pHS8.0, 300 mM NaCl, 100 mM imidazole) was added with mixing and the plates were placed on a magnetic stand. The supernatant was removed and wash was repeated. 50 μl of the protein mixture was added with gentle pipetting. The mixture was incubated at room temperature for 2 minutes. The beads were then separated using a magnetic stand, washed 3 times with 150 μl wash buffer and the bound protein was eluted from the beads with 50 μl of 50 mM NaHPO$_4$, pH 8.0, 300 mM NaCl, 250 mM imidazole.

Western Blot.

15 μl of the purified proteins were resolved on 4-12% SDS-polyacrylamide gels and transferred to nitrocellulose membranes The membranes were blocked in TBST/1% BSA, followed by incubation with TBST/1% BSA containing 1000-fold diluted rabbit anti-Mtb serum. The blots were washed and then incubated with alkaline phosphatase-conjugated goat-anti rabbit serum secondary antibody. Colorimetric development was used to develop the blots. The results of these analyses are shown in FIG. 6.

ELISA

The wells of Nunc-Immuno MaxiSorp 96-well plates were coated with 5 μl of expressed protein diluted in 95 μl PBS. The plates were mixed well on a shaker and then incubated overnight at 4° C. The plates were washed with PBS+0.05% Tween-20 for 5 min. with shaking at 200 rpm. 200 μl of PBS+1% BSA blocking solution was added and the plates incubated for 1 hr at room temperature, with shaking at 150 rpm. The blocking buffer was removed and 100 μl primary antibody (04.E293.1.11.WCL(-)LAM rabbit polyclonal antibodies 1:200000 diluted in blocking solution) was added. Following 1 hr incubation at room temperature with shaking at 150 rpm, the plates were washed 3 times with PBS+0.05% Tween-20. 100 μl second antibody (Anti-Rabbit IgG(H+L)-HRP conjugated, (Promega) diluted 1:2500 in blocking solution was added to each well and the plates were incubated for 1 hr at room temperature, with shaking at 150 rpm. After washing 3 times, 100 μl TMB substrate solution (Promega) was added to each well and the blue color was allowed to develop for 15 min at room temperature without shaking. 100 μl of 1N HCl was added to each well to stop the reaction and change the blue color to yellow. The plates were read in a specrophotometer at 450 nm after 30 min. The results of this analysis are shown in FIG. 6.

Figure 6:
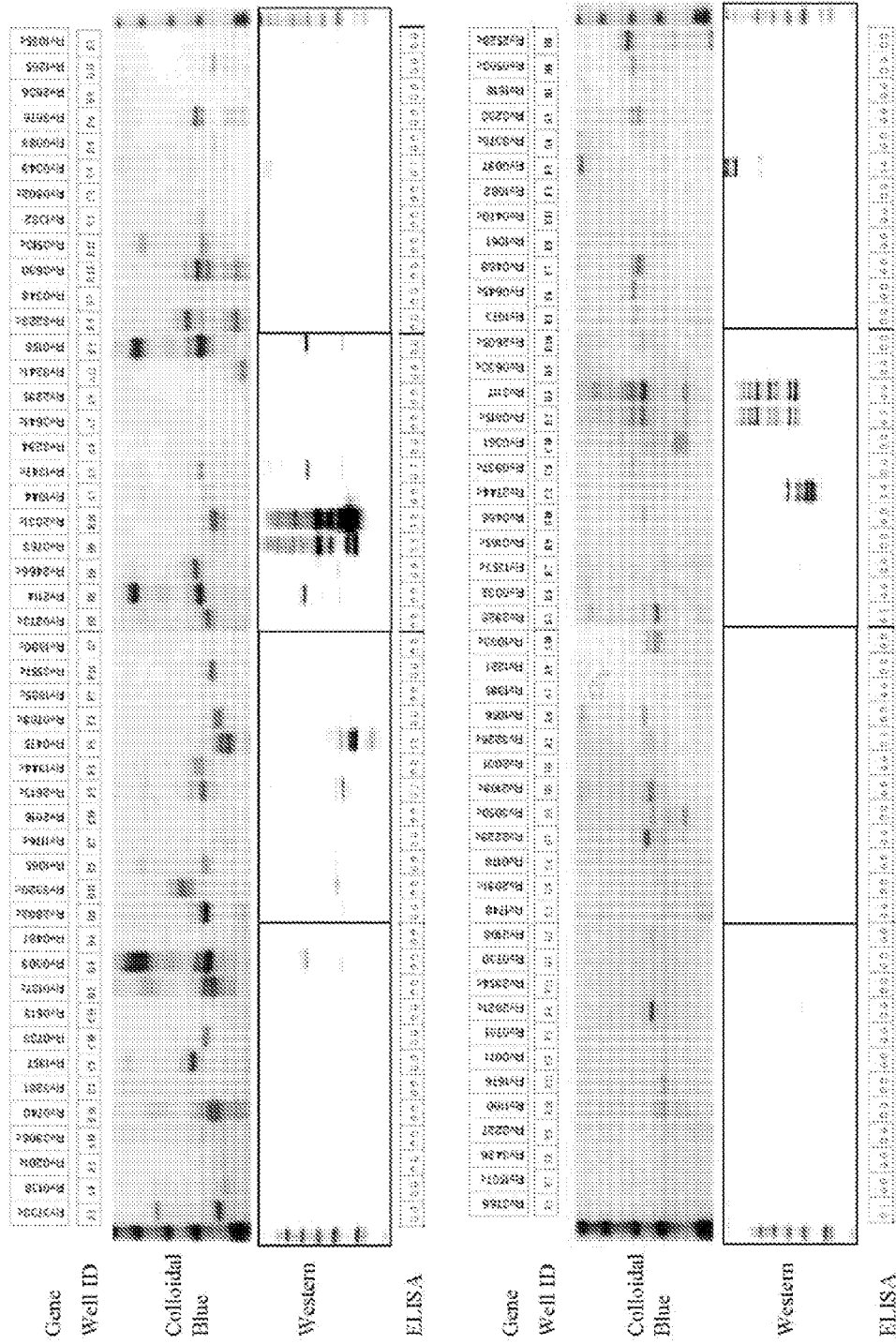
FIG. 6. shows the results of scanning the Mtb proteome for antigenic targets of humoral immunity by ELISA and Western blotting.

As shown in FIG. 6, rabbit anti-Mtb serum identified 19 and 12 proteins that were reactive to the anti-serum Western blot and ELISA, respectively. The results showed a strong correlation in 'hits' between the two methods. In addition, a few antigen proteins at low abundance exhibited high reactivity relative to the others, suggesting the presence of strong B-cell epitopes, thus making them premier candidates for additional study.

Example 3

Using the Mtb Proteome to Identify the Antigenic Targets of Cell-Mediated Immunity in Mtb Vaccinated Mice and Humans The following is a method that is used to systematically screen and identify antigens in Mtb that give rise to a protective cell-mediated immune response. Through the use of TAP technology coding sequences of the Mtb genome are amplified. The PCR reactions are performed such that each amplified coding sequence becomes transcriptionally active. The resulting TAP fragments are expressed to produce Mtb polypeptides. Each of the polypeptides is delivered into dendritic cells, located in 96-well plates, using a polypeptide delivery reagent. Serum from Mtb immunized humans is added to each of the different wells.

An IFN-γ ELIspot assay is run using the following materials and method:

Materials:

Millipore 96-well multi-screen filtration plates (Millipore #MAIP S45-10) (Millipore, Bedford, Mass.)
Anti-IFN-γ purified MAb (Clone 1-DIK) (MABTECH #3420-3) (Mabtech, Naka, Sweden)
Anti-EFN-g Biotinylated MAb (Clone 7-B6-1) (MABTECH #3420-6) (Mabtech, Naka, Sweden)
Streptavidin-Alkaline Phosphatase (MABTECH #3310-8) (Mabtech, Naka, Sweden)

Alkaline Phosphate Substrate Kit (BIO-RAD #170-6432) (Bio-Rad, Hercules, Calif.)
Carbonate Buffer pH 9.6 (0.2 µM sterile filtered)
RPMI-1640 Medium (GIBCO #22400-089) (Gibco, Grand Island, N.Y.)
Fetal Bovine Serum (Sigma #F4135-500 mL) (Sigma, St. Louis, Mo.)
1×PBS (Prepared from 10×PBS DIGENE #3400-1010) (DIGENE, Gaithersburg, Md.)
Tween® 20 (J. T. Baker #X251-07) (J. T. Baker, Phillipsburg, N.J.)

Method:

96-well plates are coated with Coating Antibody (anti-IFN-g Clone 1-DIK) at 10-15 µg/mL (100 µL/well) and incubated at 4° C. overnight. Using aseptic technique, plates are flicked to remove Coating Antibody and washed 6 times with RPMI-1640. Plates are blocked with 100 µL/well of RPMI-1640+10% FBS (or Human AB serum) for 1-2 hours at room temperature. Plates are flicked to remove blocking buffer and 100 µL/well of antigen specific or control peptides are added at a final concentration of 10 µg/well. Peripheral blood lymphocytes (PBL) are added at 4×105/well and 1×105/well. Plates are incubated at 37° C./5% $CO_2$ for 36 hours. Plates are flicked to remove cells and washed 6 times with PBS +0.05% Tween® 20 at 200-250 µL/well. Plates are blot dried on paper towels.

Biotinylated antibody (anti-IFN-g Clone 7-B6-1) diluted 1:1,000 in 1×PBS at 100 µL/well is added. The resulting solution is incubated for 3 hours at room temperature. Plates are flicked to remove biotinylated antibody and washed 6 times with PBS+0.05% Tween® 20 at 200-250 µL/well. Plates are blot dried on paper towels. Streptavidin alkaline phosphatase is added at 100 µL/well diluted 1:1,000 in 1×PBS. The plates are incubated for 1 hour at room temperature. Plates are flicked to remove the streptavidin alkaline phosphatase and washed 6 times with 0.05% Tween® 20 at 200-250 µL/well. The plates are washed again 3 times with 1×PBS at 200-250 µL/well. The plates are blot dried on paper towels.

Substrate is added at 100 µL/well for 10-15 minutes at room temperature. The substrate is prepared according to manufacturer's protocol. The 25× substrate buffer is diluted in dH20 to a 1× concentration. Reagent A & B are each diluted 1:100 in the 1× substrate buffer. Rinsing plates with generous amounts of tap water (flooding plate and flicking several times) stops colorimetric substrate. Plates are allowed to dry overnight at room temperature in the dark. Spots corresponding to IFN-γ producing cells are determined visually using a stereomicroscope (Zeiss KS ELIspot). Results can be expressed as the number of IFN-γ-secreting cells per $10^6$ spleen cells. Responses are considered positive if the response to test Mtb peptide epitope is significantly different ($p<0.05$) as compared with the response to no peptide and if the stimulation index (SI=response with test peptide/response with control peptide) is greater than 2.0.

Example 4

Cellular Vaccine Antigen Screen

A human volunteer was immunized with irradiated sporozoites from *P. falciparum*, the infectious agent responsible for malaria. Dendritic cells from the volunteer were isolated and cultured. Recombinant CSP polypeptide from *P. falciparum* was delivered to dendritic cells with or without polypeptide delivery reagents described in U.S. patent application Ser. No. 09/738046, entitled "Intracellular Protein Delivery Reagent," which is hereby incorporated by reference in its entirety. T-cells isolated from the immunized volunteer were added to the cultures. The EliSpotassay identified 120 CSP antigen specific T-cells out of 250,000 T-cells that were added to the culture when CSP was added to the culture together with said delivery reagents. When CSP was added without said delivery reagents, the signal was barely above background.

Example 5

DNA Immunization of Mice

Experiments were set up with five animals per group, consisting of four week old BALB/c female mice, averaging 40 animals per experiment. These mice were immunized IM in each tibialis anterior muscle with 50 µg plasmid DNA or transcriptionally active PCR fragment encoding selected Mtb antigens, 3 times at 3 week intervals.

Sera was collected 10 days after each immunization for antibody studies. Blood samples (~50 ul) were collected from the mice by orbital bleed with a sterilized pasture pipette. The mice were bled about once a week at a volume of approximately 50 µl.

Splenocytes were harvested at 14 days after the 3rd immunization and pooled for T-cell studies such as IFN-γ ELIspot assays. Tissue collections were performed on animals euthanized via $CO_2$ (SOP 98.19) at the end of the experiment. The experiments can be five animals/group, averaging 40 animals/experiment x 4 experiments for a total of 160 mice.

Example 6

Preparation of Human Dendritic Cells

Dendritic cells were ordered from Allcells: Cat # PB002 (NPB-Mononuclear Cells). The cells were in 50 mL buffer. The cells were counted immediately, the total number was $312.5 \times 10^6$. The cells were pelleted, and resuspended in 25 mL RPMI-1640 containing DNAse. This solution (30 µg/mL) was incubated for 5 minutes at room temperature. The cells were washed twice with complete medium. The cells were resuspended at $10 \times 10^6$ cells/3 mL. Twelve 10 mm dishes containing 10 mL complete medium in each dish were used. The cells were incubated at 37° C. for 3 hours. The non-adherent cells were removed by gently shaking plates and aspirating the supernatant. Afterwards, the dishes containing adherent cells were washed 3 times with 10 mL of RPMI-1640 containing 2% Human Serum. 10 mL of culture medium were added to each plate containing 50 ng/mL GM-CSF and 500 u/mL IL-4. This culture medium was added until day 4. After day 4, culture medium without GM-CSF and IL-4 was added. The transfection was done on day 5. The complete medium consisted of RPMI-1640 (455 mL), 5% Human AB Serum (25 mL), Non-essential Amino Acids (5 mL), Sodium Pyruvate (5 mL), L-Glutamine (5 mL), and Penicillin-Streptomycin (5 mL).

Example 7

Generation of Dendritic Cells from Mouse Bone Marrow

Cells were taken from the bones of one mouse (2 femur and 2 tibiae without removing the macrophages). The red blood cells were obtained from the bone marrow and lysed. The cells were counted (51×10⁶ cells, total) and cultured in a growth medium (2.5×10⁶ cells/plate, 10 mL/plate) for 8 days before transfection. On day 4 another 10 mL of growth medium was added. On day 6, 10 mL of the old medium was taken from each plate and the cells were pelleted. The cells were resuspended in 10 mL medium with 10 ng/mL GM-CSF and 2.5 ng/mL IL-4. The cells were placed back into the culture. The cells were cultured until transfection on day 8. On the day of transfection, 2.5×10⁶ cells were harvested from each dish. The growth medium for mbmDC contained DMEM/Iscove, 10% FCS, 50 uM β-mercaptoethanol, 1× Penicillin/Streptomycin, 2 mM L-Glutamine, 10 mM Hepes, 1× Non-essential amino acids, 20 ng/mL rmGM-CSF, and 5 ng/mL rmIL-4.

Example 8

Adding an HA Epitope Tag

Oligos were designed using TAP promoter and terminator fragments from pCMVm and pTP-SV40, respectively, and adding the nucleotide sequence encoding the HA epitope tag. For adding the HA epitope to the 5' end of the coding sequence the following sequences is used:

```
Promoter 5':
CCGCCATGTTGACATTG                            (SEQ ID NO: 2)

Promoter 3':
GGCAGATCTGGGAGGCTAGCGTAATCCGGAACATCG (SEQ ID NO: 3)
TATGGGTACATTGTTAAGTCGACGGTGC
```

For adding the HA epitope to the 3' end of the coding sequence, the following sequences is used:

```
Terminator 5':
GATCCCGGGTACCCATACGATGTTCCGGATTACGCT (SEQ ID NO: 4)
TAGGGGAGATCTCAGACATG Terminator 3':
CAGGATATCATGCCTGCAGGACGACTCTAGAG       (SEQ ID NO: 5)
```

The method includes:

PCR is used to amplify a new HA-promoter utilizing pCMVm as a template and a new HA-terminator utilizing pTP-SV40 as a template. The resulting PCR products are gel purified using QIAGEN QIAquick Gel Extraction Kit (Qiagen, Seattle, Wash.). The PCR products and both plasmids (pCMVm & pTP-SV40) are digested with EcoRV and BglII restriction enzymes. All digested products are gel purified using QIAquick Gel Extraction Kit. The HA-promoter and HA-terminator are ligated separately into the digested pCMVm and pTP-SV40 plasmids. These plasmids are transformed into DH5, grown overnight on LB plates containing Kanamycin, colonies are selected and grown in LB media containing Kanamycin. QIAGEN QIAprep Spin Miniprep Kit is used to isolate plasmids. Plasmids are digested using EcoRV and BglII. Digests are run on a gel to identify clones containing plasmid with insert of correct size. The plasmids are sequenced to confirm inserts are correct. A prep culture is grown, plasmids are isolated, plasmids are digested with EcoRV and BglII, and promoter and terminator fragments are gel purified. Epi-TAP-5 HA and Epi-TAP-3'HA kits are used.

Example 9

ICS—Intracellular Cytokine Staining (ICS)

Bone marrow derived dendritic cells (BMDCs) were prepared by culturing bone marrow cell suspensions with RPMI tissue culture media plus 10% fetal bovine serum and GM-CSF (20 ng/ml) for 6-7 days at 37° C., 5% $CO_2$. Cells were then primed with 1 μg/ml of antigen for 4 hrs at 37° C., 5% $CO_2$.

Cell suspensions obtained from naive or *M. tuberculosis* infected mice were used as a source of CD4 T cells. CD4 T cells are isolated by magnetic cell sorting and overlaid onto BMDC primed with specific antigens and cultured at 37° C. for 24 hrs. After this time T cells were harvested and stained for CD3/CD4/intracellular IFNγ and analyzed by flow cytometry.

The sequences disclosed in Table 1 yielded positive results in at least one assay described herein, e.g. Western blot, ELISA or ICS.

Example 10

In One Embodiment the Method Includes Detection of Antigen-Specific CD4⁺ T-Cell Responses by Intracellular Cytokine Staining (ICS)

A panel of immunogenic Mtb proteins discovered in Phase I studies that were recognized by rabbit anti-TB sera was selected for further analysis to determine if these proteins could lead to enhanced induction of CD4⁺ T-cells. Thirty-six purified Mtb proteins along with positive controls, culture filtrate proteins (CFP), and recombinant ESAT-6, were included in the ICS assay. The results are summarized in Table 2 and demonstrate that 11 of the 36 proteins significantly stimulated CD4⁺ T-cell responses. Moreover, with equal protein amounts used, 6 Mtb proteins showed greater stimulatory activity than that of ESAT-6.

TABLE 2

| Antigen-specific stimulation of CD4⁺T-cells | | | | | | | | | | | | |
|---|---|---|---|---|---|---|---|---|---|---|---|---|
| ID | Rv3733c | Rv0138 | Rv0740 | Rv0733 | Rv0009 | Rv2882c | Rv1065 | Rv2613c | Rv0475 | Rv2114 | Rv2466c | Rv3763 | Rv2031c |
| % T-cells | 4.3 | 4.3 | 8.3 | 3.7 | 4.0 | 3.6 | 2.8 | 2.0 | 2.1 | 2.9 | 2.6 | 2.5 | 2.2 |
| ID | Rv1347c | Rv0158 | Rv3676 | Rv2821 | Rv2108 | Rv3226c | Rv1056 | Rv0815c | Rv3117 | Rv1073 | Rv0097 | ESAT-6 | Media |
| % T-cells | 2.0 | 2.1 | 1.5 | 1.5 | 1.3 | 2.5 | 2.2 | 1.7 | 1.9 | 1.6 | 1.4 | 3.6 | 1.4 |

One μg each from 36 purified Mtb proteins, along with the control protein ESAT-6, were incubated with mouse dendritic cells for 24 hr. Spleen cells harvested from Mtb-infected mice were added and incubated for an additional 72 hr. The splenocytes were labeled with cychrome-conjugated anti-CD4 antibody and then stained with fluorescein-conjugated anti-γIFN. The cells were washed, fixed and analyzed by flow cytometry. The "% T-cells" indicates the percentage of CD4$^+$ T-cells that released γIFN. Based on previous studies, the percent value at or above 2.5% is significant.

---

What is claimed is:

1. An isolated Mtb peptide or polypeptide selected from the group consisting of SEQ ID NOS: 68, 70, 73, 74, 75, 77, 78, 83, 122, 123, 124, 125, 126, 128, 129, 130, 132, and 133, or an immunogenic fragment thereof.

2. The peptide or polypeptide of claim 1, wherein said peptide or polypeptide reacts with polyclonal antibodies directed to Mtb bacteria.

3. The peptide or polypeptide of claim 1, wherein said peptide or polypeptide is detected by either ELISA or Western blotting.

4. A recombinant Mtb peptide or polypeptide, wherein the amino terminus of said peptide or polypeptide comprises a HA tag or a His tag, and the carboxy terminus of said peptide or polypeptide is selected from the group consisting of: SEQ ID NOS: 68, 70, 73, 74, 75, 77, 78, 83, 122 123, 124, 125, 126, 128, 129, 130, 132, and 133.

5. A recombinant Mtb peptide or polypeptide, wherein the carboxy terminus of said peptide or polypeptide comprises a HA tag or a His tag, and the amino terminus of said peptide or polypeptide is selected from the group consisting of SEQ ID NOS: 68, 70, 73, 74, 75, 77, 78, 83, 122, 123, 124, 125, 126, 128, 129, 130, 132 and 133.

6. A composition comprising at least one isolated Mtb peptide or polypeptide selected from the group consisting of: SEQ ID NOS: 68, 70, 73, 74, 75, 77, 78, 83, 122, 123, 124, 125, 126, 128, 129, 130, 132, and 133, or an immunogenic fragment thereof, and a pharmaceuticallv acceptable carrier.

7. The composition of claim 6, further comprising an adjuvant.

8. A method of generating an immune response in a mammalian host against Mtb comprising administering to said mammalian host at least one peptide, polypeptide or immunogenic fragment thereof of claim 1 or any combination thereof, whereby said immune response against Mtb is generated.

9. The method according to claim 8, further comprising administering an adjuvant to said mammalian host.

10. A kit comprising:

a) at least one peptide or polypeptide of claim 1; and b) an adjuvant.

11. The kit of claim 10 comprising at least two of said polypeptides or peptides.

12. The composition of claim 6, wherein said peptide or polypeptide or immunogenic fragment thereof is a native protein.

13. The composition of claim 6, wherein said peptide or polypeptide or immunogenic fragment thereof is conjugated to a molecule.

14. The composition of claim 13, wherein said molecule is a polysaccharide.

15. The composition of claim 6, wherein said peptide or polypeptide is part of a complex of multiple polypeptide chains.

16. The composition of claim 6, wherein said peptide or polypeptide reacts with polyclonal antibodies directed to Mtb bacteria.

17. The composition of claim 6, wherein said Mtb peptide or polypeptide further comprises a tag, wherein said tag is at the amino terminus or carboxy terminus of said Mtb polypeptide.

18. The composition of claim 17, wherein said tag is a His tag or an HA tag.

19. A kit comprising:

a) at least one composition of claim 6; and b) an adjuvant.

20. The kit of claim 19, comprising at least two of said immunogenic compositions.

21. A method of generating an immune response in a mammalian host against Mtb comprising administering to said mammalian host at least one composition of claim 6, or combination thereof, whereby said immune response against Mtb is generated.

* * * * *

UNITED STATES PATENT AND TRADEMARK OFFICE
CERTIFICATE OF CORRECTION

PATENT NO.       : 7,608,277 B2
APPLICATION NO.  : 11/291616
DATED            : October 27, 2009
INVENTOR(S)      : Roth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 55 days.

Signed and Sealed this

Fourteenth Day of December, 2010

David J. Kappos
*Director of the United States Patent and Trademark Office*